(12) United States Patent
Braganza et al.

(10) Patent No.: US 7,321,040 B2
(45) Date of Patent: Jan. 22, 2008

(54) TRIAZOLO-PYRIDINES AS ANTI-INFLAMMATORY COMPOUNDS

(75) Inventors: John Frederick Braganza, San Diego, CA (US); Michael Anthony Letavic, San Diego, CA (US); Kim F. McClure, Mystic, CT (US)

(73) Assignee: Pfizer Inc., New York, NY (US)

( * ) Notice: Subject to any disclaimer, the term of this patent is extended or adjusted under 35 U.S.C. 154(b) by 393 days.

(21) Appl. No.: 10/776,953

(22) Filed: Feb. 11, 2004

(65) Prior Publication Data
US 2005/0075365 A1    Apr. 7, 2005

Related U.S. Application Data

(60) Provisional application No. 60/447,787, filed on Feb. 14, 2003.

(51) Int. Cl.
C07D 471/02 (2006.01)
C07D 491/02 (2006.01)
C07D 498/02 (2006.01)
C07D 513/02 (2006.01)
C07D 515/02 (2006.01)

(52) U.S. Cl. .................................... 546/119
(58) Field of Classification Search .............. 546/119
See application file for complete search history.

(56) References Cited

U.S. PATENT DOCUMENTS

| | | | |
|---|---|---|---|
| 3,050,525 A | 8/1962 | Bicking | |
| 3,119,742 A | 1/1964 | Heimlich et al. | |
| 3,492,397 A | 1/1970 | Peters et al. | |
| 3,538,214 A | 11/1970 | Polli et al. | |
| 4,060,598 A | 11/1977 | Groppenbächer et al. | |
| 4,173,626 A | 11/1979 | Dempski et al. | |
| 5,716,955 A | 2/1998 | Adams et al. | |
| 5,716,972 A | 2/1998 | Adams et al. | |
| 6,288,062 B1 | 9/2001 | Adams et al. | |
| 2004/0053958 A1 | 3/2004 | Dombroski et al. | |
| 2004/0053959 A1 | 3/2004 | Buzon, Sr. et al. | |
| 2004/0077682 A1 | 4/2004 | Dombroski et al. | |
| 2004/0087615 A1 | 5/2004 | Dombroski et al. | |
| 2004/0092547 A1 | 5/2004 | Dombroski et al. | |

FOREIGN PATENT DOCUMENTS

| | | |
|---|---|---|
| EP | 1 247 810 A1 | 10/2002 |
| WO | WO 00/06563 | 2/2000 |
| WO | WO 00/31065 | 6/2000 |
| WO | WO 00/40243 | 7/2000 |
| WO | WO 00/41698 | 7/2000 |
| WO | WO 00/63204 | 10/2000 |
| WO | WO 01/57038 A1 | 8/2001 |
| WO | WO 02/072576 A1 | 9/2002 |
| WO | WO 02/072579 A1 | 9/2002 |
| WO | WO 03/044021 A2 | 5/2003 |
| WO | WO 04/020609 A2 | 3/2004 |

OTHER PUBLICATIONS

Zhou L. et al., "Inhibition of the CD40 Pathway of Monocyte Activation by Triazolopyrimidine", Clinical Immunology 93(3):232-238 (1999).

(Continued)

Primary Examiner—Margaret D. Seaman
Assistant Examiner—Niloofar Rahmani
(74) Attorney, Agent, or Firm—Gregg C. Benson; Robert T. Ronau

(57) ABSTRACT

The present invention relates to novel triazolo-pyridines of the formula

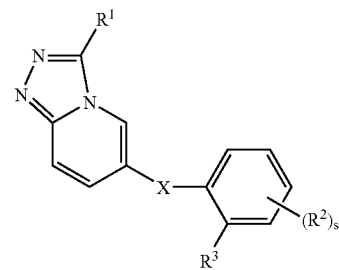

wherein X is $>CH_2$, $>NH$, sulfur, $>S=O$, $>SO_2$ or oxygen; wherein said $>CH_2$ and $>NH$ may optionally be substituted with a suitable substituent;

$R^1$ is selected from the group consisting of hydrogen, $(C_1-C_6)$alkyl and other suitable substituents;

$R^2$ is selected from the group consisting of hydrogen, $(C_1-C_6)$alkyl and other suitable substituents;

s is an integer from 0-4;

$R^3$ is $R^4$, $R^5-(NR^6)-$, $R^5-S-$, $R^5-(S=O)-$, $R^5-(SO_2)-$, $R^5-SO_2-NR^6-$, $R^5-(NR^6)-SO_2-$, $R^5-O-$, $R^5-(C=O)-$, $R^5-(NR^6)-(C=O)-$, $R^5-(C=O)-NR^6-$, $R^5-O-(C=O)-$, $R^5-(C=O)-O-$, $R^5-CR^7=CR^8-$ or $R^5-C\equiv C-$; such that the molecular weight of $R^3$ is less than 500 AMU, preferably less than 250 AMU;

$R^4$, $R^5$ and $R^6$ are each selected from the group consisting of hydrogen, $(C_1-C_6)$alkyl and other suitable substituents;

or a pharmaceutically acceptable salt thereof;

to intermediates for their preparation, to pharmaceutical compositions containing them and to their medicinal use. The compounds of the present invention are potent inhibitors of MAP kinases. They are useful in the treatment of inflammation, osteoarthritis, rheumatoid arthritis, cancer, reperfusion or ischemia in stroke or heart attack, autoimmune diseases and other disorders.

37 Claims, No Drawings

OTHER PUBLICATIONS

Griswold D.E., et al., "Effect of Inhibitors of Eicosanoid Metabolism in Murine Collagen-Induced Arthritis", *Arthritis and Rheumatism*, 31(11): 1406-1412, (1988).

Badger A.M., et al., "Protective Effect of SK&F 86002, a Novel Dual Inhibitor of Arachidonic Acid Metabolism, in Murine Models of Endotoxis Shock: Inhibition of Tumor Necrosis Factor as a Possible Mechanism of Action", *Circulatory Shock*, 27:51-61 (1989).

Votta B.J., et al., "Cytokine Suppressive Anti-inflammatory Compounds Inhibit Bone Resorption In Vitro", *Bone*, 15(5):533-538 (1994).

Lee J.C., et al., "Bicyclic Imidazoles as a Novel Class of Cytokine Biosynthesis Inhibitors", *Annals New York Academy of Sciences*, 696:149-170 (1993).

Turner R.B., et al., "Association Between Interleukin-8 Concentration in Nasal Secretions and Severity of Symptoms of Experimental Rhinovirus Colds", *Clinical Infectious Diseases*, 26:840-846 (1998).

Teran L.M., et al., "Role of Nasal Interleukin-8 in Neutrophil Recruitment and Activation in Children with Virus-Induced Asthma", *American Journal of Respiratory and Critical Care Medicine*, 155:1362-1366 (1997).

Grünberg K., et al., "Experimental Rhinovirus 16 Infection. Effects on Cell Differentials and Soluble Markers in Sputum in Asthmatic Subjects", *American Journal of Respiratory and Critical Care Medicine*, 156:609-616 (1997).

Zhu Z., et al., "Rhinovirus Stimulation of Interleukin-6 In Vivo and In Vitro. Evidence For Nuclear Factor κB-dependent Transcriptional Activation", *The Journal of Clinical Investigation*, 97(2):421-430 (1996).

Subauste M.C., et al., "Infection of a Human Respiratory Epithelial Cell Line with Rhinovirus. Induction of Cytokine Release and Modulation of Susceptibility to Infection by Cytokine Exposure", *Journal of Clinical Investigation*, 96:549-557 (1995).

Greene, T.W. et al., "The Role of Protective Groups in Organic Synthesis", *Protective Groups in Organic Synthesis*, 2 Ed.:1-9 (1991).

TRIAZOLO-PYRIDINES AS ANTI-INFLAMMATORY COMPOUNDS

CROSS REFERENCE TO RELATED APPLICATIONS

The present application claims benefit of U.S. Provisional Application No. 60/447,787 filed Feb. 14, 2003.

BACKGROUND OF THE INVENTION

The present invention relates to novel triazolo-pyridines, to methods of preparation, to intermediates for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, reperfusion or ischemia in stroke or heart attack, autoimmune diseases and other disorders.

MAP kinases include cytokine suppressive anti-inflammatory drugs, i.e., compounds which are capable of inhibiting MAPK14/CSBP/p38/RK kinase, Extracellular signal regulated kinase-1 (ERK1 or MAPK3), Extracellular signal regulated kinase-2 (ERK2 or MAPK2), Extracellular signal regulated kinase-3 (ERK3 or MAPK6), Extracellular signal regulated kinase-5 (ERK5 or MAPK7), Extracellular signal regulated kinase-6 (ERK6 or MAPK12), MAPK1, MAPK4, MAPK8, MAPK9, MAPK10, MAPK11, and MAPK13. Certain compounds are selective inhibitors of one or more of the aforementioned kinases preferably p 38 Kinases.

MAPK14/CSBP/p38/RK kinase inhibitors are well known to those skilled in the art. International Patent Publications WO 02/72576 and 02/072579, both published Sep. 19, 2002, and European Patent Publication EP 1247810, published Oct. 9, 2002, refer to certain inhibitors of MAP Kinases. U.S. Provisional Application 60/407,085, 60/407,177, 60/407,489, 60/407,088, 60/407,089, 60/407,082, all filed Aug. 30, 2002 refer to other MAP Kinases inhibtors. International Patent Publication WO 00/40243, published Jul. 13, 2000, refers to pyridine substituted pyridine compounds and states that these compounds are p38 inhibitors. International Patent Publication WO 00/63204, published Oct. 26, 2000, refers to substituted azole compounds and states that these compounds are p38 inhibitors. International Patent Publication WO 00/31065, published Jun. 2, 2000, refers to certain heterocyclic compounds and states that these compounds are p38 inhibitors. International Patent Publication WO 00/06563, published Feb. 10, 2000, refers to substituted imidazole compounds and states that these compounds are p38 inhibitors. International Patent Publication WO 00/41698, published Jul. 20, 2000, refers to certain ω-carboxy aryl substituted diphenyl urea compounds and states that these compounds are p38 inhibitors. U.S. Pat. No. 6,288,062 refers to certain substituted oxazole compounds and states that these compounds are p38 inhibitors. U.S. Pat. No. 5,716,955 refers to certain substituted imidazole compounds and states that these compounds are p38 inhibitors. U.S. Pat. No. 5,716,972 refers to certain pyridinyl substituted imidazole compounds and states that these compounds are p38 inhibitors. U.S. Pat. No. 5,756,499 refers to certain substituted imidazole compounds and states that these compounds are p38 inhibitors.

SUMMARY OF THE INVENTION

The present invention relates to a compound of the formula

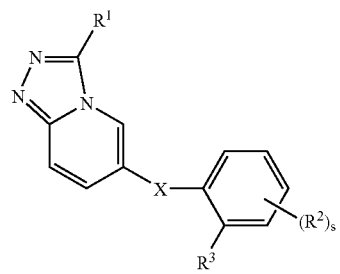

wherein the molecular weight of the compound of formula I is less than 1000 AMU, preferably less than 750 AMU;

X is $>CH_2$, $>NH$, sulfur, $>S=O$, $>SO_2$ or oxygen; wherein said $>CH_2$ and $>NH$ may optionally be substituted with a suitable substituent;

$R^1$ is selected from the group consisting of hydrogen, $(C_1-C_6)$alkyl and other suitable substituents;

$R^2$ is selected from the group consisting of hydrogen, $(C_1-C_6)$alkyl and other suitable substituents;

s is an integer from 0-4;

$R^3$ is $R^4$, $R^5-(NR^6)-$, $R^5-S-$, $R^5-(S=O)-$, $R^5-(SO_2)-$, $R^5-SO_2-NR^6-$, $R^5-(NR^6)-SO_2-$, $R^5-O-$, $R^5-(C=O)-$, $R^5-(NR^6)-(C=O)-$, $R^5-(C=O)-NR^6-$, $R^5-O-(C=O)-$, $R^5-(C=O)-O-$, $R^5-CR^7=CR^8-$ or $R^5-C\equiv C-$; such that the molecular weight of $R^3$ is less than 500 AMU, preferably less than 250 AMU;

$R^4$, $R^5$ and $R^6$ are each selected from the group consisting of hydrogen, $(C_1-C_6)$alkyl and other suitable substituents;

wherein the molecular weight of the compound of formula I is less than 1000, preferably less than 750 AMU, more preferably less than 500;

or pharmaceutically acceptable salts and prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and geometric isomers and mixtures thereof and all optical isomers of compounds of the formula I (e.g., R and S enantiomers), as well as racemic, diastereomeric and other mixtures of such isomers.

The compounds and prodrugs of the present invention can exist in several tautomeric forms, including the enol and enamine form, and the keto and imine form. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

As used herein, the term "AMU" refers to the common name for the relative molecular mass. The mass is determined by adding together the atomic weights indicated by the formula of the substituent, eg., methyl has an AMU of 15.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl.

As used herein, the term "alkenyl," or "C=C" as well as the alkenyl moieties of other groups referred to herein (e.g., $R^9$-alkenyl), may be linear or branched (such as ethylene, n-propylene, isopropylene, n-butylene, iso-butylene, secondary-butylene, tertiary-butylene); optionally substituted by 1 to 3 suitable substituents as defined above such as fluoro, chloro, trifluoromethyl or $(C_1-C_6)$alkyl. Preferred alkylenes include $(C_1-C_4)$alkylene, most preferably ethylene.

As used herein, the term "alkynyl," as well as the alkynyl moieties of other groups referred to herein (e.g., $R^9$-alkynyl), may be linear or branched (such as ethynyl, n-propynyl, isopropynyl, n-butynyl, iso-butynyl, secondary-butynyl, tertiary-butynyl); optionally substituted by a suitable substituent as defined above such as fluoro, chloro, trifluoromethyl or $(C_1-C_6)$alkyl. Preferred alkynyls include $(C_1-C_4)$ alkynyl, most preferably acetynyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1]octanyl and bicyclo[5.2.0]nonanyl, etc.); optionally containing 1-2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$ alkyl. Preferred cycloalkyls include the $(C_3-C_6)$cycloalkyls cyclobutyl, cyclopentyl and cyclohexyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term aryl refers to an optionally substituted six-membered aromatic ring, including polyaromatic rings. Examples of aryl include phenyl, naphthyl and biphenyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, benzimidazolyl, and the like; optionally substituted by 1 to 3 substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^2$ or $R^5$ heteroaryls).

The term "heterocyclic" as used herein refers to a cyclic group containing 1 to 9 carbon atoms and 1 to 4 hetero atoms selected from N, O, S or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl; pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined above such as fluoro, chloro, trifluoromethyl, $(C_1-C_6)$alkoxy, $(C_6-C_{10})$ aryloxy, trifluoromethoxy, difluoromethoxy or $(C_1-C_6)$alkyl. Preferred heterocyclics include tetrahydrofuranyl, pyrrolidinyl, piperidinyl, piperazinyl and morpholinyl.

Embodiment as used herein refers to specific groupings of compounds or uses into discrete subgenera. Such subgenera may be cognizable according to one particular substituent such as a specific $R^2$ group. Other subgenera are cognizable according to combinations of various substituents, such as all compounds wherein $R^1$ is optionally substituted phenyl and $R^4$ is $(R^9)_m$—$(C_1-C_6)$alkyl. The phrase "in combination with each of the aforementioned embodiments" refers to combinations of the identified embodiment with each embodiment previously identified in the specification. Thus an embodiment of compounds wherein $R^5$ is $(R^9)_m$—$(C_1$-$C_6)$alkyl "in combination with each of the aforementioned embodiments" refers to additional embodiments comprising combinations of the $R^5$ $(R^9)_m$—$(C_1$-$C_6)$alkyl embodiment with each embodiment previously identified in the specification.

More specifically, the present invention relates to a compound of the formula

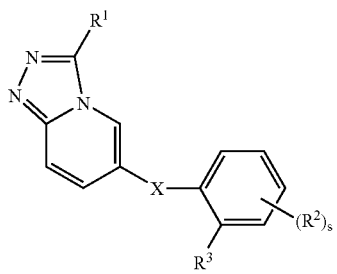

I wherein $R^1$ is selected from the group of substituents consisting of hydrogen, —C≡N, $(C_1$-$C_6)$alkyl, $(C_2$-$C_6)$alkenyl, $(C_2$-$C_6)$alkynyl, $(C_3$-$C_{10})$cycloalkyl, phenyl, $(C_1$-$C_{10})$heteroaryl, $(C_1$-$C_{10})$heterocyclic and $(R^{17})_2$—N—; wherein each of the aforesaid $(C_1$-$C_6)$alkyl, $(C_3$-$C_{10})$cycloalkyl, phenyl, $(C_1$-$C_{10})$heteroaryl and $(C_1$-$C_{10})$heterocyclic substituents may optionally be independently substituted by one to four moieties independently selected from the group consisting of halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_3$-$C_{10})$cycloalkyl, $(C_1$-$C_{10})$heteroaryl, $(C_1$-$C_{10})$heterocyclic, formyl, —C≡N, $(C_1$-$C_6)$alkyl-(C=O)—, phenyl-(C=O)—, HO—(C=O)—, $(C_1$-$C_6)$alkyl-O—(C=O)—, $(C_1$-$C_6)$alkyl-NH—(C=O)—, [$(C_1$-$C_6)$alkyl]$_2$—N—(C=O)—, phenyl-NH—(C=O)—, phenyl-[(($C_1$-$C_6$)alkyl)—N]—(C=O)—, —NO$_2$, amino, $(C_1$-$C_6)$alkylamino, [$(C_1$-$C_6)$alkyl]$_2$-amino, $(C_1$-$C_6)$alkyl-(C=O)—NH—, $(C_1$-$C_6)$alkyl-(C=O)—[(($C_1$-$C_6$)alkyl)—N]—, phenyl-(C=O)—NH—, phenyl-(C=O)—[(($C_1$-$C_6$)alkyl)—N]—, H$_2$N—(C=O)—NH—, $(C_1$-$C_6)$alkyl-HN—(C=O)—NH—, [$(C_1$-$C_6)$alkyl]$_2$—N—(C=O)—NH—, $(C_1$-$C_6)$alkyl-HN—(C=O)—[(($C_1$-$C_6$)alkyl)—N]—, [$(C_1$-$C_6)$alkyl]$_2$—N—(C=O)—[(($C_1$-$C_6$)alkyl)—N]—, phenyl-HN—(C=O)—NH—, (phenyl)$_2$—N—(C=O)—NH—, phenyl-HN—(C=O)—[(($C_1$-$C_6$)alkyl)—N]—, (phenyl-)$_2$N—(C=O)—[(($C_1$-$C_6$)alkyl)—N]—, $(C_1$-$C_6)$alkyl-O—(C=O)—NH—, $(C_1$-$C_6)$alkyl-O—(C=O)—[(($C_1$-$C_6$)alkyl)—N]—, phenyl-O—(C=O)—NH—, phenyl-O—(C=O)—[(($C_1$-$C_6$)alkyl)—N]—, $(C_1$-$C_6)$alkyl-SO$_2$NH—, phenyl-SO$_2$NH—, $(C_1$-$C_6)$alkyl-SO$_2$—, phenyl-SO$_2$—, hydroxy, $(C_1$-$C_6)$alkoxy, perhalo$(C_1$-$C_6)$alkoxy, phenoxy, $(C_1$-$C_6)$alkyl-(C=O)—O—, phenyl-(C=O)—O—, H$_2$N—(C=O)—O—, $(C_1$-$C_6)$alkyl-HN—(C=O)—O—, [$(C_1$-$C_6)$alkyl]$_2$—N—(C=O)—O—, phenyl-HN—(C=O)—O— and (phenyl)$_2$—N—(C=O)—O—; wherein when said $R^1$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of $(C_1$-$C_6)$alkyl, halo, $(C_1$-$C_6)$alkoxy, perhalo$(C_1$-$C_6)$alkyl and perhalo$(C_1$-$C_6)$alkoxy;

s is an integer from zero to four;
each $R^2$ is independently selected from the group consisting of hydrogen, halo, $(C_1$-$C_4)$alkyl, and —CF$_3$;
$R^3$ is $R^4$, $R^5$—(NR$^6$)—, $R^5$—S—, $R^5$—(S=O)—, $R^5$—(SO$_2$)—, $R^5$—SO$_2$—NR$^6$—, $R^5$—(NR$^6$)—SO$_2$—, $R^5$—O—, $R^5$—(C=O)—, $R^5$—(NR$^6$)—(C=O)—, $R^5$—(C=O)—NR$^6$—, $R^5$—O—(C=O)—, $R^5$—(C=O)—O—, $R^5$—CR$^7$=CR$^8$— or $R^5$—C≡C—;

$R^4$ is hydrogen, halo, —C≡N, $(R^9)_m$—$(C_1$-$C_6)$alkyl, $(R^9)_m$—$(C_2$-$C_6)$alkenyl, perhalo$(C_1$-$C_6)$alkyl, $(R^9)_m$-phenyl, $(R^9)_m$—$(C_1$-$C_{10})$heteroaryl, $(R^9)_m$—$(C_1$-$C_{10})$heterocyclic, or $(R^9)_m$—$(C_3$-$C_{10})$cycloalkyl, $R^5$ is hydrogen, —C≡N, $(R^9)_m$—$(C_1$-$C_6)$alkyl, $(R^9)_m$—$(C_2$-$C_6)$alkenyl, $(R^9)_m$—$(C_2$-$C_6)$alkynyl, perhalo$(C_1$-$C_6)$alkyl, $(R^9)_m$-phenyl, $(R^9)_m$—$(C_1$-$C_{10})$heteroaryl, $(R^9)_m$—$(C_1$-$C_{10})$heterocyclic, or $(R^9)_m$—$(C_3$-$C_{10})$cycloalkyl;

m is an integer from one to three;

$R^6$ is selected from the group consisting of hydrogen, $(C_1$-$C_6)$alkyl, $(C_2$-$C_6)$alkenyl, $(C_2$-$C_6)$alkynyl, $(C_3$-$C_{10})$cycloalkyl, phenyl, $(C_1$-$C_{10})$heteroaryl, $(C_1$-$C_{10})$heterocyclic, $R^{13}$—(C=O)—, and $R^{13}$—(SO$_2$)—; wherein each of the aforesaid $(C_1$-$C_6)$alkyl, $(C_3$-$C_{10})$cycloalkyl, phenyl, $(C_1$-$C_{10})$heteroaryl and $(C_1$-$C_{10})$heterocyclic substituents may optionally be independently substituted on any carbon atom by one to four moieties per substituent independently selected from the group consisting of halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_3$-$C_{10})$cycloalkyl, $(C_1$-$C_{10})$heteroaryl, $(C_1$-$C_{10})$heterocyclic, formyl, —C≡N, $(C_1$-$C_6)$alkyl-(C=O)—, phenyl-(C=O)—, HO—(C=O)—, $(C_1$-$C_6)$alkyl-O—(C=O)—, $(C_1$-$C_6)$alkyl-NH—(C=O)—, [$(C_1$-$C_6)$alkyl]$_2$—N—(C=O)—, phenyl-NH—(C=O)—, phenyl-[(($C_1$-$C_6$)alkyl)—N]—(C=O)—, —NO$_2$, amino, $(C_1$-$C_6)$alkylamino, [$(C_1$-$C_6)$alkyl]$_2$-amino, $(C_1$-$C_6)$alkyl-(C=O)—NH—, $(C_1$-$C_6)$alkyl-(C=O)—[(($C_1$-$C_6$)alkyl)—N]—, phenyl-(C=O)—NH—, phenyl-(C=O)—[(($C_1$-$C_6$)alkyl)—N]—, H$_2$N—(C=O)—NH—, $(C_1$-$C_6)$alkyl-HN—(C=O)—NH—, [$(C_1$-$C_6)$alkyl]$_2$—N—(C=O)—NH—, $(C_1$-$C_6)$alkyl-HN—(C=O)—[(($C_1$-$C_6$)alkyl)—N]—, [$(C_1$-$C_6)$alkyl]$_2$—N—(C=O)—[(($C_1$-$C_6$)alkyl)—N]—, phenyl-HN—(C=O)—NH—, (phenyl)$_2$—N—(C=O)—NH—, phenyl-HN—(C=O)—[(($C_1$-$C_6$)alkyl)—N]—, (phenyl-)$_2$N—(C=O)—[(($C_1$-$C_6$)alkyl)—N]—, $(C_1$-$C_6)$alkyl-O—(C=O)—NH—, $(C_1$-$C_6)$alkyl-O—(C=O)—[(($C_1$-$C_6$)alkyl)—N]—, phenyl-O—(C=O)—NH—, phenyl-O—(C=O)—[(($C_1$-$C_6$)alkyl)—N]—, $(C_1$-$C_6)$alkyl-SO$_2$NH—, phenyl-SO$_2$NH—, $(C_1$-$C_6)$alkyl-SO$_2$—, phenyl-SO$_2$—, hydroxy, $(C_1$-$C_6)$alkoxy, perhalo$(C_1$-$C_6)$alkoxy, phenoxy, $(C_1$-$C_6)$alkyl-(C=O)—O—, phenyl-(C=O)—O—, H$_2$N—(C=O)—O—, $(C_1$-$C_6)$alkyl-HN—(C=O)—O—, [$(C_1$-$C_6)$alkyl]$_2$—N—(C=O)—O—, phenyl-HN—(C=O)—O—, and (phenyl-)$_2$N—(C=O)—O—; wherein when said $R^6$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of $(C_1$-$C_6)$alkyl, halo, $(C_1$-$C_6)$alkoxy, perhalo$(C_1$-$C_6)$alkyl and perhalo$(C_1$-$C_6)$alkoxy;

$R^7$ is selected from the group consisting of hydrogen, $(C_1$-$C_6)$alkyl, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, and $(C_3$-$C_{10})$cycloalkyl;

$R^8$ is hydrogen, or $(C_1$-$C_6)$alkyl;

wherein when $R^9$ is a substituent on a carbon atom each $R^9$ is independently selected from the group consisting of hydrogen, halo, $R^{11}$—$(C_1$-$C_6)$alkyl, $R^{11}$—$(C_2$-$C_6)$alkenyl, $R^{11}$—$(C_2$-$C_6)$alkynyl, azido, perhalo$(C_1$-$C_6)$alkyl, $(C_1$-$C_6)$alkyl-S—, $(C_1$-$C_6)$alkyl-SO$_2$—, $R^{11}$—[N$(R^{10})$]—SO$_2$—, —NO$_2$, $(R^{11})_2$N—, $R^{11}$—SO$_2$—[N$(R^{10})$]—, $R^{11}$—(C=O)—[N$(R^{10})$]—, $(R^{11})$—[N$(R^{10})$]—(C=O)—[N$(R^{10})$]—, $R^{11}$—O—(C=O)—[N$(R^{10})$]—, —C≡N, $R^{11}$—(C=O)—, $R^{11}$—O—(C=O)—, $(R^{11})$—[N$(R^{10})$]—(C=O)—, $R^{11}$—O—, perhalo$(C_1$-$C_6)$alkoxy, $R^{11}$—(C=O)—O—, $(R^{11}$—O—(C=O)—O— and $(R^{11})$—[N$(R^{10})$]—(C=O)—O—;

wherein when $R^9$ is a substituent on a nitrogen atom each $R^9$ is independently selected from the group consisting of hydrogen, $R^{11}$—$(C_1$-$C_6)$alkyl, $R^{11}$—$(C_2$-$C_6)$alkenyl, $R^{11}$—$(C_2$-$C_6)$alkynyl, perhalo$(C_1$-$C_6)$alkyl, $(C_1$-$C_6)$alkyl-SO$_2$—, $R^{11}$—[N$(R^{10})$]—SO$_2$—, $R^{11}$—(C=O)—, $R^{11}$—O—(C=O)— and $(R^{11})$—[N$(R^{10})$]—(C=O)—;

$R^{10}$ is hydrogen or $(C_1$-$C_4)$alkyl;

$R^{11}$ is selected from the group consisting of hydrogen, $R^{12}$—$(C_1$-$C_6)$alkyl, $(C_3$-$C_6)$alkenyl, $(C_3$-$C_6)$alkynyl, $(C_1$-$C_{10})$heterocyclic, $(C_1$-$C_{10})$heteroaryl, $(C_3$-$C_{10})$cycloalkyl, and phenyl; wherein each of the aforesaid $R^{12}$—$(C_1$-$C_6)$alkyl, $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, —C≡N, $(C_1$-$C_6)$alkyl, $(C_1$-$C_6)$alkyl-O—(C=O)—, and $(C_1$-$C_6)$alkoxy;

$R^{12}$ is selected from the group consisting of hydrogen, hydroxy, $(C_1$-$C_{10})$heterocyclic, $(C_1$-$C_{10})$heteroaryl, $(C_3$-$C_{10})$cycloalkyl, and phenyl; wherein each of the aforesaid $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, —C≡N, $(C_1$-$C_6)$alkyl, and $(C_1$-$C_6)$alkoxy;

$R^{13}$ is selected from the group consisting of hydrogen, $(C_1$-$C_6)$alkyl, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, $(C_3$-$C_{10})$cycloalkyl, hydroxy, $(C_1$-$C_6)$alkoxy, perhalo$(C_1$-$C_6)$alkoxy, phenoxy, $(C_1$-$C_{10})$heteroaryl-O—, $(C_1$-$C_{10})$heterocyclic-O—, $(C_3$-$C_{10})$cycloalkyl-O—, $(C_1$-$C_6)$alkyl-S—, amino, $(C_1$-$C_6)$alkylamino, [$(C_1$-$C_6)$alkyl]$_2$-amino, $(C_1$-$C_6)$alkyl-SO$_2$—NH—, $(C_1$-$C_6)$alkyl-(C=O)—NH—, $(C_1$-$C_6)$alkyl-(C=O)—[(($(C_1$-$C_6)$alkyl)—N]—, phenyl-(C=O)—NH—, and phenyl-(C=O)—[(($(C_1$-$C_6)$alkyl)—N]—;

X is >C$(R^{14})_2$, >NR$^{15}$, sulfur, >S=O, >SO$_2$ or oxygen;

each $R^{14}$ is independently selected from the group consisting of hydrogen, halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, $(C_3$-$C_{10})$cycloalkyl, hydroxy, $(C_1$-$C_6)$alkoxy, perhalo$(C_1$-$C_6)$alkoxy, phenoxy, $(C_1$-$C_{10})$heteroaryl-O—, $(C_1$-$C_{10})$heterocyclic-O—, $(C_3$-$C_{10})$cycloalkyl-O—, $(C_1$-$C_6)$alkyl-S—, $(C_1$-$C_6)$alkyl-SO$_2$—, $(C_1$-$C_6)$alkyl-NH—SO$_2$—, —NO$_2$, amino, $(C_1$-$C_6)$alkylamino, [$(C_1$-$C_6)$alkyl]$_2$-amino, $(C_1$-$C_6)$alkyl-SO$_2$—NH—, $(C_1$-$C_6)$alkyl-(C=O)—NH—, $(C_1$-$C_6)$alkyl-(C=O)—[(($(C_1$-$C_6)$alkyl)—N]—, phenyl-(C=O)—NH—, phenyl-(C=O)—[(($(C_1$-$C_6)$alkyl)—N]—, —C≡N, $(C_1$-$C_6)$alkyl-(C=O)—, phenyl-(C=O)—, $(C_1$-$C_{10})$heteroaryl-(C=O)—, $(C_1$-$C_{10})$heterocyclic-(C=O)—, $(C_3$-$C_{10})$cycloalkyl-(C=O)—, HO—(C=O)—, $(C_1$-$C_6)$alkyl-O—(C=O)—, H$_2$N—(C=O)—, $(C_1$-$C_6)$alkyl-NH—(C=O)—, [$(C_1$-$C_6)$alkyl]$_2$—N—(C=O)—, phenyl-NH—(C=O)—, phenyl-[(($(C_1$-$C_6)$alkyl)—N]—(C=O)—, $(C_1$-$C_{10})$heteroaryl-NH—(C=O)—, $(C_1$-$C_{10})$heterocyclic-NH—(C=O)—, $(C_3$-$C_{10})$cycloalkyl-NH—(C=O)— and $(C_1$-$C_6)$alkyl-(C=O)—O—; wherein two $R^{14}$ substituents may be optionally taken together with the carbon atoms to which they are attached to form a five to six membered carbocyclic or heterocyclic ring;

$R^{15}$ is selected from the group consisting of hydrogen, $(C_1$-$C_6)$alkyl, $(C_2$-$C_6)$alkenyl, $(C_2$-$C_6)$alkynyl, $(C_3$-$C_{10})$cycloalkyl, phenyl, $(C_1$-$C_{10})$heteroaryl, $(C_1$-$C_{10})$heterocyclic, $R^{16}$—(C=O)—, and $R^{16}$—(SO$_2$)—; wherein each of the aforesaid $(C_1$-$C_6)$alkyl, $(C_3$-$C_{10})$cycloalkyl, phenyl, $(C_1$-$C_{10})$heteroaryl and $(C_1$-$C_{10})$heterocyclic substituents may optionally be independently substituted on any carbon atom by one to four moieties per substituent independently selected from the group consisting of halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_3$-$C_{10})$cycloalkyl, $(C_1$-$C_{10})$heteroaryl, $(C_1$-$C_{10})$heterocyclic, formyl, —C≡N, $(C_1$-$C_6)$alkyl-(C=O)—, phenyl-(C=O)—, HO—(C=O)—, $(C_1$-$C_6)$alkyl-O—(C=O)—, $(C_1$-$C_6)$alkyl-NH—(C=O)—, [$(C_1$-$C_6)$alkyl]$_2$—N—(C=O)—, phenyl-NH—(C=O)—, phenyl-[(($(C_1$-$C_6)$alkyl)—N]—(C=O)—, —NO$_2$, amino, $(C_1$-$C_6)$alkylamino, [$(C_1$-$C_6)$alkyl]$_2$-amino, $(C_1$-$C_6)$alkyl-(C=O)—NH—, $(C_1$-$C_6)$alkyl-(C=O)—[(($(C_1$-$C_6)$alkyl)—N]—, phenyl-(C=O)—NH—, phenyl-(C=O)—[(($(C_1$-$C_6)$alkyl)—N]—, H$_2$N—(C=O)—NH—, $(C_1$-$C_6)$alkyl-HN—(C=O)—NH—, [$(C_1$-$C_6)$alkyl]$_2$—N—(C=O)—NH—, $(C_1$-$C_6)$alkyl-HN—(C=O)—[(($(C_1$-$C_6)$alkyl)—N]—, [$(C_1$-$C_6)$alkyl]$_2$—N—(C=O)—[(($(C_1$-$C_6)$alkyl)—N]—, phenyl-HN—(C=O)—NH—, (phenyl)$_2$N—(C=O)—NH—, phenyl-HN—(C=O)—[(($(C_1$-$C_6)$alkyl)—N]—, (phenyl-)$_2$N—(C=O)—[(($(C_1$-$C_6)$alkyl)—N]—, $(C_1$-$C_6)$alkyl-O—(C=O)—NH—, $(C_1$-$C_6)$alkyl-O—(C=O)—[(($(C_1$-$C_6)$alkyl)—N]—, phenyl-O—(C=O)—NH—, phenyl-O—(C=O)—[(($(C_1$-$C_6)$alkyl)—N]—, $(C_1$-$C_6)$alkyl-SO$_2$NH—, phenyl-SO$_2$NH—, $(C_1$-$C_6)$alkyl-SO$_2$—, phenyl-SO$_2$—, hydroxy, $(C_1$-$C_6)$alkoxy, perhalo$(C_1$-$C_6)$alkoxy, phenoxy, $(C_1$-$C_6)$alkyl-(C=O)—O—, phenyl-(C=O)—O—, H$_2$N—(C=O)—O—, $(C_1$-$C_6)$alkyl-HN—(C=O)—O—, [$(C_1$-$C_6)$alkyl]$_2$—N—(C=O)—O—, phenyl-HN—(C=O)—O—, and (phenyl-)$_2$N—(C=O)—O—; wherein each of the aforesaid $(C_1$-$C_{10})$heteroaryl and $(C_1$-$C_{10})$heterocyclic substituents may optionally be independently substituted on any nitrogen atom by a substituent selected from the group consisting of $(C_1$-$C_6)$alkyl, $(C_2$-$C_6)$alkenyl, $(C_2$-$C_6)$alkynyl, perhalo$(C_1$-$C_6)$alkyl, phenyl, $(C_3$-$C_{10})$cycloalkyl, $(C_1$-$C_{10})$heteroaryl, $(C_1$-$C_{10})$heterocyclic, formyl, $(C_1$-$C_6)$alkyl-(C=O)—, phenyl-(C=O)—, HO—(C=O)—, $(C_1$-$C_6)$alkyl-O—(C=O)—, $(C_1$-$C_6)$alkyl-NH—(C=O)—, [$(C_1$-$C_6)$alkyl]$_2$—N—(C=O)—, phenyl-NH—(C=O)—, phenyl-[(($(C_1$-$C_6)$alkyl)—N]—(C=O)—, $(C_1$-$C_6)$alkyl-SO$_2$— and phenyl-SO$_2$—; wherein when said $R^{15}$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of $(C_1$-$C_6)$alkyl, halo, $(C_1$-$C_6)$alkoxy, perhalo$(C_1$-$C_6)$alkyl and perhalo$(C_1$-$C_6)$alkoxy;

$R^{16}$ is selected from the group consisting of hydrogen, $(C_1$-$C_6)$alkyl, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, $(C_3$-$C_{10})$cycloalkyl, $(C_1$-$C_6)$alkoxy and perhalo$(C_1$-$C_6)$alkoxy;

each $R^{17}$ is independently selected from hydrogen, $(C_1$-$C_6)$alkyl, phenyl, $(C_1$-$C_{10})$heteroaryl, $(C_1$-$C_{10})$heterocyclic and $(C_3$-$C_{10})$cycloalkyl; wherein each of the aforesaid $R^{17}$ substituents $(C_1$-$C_6)$alkyl, phenyl, $(C_1$-$C_{10})$heteroaryl, $(C_1$-$C_{10})$heterocyclic and $(C_3$-$C_{10})$cycloalkyl may optionally be substituted on any carbon atom by one to four moieties per substituent independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)$alkyl$]_2$-amino, $(C_1-C_6)$alkyl-SO$_2$—NH—, $(C_1-C_6)$alkyl-(C=O)—NH—, $(C_1-C_6)$alkyl-(C=O)—[$((C_1-C_6)$alkyl)—N]—, phenyl-(C=O)—NH—, phenyl-(C=O)—[$((C_1-C_6)$alkyl)—N]—, —C≡N, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, $[(C_1-C_6)$alkyl$]_2$—N—(C=O)—, phenyl-NH—(C=O)—, phenyl-[$((C_1-C_6)$alkyl)—N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein each of the aforesaid $R^{17}$ substituents $(C_1-C_{10})$heteroaryl and $(C_1-C_{10})$heterocyclic may optionally be substituted on any nitrogen atom by a moiety selected from the group consisting of $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, $(C_1-C_6)$alkyl-SO$_2$—, $(C_1-C_6)$alkyl-NH—SO$_2$—, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)— $(C_1-C_6)$alkyl-NH—(C=O)—, $[(C_1-C_6)$alkyl$]_2$—N—(C=O)—, phenyl-NH—(C=O)—, phenyl-[$((C_1-C_6)$alkyl)—N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^{17}$ $(C_1-C_6)$alkyl groups may be taken together with the nitrogen atom to which they are attached to form a five to six membered heterocyclic or heteroaryl ring;

or the pharmaceutically acceptable salts thereof.

An embodiment of the present invention includes those compounds of formula I wherein $R^3$ is $R^4$.

Another embodiment of the present invention includes those compounds of formula I wherein $R^3$ is $R^4$ and $R^4$ is hydrogen, halo, —C≡N or perhalo$(C_1-C_6)$alkyl.

Another embodiment of the present invention includes those compounds of formula I wherein $R^3$ is $R^4$ and $R^4$ is $(R^9)_m$—$(C_1-C_6)$alkyl. A more specific embodiment of the $(R^9)_m$—$(C_1-C_6)$alkyl group of compounds of the present invention includes those compounds of formula I wherein $R^4$ is $(R^9)_m$—$(C_1-C_6)$alkyl; m is 1; $R^9$ is selected from the group consisting of hydrogen, halo, $R^{11}$—$(C_1-C_6)$alkyl, $R^{11}$—$(C_2-C_6)$alkenyl, $R^{11}$—$(C_2-C_6)$alkynyl, perhalo$(C_1-C_6)$alkyl, $(C_1-C_6)$alkyl-S—, $(C_1-C_6)$alkyl-SO$_2$—, $R^{11}$—[N(R$^{10}$)]—SO$_2$—, —NO$_2$, $R^{11}$—SO$_2$—[N(R$^{10}$)]—, —C≡N, and perhalo$(C_1-C_6)$alkoxy.

Another more specific embodiment of the $(R^9)_m$—$(C_1-C_6)$alkyl group of compounds of the present invention includes those compounds of formula I wherein $R^4$ is $(R^9)_m$—$(C_1-C_6)$alkyl; m is 1; $R^9$ is selected from the group consisting of $(R^{11})_2$N—, $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, $R^{11}$—(C=O)—, $R^{11}$—O—(C=O)—, $(R^{11})$—[N(R$^{10}$)]—(C=O)—, $R^{11}$—O—, $R^{11}$—(C=O)—O—, $R^{11}$—O—(C=O)—O— and $(R^{11})$—[N(R$^{10}$)]—(C=O)—O—.

Another more specific embodiment of the $(R^9)_m$—$(C_1-C_6)$alkyl group of compounds of the present invention includes those compounds of formula I wherein $R^4$ is $(R^9)_m$—$(C_1-C_6)$alkyl; m is 1; $R^9$ is selected from the group consisting of $(R^{11})_2$N—, $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, $R^{11}$—(C=O)—, $R^{11}$—O—(C=O)—, $(R^{11})$—[N(R$^{10}$)]—(C=O)—, $R^{11}$—O—, $R^{11}$—(C=O)—O—, $R^{11}$—O—(C=O)—O— and $(R^{11})$—[N(R$^{10}$)]—(C=O)—O—; and $R^{11}$ is selected from the group selected from hydrogen, $R^{12}$—$(C_1-C_6)$alkyl, $(C_3-C_6)$alkenyl, and $(C_3-C_6)$alkynyl.

Another more specific embodiment of the $(R^9)_m$—$(C_1-C_6)$alkyl group of compounds of the present invention includes those compounds of formula I wherein $R^4$ is $(R^9)_m$—$(C_1-C_6)$alkyl; m is 1; $R^9$ is selected from the group consisting of $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, $R^{11}$—(C=O)—, $R^{11}$—O—(C=O)—, $(R^{11})$—[N(R$^{10}$)]—(C=O)—, $R^{11}$—O—, $R^{11}$—(C=O)—O—, $R^{11}$—O—(C=O)—O— and $(R^{11})$—[N(R$^{10}$)]—(C=O)—O—; and $R^{11}$ is selected from the group selected from $(C_1-C_{10})$heterocyclic, $(C_1-C_{10})$heteroaryl, $(C_3-C_{10})$cycloalkyl, and phenyl; wherein each of the aforesaid $(C_1-C_{10})$heterocyclic, $(C_1-C_{10})$heteroaryl, $(C_3-C_{10})$cycloalkyl, and phenyl substituents may optionally be substituted with one to three moieties independently selected from halo, $(C_1-C_6)$alkyl, and $(C_1-C_6)$alkoxy.

Another more specific embodiment of the $(R^9)_m$—$(C_1-C_6)$alkyl group of compounds of the present invention includes those compounds of formula I wherein $R^4$ is $(R^9)_m$—$(C_1)$alkyl; m is 1; $R^9$ is selected from the group consisting of hydrogen, halo, $R^{11}$—$(C_1-C_6)$alkyl, $R^{11}$—$(C_2-C_6)$alkenyl, $R^{11}$—$(C_2-C_6)$alkynyl, perhalo$(C_1-C_6)$alkyl, $(C_1-C_6)$alkyl-S—, $(C_1-C_6)$alkyl-SO$_2$—, $R^{11}$—[N(R$^{10}$)]—SO$_2$—, —NO$_2$, $R^{11}$—SO$_2$—[N(R$^{10}$)]—, —C≡N, and perhalo$(C_1-C_6)$alkoxy; and $R^{11}$ is selected from the group consisting of $(C_1-C_{10})$heterocyclic, $(C_1-C_{10})$heteroaryl, $(C_3-C_{10})$cycloalkyl, and phenyl; wherein each of the aforesaid $(C_1-C_{10})$heterocyclic, $(C_1-C_{10})$heteroaryl, $(C_3-C_{10})$cycloalkyl, and phenyl substituents may optionally be substituted with one to three moieties independently selected from halo, $(C_1-C_6)$alkyl, and $(C_1-C_6)$alkoxy.

Another more specific embodiment of the $(R^9)_m$—$(C_1-C_6)$alkyl group of compounds of the present invention includes those compounds of formula I wherein $R^4$ is $(R^9)_m$—$(C_1)$alkyl; m is 1; $R^9$ is selected from the group consisting of $(R^{11})_2$N—, $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, $R^{11}$—(C=O)—, $(R^{11}$—O—(C=O)—, $(R^{11})$-[N(R$^{10}$)]—(C=O)—, $R^{11}$—O—, $R^{11}$—(C=O)—O—, $R^{11}$—O—(C=O)—O— and $(R^{11})$—[N(R$^{10}$)]—(C=O)—O—; and $R^{11}$ is hydrogen, $R^{12}$—$(C_1-C_6)$alkyl, $(C_3-C_6)$alkenyl, and $(C_3-C_6)$alkynyl.

Another more specific embodiment of the $(R^9)_m$—$(C_1-C_6)$alkyl group of compounds of the present invention includes those compounds of formula I wherein $R^4$ is $(R^9)_m$—$(C_1)$alkyl; m is 1; $R^9$ is selected from the group consisting of $(R^{11})_2$N—, $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, $R^{11}$—(C=O)—, $R^{11}$—O—(C=O)—, $(R^{11})$—[N(R$^{10}$)]—(C=O)—, $R^{11}$—O—, $R^{11}$—(C=O)—O—, $R^{11}$—O—(C=O)—O— and $(R^{11})$—[N(R$^{10}$)]—(C=O)—O—; and $R^{11}$ is selected from the group selected from $(C_1-C_{10})$heterocyclic, $(C_1-C_{10})$heteroaryl, $(C_3-C_{10})$cycloalkyl, and phenyl; wherein each of the aforesaid $(C_1-C_{10})$heterocyclic, $(C_1-C_{10})$heteroaryl, $(C_3-C_{10})$cycloalkyl, and phenyl substituents may optionally be substituted with one to three moieties independently selected from halo, $(C_1-C_6)$alkyl, and $(C_1-C_6)$alkoxy.

Another more specific embodiment of the $(R^9)_m$—$(C_1-C_6)$alkyl group of compounds of the present invention includes those compounds of formula I wherein $R^4$ is $(R^9)_m$—$(C_1)$alkyl; m is 1; $R^9$ is selected from the group consisting of $R^{11}$—(C=O)—[N($R^{10}$)]—, ($R^{11}$)—[N($R^{10}$)]—(C=O)—[N($R^{10}$)]—, $R^{11}$—O—(C=O)—[N($R^{10}$)]—, $R^{11}$—(C=O)—, $R^{11}$—O—(C=O)—, ($R^{11}$)—[N($R^{10}$)]—(C=O)—, $R^{11}$—O—, $R^{11}$—(C=O)—O—, $R^{11}$—O—(C=O)—O— and ($R^{11}$)—[N($R^{10}$)]—(C=O)—O—; and $R^{11}$ is selected from the group consisting of hydrogen, $R^{12}$—$(C_1-C_6)$alkyl and $(C_1-C_{10})$heteroaryl; wherein each of the aforesaid $(C_1-C_6)$alkyl and $(C_1-C_{10})$heteroaryl substituents may optionally be substituted with one to three moieties independently selected from halo, $(C_1-C_6)$alkyl, and $(C_1-C_6)$alkoxy.

Another embodiment of the present invention includes those compounds of formula I wherein $R^4$ is $(R^9)_m$—$(C_1-C_6)$alkenyl.

Another embodiment of the present invention includes those compounds of formula I wherein $R^4$ is $(R^9)_m$-phenyl, $(R^9)_m$—$(C_1-C_{10})$heteroaryl, $(R^9)_m$—$(C_1-C_{10})$heterocyclic or $(R^9)_m$—$(C_3-C_{10})$cycloalkyl.

Another embodiment of the present invention includes those compounds of formula I wherein $R^3$ is $R^5$—$(NR^6)$—.

Another embodiment of the present invention includes those compounds of formula I wherein $R^3$ is $R^5$—S—.

Another embodiment of the present invention includes those compounds of formula I wherein $R^3$ is $R^5$—(S=O)—.

Another embodiment of the present invention includes those compounds of formula I wherein $R^3$ is $R^5$—$(SO_2)$—.

Another embodiment of the present invention includes those compounds of formula I wherein $R^3$ is $R^5$—$SO_2$—$NR^6$—.

Another embodiment of the present invention includes those compounds of formula I wherein $R^3$ is $R^5$—$(NR^6)$—$SO_2$—.

Another embodiment of the present invention includes those compounds of formula I wherein $R^3$ is $R^5$—O—.

Another embodiment of the present invention includes those compounds of formula I wherein $R^3$ is $R^5$—(C=O)—.

Another embodiment of the present invention includes those compounds of formula I wherein $R^3$ is $R^5$—$(NR^6)$—(C=O)—.

Another embodiment of the present invention includes those compounds of formula I wherein $R^3$ is $R^5$—(C=O)—$NR^6$—.

Another embodiment of the present invention includes those compounds of formula I wherein $R^3$ is $R^5$—O—(C=O)—.

Another embodiment of the present invention includes those compounds of formula I wherein $R^3$ is $R^5$—(C=O)—O—.

Another embodiment of the present invention includes those compounds of formula I wherein $R^3$ is $R^5$—$CR^7$=$CR^8$—.

Another embodiment of the present invention includes those compounds of formula I wherein $R^3$ is $R^5$—C≡C—.

More specific embodiments of each of the aforesaid $R^5$ containing $R^3$ embodiments of the present invention includes those compounds of formula I wherein $R^5$ is hydrogen.

Other more specific embodiments of each of the aforesaid $R^5$ containing $R^3$ embodiments of the present invention includes those compounds of formula I wherein $R^5$ is $(R^9)_m$—$(C_1-C_6)$alkyl, $(R^9)_m$—$(C_2-C_6)$alkenyl, $(R^9)_m$—$(C_2-C_6)$alkynyl or perhalo$(C_1-C_6)$alkyl; and m is an integer from one to three.

Other more specific embodiments of each of the aforesaid $R^5$ containing $R^3$ embodiments of the present invention includes those compounds of formula I wherein $R^5$ is $(R^9)_m$-phenyl, $(R^9)_m$—$(C_1-C_{10})$heteroaryl, $(R^9)_m$—$(C_1-C_{10})$heterocyclic or $(R^9)_m$—$(C_3-C_{10})$cycloalkyl; and m is one.

Other more specific embodiments of each of the aforesaid $R^5$ containing $R^3$ embodiments of the present invention includes those compounds of formula I wherein $R^5$ is $(R^9)_m$-phenyl, $(R^9)_m$—$(C_1-C_{10})$heteroaryl, $(R^9)_m$—$(C_1-C_{10})$heterocyclic, $(R^9)_m$—$(C_3-C_{10})$cycloalkyl;

m is one; and wherein when $R^9$ is a substituent on a carbon atom each $R^9$ is independently selected from the group consisting of hydrogen, halo, $R^{11}$—$(C_1-C_6)$alkyl, perhalo$(C_1-C_6)$alkyl, $(C_1-C_6)$alkyl-S—, $(C_1-C_6)$alkyl-$SO_2$—, $R^{11}$—[N($R^{10}$)]—$SO_2$—, $(R^{11})_2$N—, $R^{11}$—$SO_2$—[N($R^{10}$)]—, $R^{11}$—(C=O)—[N($R^{10}$)]—, ($R^{11}$)—[N($R^{10}$)]—(C=O)—[N($R^{10}$)]—, $R^{11}$—O—(C=O)—[N($R^{10}$)]—, —C≡N, $R^{11}$—(C=O)—, $R^{11}$—O—(C=O)—, ($R^{11}$)—[N($R^{10}$)]—(C=O)—, $R^{11}$—O—, perhalo$(C_1-C_6)$alkoxy, $R^{11}$—(C=O)—O—, $R^{11}$—O—(C=O)—O— and ($R^{11}$)-[N($R^{10}$)]—(C=O)—O—;

wherein when $R^9$ is a substituent on a nitrogen atom each $R^9$ is independently selected from the group consisting of hydrogen, $R^{11}$—$(C_1-C_6)$alkyl, perhalo$(C_1-C_6)$alkyl, $(C_1-C_6)$alkyl-$SO_2$—, $R^{11}$—[N($R^{10}$)]—$SO_2$—, $R^{11}$—(C=O)—, $R^{11}$—O—(C=O)—, and ($R^{11}$)—[N($R^{10}$)]—(C=O)—.

Other more specific embodiments of each of the aforesaid $R^5$ containing $R^3$ embodiments of the present invention includes those compounds of formula I wherein $R^5$ is $(R^9)_m$-phenyl, $(R^9)_m$—$(C_1-C_{10})$heteroaryl, $(R^9)_m$-$(C_1-C_{10})$heterocyclic, $(R^9)$, —$(C_3-C_{10})$cycloalkyl;

m is one;

wherein when $R^9$ is a substituent on a carbon atom each $R^9$ is independently selected from the group consisting of hydrogen, halo, $R^{11}$—$(C_1-C_6)$alkyl, perhalo$(C_1-C_6)$alkyl, $(C_1-C_6)$alkyl-S—, $(C_1-C_6)$alkyl-$SO_2$—, $R^{11}$—[N($R^{10}$)]—$SO_2$—, $(R^{11})_2$N—, $R^{11}$—$SO_2$—[N($R^{10}$)]—, $R^{11}$—(C=O)—[N($R^{10}$)]—, ($R^{11}$)—[N($R^{10}$)]—(C=O)—[N($R^{10}$)]—, $R^{11}$—O—(C=O)—[N($R^{10}$)]—, —C≡N, $R^{11}$—(C=O)—, $R^{11}$—O—(C=O)—, ($R^{11}$)—[N($R^{10}$)]—(C=O)—, $R^{11}$—O—, perhalo$(C_1-C_6)$alkoxy, $R^{11}$—(C=O)—O—, $R^{11}$—O—(C=O)—O— and ($R^{11}$)—[N($R^{10}$)]—(C=O)—O—;

wherein when $R^9$ is a substituent on a nitrogen atom each $R^9$ is independently selected from the group consisting of hydrogen, $R^{11}$—$(C_1-C_6)$alkyl, perhalo$(C_1-C_6)$alkyl, $(C_1-C_6)$alkyl-$SO_2$—, $R^{11}$—[N($R^{10}$)]—$SO_2$—, $R^{11}$—(C=O)—, $R^{11}$—O—(C=O)—, and ($R^{11}$)—[N($R^{10}$)]—(C=O)—; and $R^{11}$ is hydrogen.

Other more specific embodiments of each of the aforesaid $R^5$ containing $R^3$ embodiments of the present invention includes those compounds of formula I wherein $R^5$ is $(R^9)_m$-phenyl, $(R^9)_m$—$(C_1-C_{10})$heteroaryl, $(R^9)_m$—$(C_1-C_{10})$heterocyclic, $(R^9)$, —$(C_3-C_{10})$cycloalkyl;

m is one;

wherein when $R^9$ is a substituent on a carbon atom each $R^9$ is independently selected from the group consisting of hydrogen, halo, $R^{11}$—$(C_1-C_6)$alkyl, perhalo$(C_1-C_6)$alkyl, $(C_1-C_6)$alkyl-S—, $(C_1-C_6)$alkyl-SO$_2$—, $R^{11}$—[N($R^{10}$)]—SO$_2$—, $(R^{11})_2$N—, $R^{11}$—SO$_2$—[N($R^{10}$)]—, $R^{11}$—(C=O)—[N($R^{10}$)]—, $(R^{11})$—[N($R^{10}$)]—(C=O)—[N($R^{10}$)]—, $R^{11}$—O—(C=O)—[N($R^{10}$)]—, —C≡N, $R^{11}$—(C=O)—, $R^{11}$—O—(C=O)—, $(R^{11})$—[N($R^{10}$)]—(C=O)—, $R^{11}$—O—, perhalo($C_1$-$C_6$)alkoxy, $R^{11}$—(C=O)—O—, $R^{11}$—O—(C=O)—O— and $(R^{11})$—[N($R^{10}$)]—(C=O)—O—;

wherein when $R^9$ is a substituent on a nitrogen atom each $R^9$ is independently selected from the group consisting of hydrogen, $R^{11}$—(C$_1$-C$_6$)alkyl, perhalo(C$_1$-C$_6$)alkyl, (C$_1$-C$_6$)alkyl-SO$_2$—, $R^{11}$—[N($R^{10}$)]—SO$_2$—, $R^{11}$—(C=O)—, $R^{11}$—O—(C=O)—, and $(R^{11})$—[N($R^{10}$)]—(C=O)—; and $R^{11}$ is (C$_1$-C$_6$)alkyl optionally substituted with one to three substituents independently selected from halo, (C$_1$-C$_6$)alkyl, and (C$_1$-C$_6$)alkoxy;

Other more specific embodiments of each of the aforesaid $R^5$ containing $R^3$ embodiments of the present invention includes those compounds of formula I wherein $R^5$ is $(R^9)_m$-phenyl, $(R^9)_m$—(C$_1$-C$_{10}$)heteroaryl, $(R^9)_m$—(C$_1$-C$_{10}$)heterocyclic, $(R^9)_m$—(C$_3$-C$_{10}$)cycloalkyl;

m is one;

wherein when $R^9$ is a substituent on a carbon atom each $R^9$ is independently selected from the group consisting of hydrogen, halo, $R^{11}$—(C$_1$-C$_6$)alkyl, perhalo(C$_1$-C$_6$)alkyl, (C$_1$-C$_6$)alkyl-S—, (C$_1$-C$_6$)alkyl-SO$_2$—, $R^{11}$—[N($R^{10}$)]—SO$_2$—, $(R^{11})_2$N—, $R^{11}$—SO$_2$—[N($R^{10}$)]—, $R^{11}$—(C=O)—[N($R^{10}$)]—, $(R^{11})$—[N($R^{10}$)]—(C=O)—[N($R^{10}$)]—, $R^{11}$—O—(C=O)—[N($R^{10}$)]—, —C≡N, $R^{11}$—(C=O)—, $R^{11}$—O—(C=O)—, $(R^{11})$—[N($R^{10}$)]—(C=O)—, $R^{11}$—O—, perhalo(C$_1$-C$_6$)alkoxy, $R^{11}$—(C=O)—O—, $R^{11}$—O—(C=O)—O— and $(R^{11})$—[N($R^{10}$)]—(C=O)—O—;

wherein when $R^9$ is a substituent on a nitrogen atom each $R^9$ is independently selected from the group consisting of hydrogen, $R^{11}$—(C$_1$-C$_6$)alkyl, perhalo(C$_1$-C$_6$)alkyl, (C$_1$-C$_6$)alkyl-SO$_2$—, $R^{11}$—[N($R^{10}$)]—SO$_2$—, $R^{11}$—(C=O)—, $R^{11}$—O—(C=O)—, and $(R^{11})$—[N($R^{10}$)]—(C=O)—; and $R^{11}$ is selected from the group consisting of (C$_1$-C$_{10}$)heterocyclic, (C$_1$-C$_{10}$)heteroaryl, (C$_3$-C$_{10}$)cycloalkyl, and phenyl; wherein each of the aforesaid (C$_1$-C$_{10}$)heterocyclic, (C$_1$-C$_{10}$)heteroaryl, (C$_3$-C$_{10}$)cycloalkyl, and phenyl substituents may optionally be substituted with one to three moieties independently selected from halo, (C$_1$-C$_6$)alkyl, and (C$_1$-C$_6$)alkoxy.

Another embodiment of the present invention includes those compounds of formula I wherein X is >C($R^{14}$)$_2$. Other embodiments of the present invention include those compounds of formula I wherein X is >C($R^{14}$)$_2$. in combination with the each of the aforesaid embodiments of $R^3$ (e.g., X is >C($R^{14}$)$_2$ and $R^3$ is $R^4$ and $R^4$ is hydrogen, halo, —C≡N or perhalo(C$_1$-C$_6$)alkyl or X is >C($R^{14}$)$_2$ and $R^3$ is $R^4$ and $R^4$ is $(R^9)_m$—(C$_1$-C$_6$)alkyl; or X is >C($R^{14}$)$_2$ and $R^3$ is $R^4$ and $R^4$ is $(R^9)_m$—(C$_1$-C$_6$)alkenyl; or X is >C($R^{14}$)$_2$ and $R^3$ is $R^4$ and $R^4$ is $(R^9)_m$-phenyl, $(R^9)_m$—(C$_1$-C$_{10}$)heteroaryl, $(R^9)_m$—(C$_1$-C$_{10}$)heterocyclic, or $(R^9)_m$—(C$_3$-C$_{10}$)cycloalkyl; or X is >C($R^{14}$)$_2$ and $R^3$ is $R^5$—(NR$^6$)—; or X is >C($R^{14}$)$_2$ and $R^3$ is $R^5$—S—; or X is >C($R^{14}$)$_2$ and $R^3$ is $R^5$—(S=O)—; or X is >C($R^{14}$)$_2$ and $R^3$ is $R^5$—(SO$_2$)—; or X is >C($R^{14}$)$_2$ and $R^3$ is $R^5$—SO$_2$—NR$^6$—; or X is >C($R^{14}$)$_2$ and $R^3$ is $R^5$—(NR$^6$)—SO$_2$—; or X is >C($R^{14}$)$_2$ and $R^3$ is $R^5$—O—; or X is >C($R^{14}$)$_2$ and $R^3$ is $R^5$—(C=O)—; or X is >C($R^{14}$)$_2$ and $R^3$ is $R^5$—(NR$^6$)—(C=O)—; or X is >C($R^{14}$)$_2$ and $R^3$ is $R^5$—(C=O)—NR$^6$—; or X is >C($R^{14}$)$_2$ and $R^3$ is $R^5$—O—(C=O)—; or X is >C($R^{14}$)$_2$ and $R^3$ is $R^5$—(C=O)—O—; or X is >C($R^{14}$)$_2$ and $R^3$ is $R^5$—CR$^7$=CR$^8$—; or X is >C($R^{14}$)$_2$ and $R^3$ is $R^5$—C≡C—).

Another embodiment of the present invention includes those compounds of formula I wherein X is >NR$^{15}$. Other embodiments of the present invention include those compounds of formula I wherein X is >NR$^{15}$ in combination with the each of the aforesaid embodiments of $R^3$ (e.g., X is >NR$^{15}$ and $R^3$ is $R^4$ and $R^4$ is hydrogen, halo, —C≡N or perhalo(C$_1$-C$_6$)alkyl or X is >NR$^{15}$ and $R^3$ is $R^4$ and $R^4$ is $(R^9)_m$—(C$_1$-C$_6$)alkyl; or X is >NR$^{15}$ and $R^3$ is $R^4$ and $R^4$ is $(R^9)_m$—(C$_1$-C$_6$)alkenyl; or X is >NR$^{15}$ and $R^3$ is $R^4$ and $R^4$ is $(R^9)_m$-phenyl, $(R^9)_m$—(C$_1$-C$_{10}$)heteroaryl, $(R^9)_m$—(C$_1$-C$_{10}$)heterocyclic, or $(R^9)_m$—(C$_3$-C$_{10}$)cycloalkyl; or X is >NR$^{15}$ and $R^3$ is $R^5$—(NR$^6$)—; or X is >NR$^{15}$ and $R^3$ is $R^5$—S—; or X is >NR$^{15}$ and $R^3$ is $R^5$—(S=O)—; or X is >NR$^{15}$ and $R^3$ is $R^5$—(SO$_2$)—; or X is >NR$^{15}$ and $R^3$ is $R^5$—SO$_2$—NR$^6$—; or X is >NR$^{15}$ and $R^3$ is $R^5$—(NR$^6$)—SO$_2$—; or X is >NR$^{15}$ and $R^3$ is $R^5$—O—; or X is >NR$^{15}$ and $R^3$ is $R^5$—(C=O)—; or X is >NR$^{15}$ and $R^3$ is $R^5$—(NR$^6$)—(C=O)—; or X is >NR$^{15}$ and $R^3$ is $R^5$—(C=O)—NR$^6$—; or X is >NR$^{15}$ and $R^3$ is $R^5$—O—(C=O)—; or X is >NR$^{15}$ and $R^3$ is $R^5$—(C=O)—O—; or X is >NR$^{15}$ and $R^3$ is $R^5$—CR$^7$=CR$^8$—; or X is >NR$^{15}$ and $R^3$ is $R^5$—C≡C—).

Another embodiment of the present invention includes those compounds of formula I wherein X is —S—. Other embodiments of the present invention include those compounds of formula I wherein X is >NR$^{15}$ in combination with the each of the aforesaid embodiments of $R^3$.

Another embodiment of the present invention includes those compounds of formula I wherein X is >S=O. Other embodiments of the present invention include those compounds of formula I wherein X is >NR$^{15}$ in combination with the each of the aforesaid embodiments of $R^3$.

Another embodiment of the present invention includes those compounds of formula I wherein X is >SO$_2$. Other embodiments of the present invention include those compounds of formula I wherein X is >NR$^{15}$ in combination with the each of the aforesaid embodiments of $R^3$.

Another embodiment of the present invention includes those compounds of formula I wherein X is —O—. Other embodiments of the present invention include those compounds of formula I wherein X is >NR$^{15}$ in combination with the each of the aforesaid embodiments of $R^3$.

Another embodiment of the present invention includes those compounds of formula I wherein $R^1$ is optionally substituted (C$_1$-C$_6$)alkyl, phenyl, (C$_3$-C$_{10}$)cycloalkyl, (C$_1$-C$_{10}$)heteroaryl or (C$_1$-C$_{10}$)heterocyclic. Other embodiments of the present invention includes those compounds of formula I wherein $R^1$ is optionally substituted (C$_1$-C$_6$)alkyl, phenyl, (C$_3$-C$_{10}$)cycloalkyl, (C$_1$-C$_{10}$)heteroaryl or (C$_1$-C$_{10}$)heterocyclic in combination with the each of the aforesaid embodiments of X (e.g., X is —O— and $R^1$ is (C$_1$-C$_6$)alkyl, phenyl, (C$_3$-C$_{10}$)cycloalkyl, (C$_1$-C$_{10}$)heteroaryl or (C$_1$-C$_{10}$)heterocyclic or X is >C($R^{14}$)$_2$ and $R^1$ is (C$_1$-C$_6$)alkyl, phenyl, (C$_3$-C$_{10}$)cycloalkyl, (C$_1$-C$_{10}$)heteroaryl or (C$_1$-C$_{10}$)heterocyclic)). Other embodiments of the present invention include those compounds of formula I wherein $R^1$ is optionally substituted (C$_1$-C$_6$)alkyl, phenyl, (C$_3$-C$_{10}$)cycloalkyl, (C$_1$-C$_{10}$)heteroaryl or (C$_1$-C$_{10}$)heterocyclic in combination with the each of the aforesaid embodiments of $R^3$ (e.g., $R^1$ is (C$_1$-C$_6$)alkyl, phenyl, (C$_3$-C$_{10}$)cycloalkyl, (C$_1$-C$_{10}$)heteroaryl or (C$_1$-C$_{10}$)heterocyclic and $R^3$ is $R^4$ and $R^4$ is hydrogen, halo, —C≡N or perhalo(C$_1$-C$_6$)alkyl or $R^1$ is (C$_1$-C$_6$)alkyl, phenyl, (C$_3$-C$_{10}$)cycloalkyl, (C$_1$-C$_{10}$)heteroaryl or (C$_1$-C$_{10}$)heterocyclic and $R^3$ is $R^4$ and $R^4$ is $(R^9)_m$—(C$_1$-C$_6$)alkyl)). Still other embodiments of the present invention include those compounds of formula I wherein $R^1$ is (C$_1$-C$_6$)alkyl, phenyl, (C$_3$-C$_{10}$)cycloalkyl, (C$_1$-C$_{10}$)heteroaryl or (C$_1$-C$_{10}$)heterocyclic in combination with the each of the aforesaid embodiments of $R^3$ and each of the aforesaid embodiments of X (e.g., $R^1$ is $(C_1-C_6)$alkyl, phenyl, $(C_3-C_{10})$cycloalkyl, $(C_1-C_{10})$heteroaryl or $(C_1-C_{10})$ heterocyclic; X is $>C(R^{14})_2$, and $R^3$ is $R^4$ and $R^4$ is hydrogen, halo, —C≡N or perhalo($C_1-C_6$)alkyl; or $R^1$ is $(C_1-C_6)$alkyl, phenyl, $(C_3-C_{10})$cycloalkyl, $(C_1-C_{10})$heteroaryl or $(C_1-C_{10})$ heterocyclic; X is —O—, and $R^3$ is $R^4$ and $R^4$ is $(R^9)_m$—$(C_1-C_6)$alkyl)).

A more specific embodiment of the substituted $(C_1-C_6)$ alkyl group of compounds of the present invention includes those compounds of formula I wherein $R^1$ is $(C_1-C_6)$alkyl, optionally substituted with one to four groups independently selected from halo, hydroxy, $(C_1-C_6)$alkyl, $(C_2-C_6)$alkenyl, $(C_2-C_6)$alkynyl, $(C_1-C_6)$alkoxy, perhalo$(C_1-C_6)$alkyl, perhalo$(C_1-C_6)$alkoxy, —C≡N, —NO$_2$, amino, $(C_1-C_6)$alkylamino, $[(C_1-C_6)$alkyl]$_2$-amino, HO—(C=O)—, $(C_1-C_6)$ alkyl-(C=O)—, $(C_1-C_6)$alkyl-O—(C=O)—, $(C_1-C_6)$alkyl-CO$_2$—, $(C_1-C_6)$alkyl-(C=O)—NH—, $(C_1-C_6)$alkyl-NH—(C=O)—, $(C_1-C_6)$alkyl-(C=O)—$[((C_1-C_6)$alkyl)—N]—, $(C_1-C_6)$alkyl-$[((C_1-C_6)$alkyl)—N]—(C=O)—, $(C_1-C_6)$ alkyl-SO$_2$NH—, $(C_1-C_6)$alkyl-SO$_2$—, optionally substituted phenyl-(C=O)—, optionally substituted phenyl-(C=O)—O—, optionally substituted phenoxy, optionally substituted phenyl-NH—(C=O)—, optionally substituted phenyl-$[((C_1-C_6)$alkyl)—N]—(C=O)—, optionally substituted phenyl-(C=O)—NH— and optionally substituted phenyl-(C=O)—$[((C_1-C_6)$alkyl)—N]—. A more preferred embodiment of the present invention includes those compounds of formula I wherein $R^1$ is $(C_1-C_4)$alkyl.

Another embodiment of the present invention includes those compounds of formula I wherein $R^1$ is optionally substituted $(C_1-C_4)$alkyl in combination with the each of the aforesaid embodiments of X (e.g., X is —O— and $R^1$ is the aforesaid optionally substituted $(C_1-C_4)$alkyl or X is $>C(R^{14})_2$ and $R^1$ is the aforesaid optionally substituted $(C_1-C_4)$alkyl). Other embodiments of the present invention include those compounds of formula I wherein $R^1$ is optionally substituted $(C_1-C_4)$alkyl in combination with the each of the aforesaid embodiments of $R^3$. Still other embodiments of the present invention include those compounds of formula I wherein $R^1$ is $(C_1-C_4)$alkyl in combination with the each of the aforesaid embodiments of $R^3$ and each of the aforesaid embodiments of X.

Another embodiment of the present invention includes those compounds of formula I wherein $R^1$ is optionally substituted $(C_3-C_6)$cycloalkyl.

Other embodiments of the present invention includes those compounds of formula I wherein $R^1$ is optionally substituted $(C_3-C_6)$cycloalkyl in combination with the each of the aforesaid embodiments of X. Other embodiments of the present invention include those compounds of formula I wherein $R^1$ is optionally substituted $(C_3-C_6)$cycloalkyl in combination with the each of the aforesaid embodiments of $R^3$. Still other embodiments of the present invention include those compounds of formula I wherein $R^1$ is $(C_3-C_6)$cycloalkyl in combination with the each of the aforesaid embodiments of $R^3$ and each of the aforesaid embodiments of X.

Another embodiment of the present invention includes those compounds of formula I wherein $R^1$ is optionally substituted phenyl; more specifically wherein said substituents are independently selected from the group consisting of halo, $(C_1-C_6)$alkyl, $(C_2-C_6)$alkenyl, $(C_2-C_6)$alkynyl, perhalo $(C_1-C_6)$alkyl, phenyl, $(C_3-C_{10})$cycloalkyl, $(C_1-C_{10})$heteroaryl, $(C_1-C_{10})$heterocyclic, formyl, —C≡N, $(C_1-C_6)$ alkyl-(C=O)—, phenyl-(C=O)—, HO—(C=O)—, $(C_1-C_6)$alkyl-O—(C=O)—, $(C_1-C_6)$alkyl-NH—(C=O)—, $[(C_1-C_6)$alkyl]$_2$—N—(C=O)—, phenyl-NH—(C=O)—, phenyl-$[((C_1-C_6)$alkyl)—N]—(C=O)—, —NO$_2$, amino, $(C_1-C_6)$alkylamino, $[(C_1-C_6)$alkyl]$_2$-amino, $(C_1-C_6)$alkyl-(C=O)—NH—, $(C_1-C_6)$alkyl-(C=O)—$[((C_1-C_6)$alkyl)—N]—, phenyl-(C=O)—NH—, phenyl-(C=O)—$[((C_1-C_6)$alkyl)—N]—, H$_2$N—(C=O)—NH—, $(C_1-C_6)$alkyl-HN—(C=O)—NH—, $[(C_1-C_6)$alkyl]$_2$—N—(C=O)—NH—, $(C_1-C_6)$alkyl-HN—(C=O)—$[((C_1-C_6)$alkyl)—N]—, $[(C_1-C_6)$alkyl]$_2$—N—(C=O)—$[((C_1-C_6)$alkyl)—N]—, phenyl-HN—(C=O)—NH—, (phenyl)$_2$—N—(C=O)—NH—, phenyl-HN—(C=O)—$[((C_1-C_6)$alkyl)—N]—, (phenyl)$_2$—N—(C=O)—$[((C_1-C_6)$alkyl)—N]—, $(C_1-C_6)$alkyl-O—(C=O)—NH—, $(C_1-C_6)$alkyl-O—(C=O)—$[((C_1-C_6)$alkyl)—N]—, phenyl-O—(C=O)—NH—, phenyl-O—(C=O)—$[((C_1-C_6)$alkyl)—N]—, $(C_1-C_6)$alkyl-SO$_2$NH—, phenyl-SO$_2$NH—, $(C_1-C_6)$alkyl-SO$_2$—, phenyl-SO$_2$—, hydroxy, $(C_1-C_6)$alkoxy, perhalo$(C_1-C_6)$alkoxy, phenoxy, $(C_1-C_6)$alkyl-(C=O)—O—, phenyl-(C=O)—O—, H$_2$N—(C=O)—O—, $(C_1-C_6)$alkyl-HN—(C=O)—O—, $[(C_1-C_6)$alkyl]$_2$—N—(C=O)—O—, phenyl-HN—(C=O)—O—, (phenyl)$_2$—N—(C=O)—O—; more specifically wherein each of said moieties containing a phenyl alternative may optionally be substituted by one or two radicals independently selected from the group consisting of $(C_1-C_6)$alkyl, halo, $(C_1-C_6)$alkoxy, perhalo$(C_1-C_6)$alkyl and perhalo$(C_1-C_6)$alkoxy.

Another embodiment of the present invention includes those compounds of formula I wherein $R^1$ is optionally substituted phenyl wherein said substituents are independently selected from the group consisting of halo, $(C_1-C_6)$ alkyl, $(C_2-C_6)$alkenyl, perhalo$(C_1-C_6)$alkyl, —C≡N, $(C_1-C_6)$alkyl-(C=O)—, HO—(C=O)—, $(C_1-C_6)$alkyl-O—(C=O)—, $(C_1-C_6)$alkyl-NH—(C=O)—, $[(C_1-C_6)$alkyl]$_2$—N—(C=O)—, amino, $(C_1-C_6)$alkylamino, $[(C_1-C_6)$alkyl]$_2$-amino, $(C_1-C_6)$alkyl-(C=O)—NH—, $(C_1-C_6)$alkyl-(C=O)—$[((C_1-C_6)$alkyl)—N]—, H$_2$N—(C=O)—NH—, $(C_1-C_6)$alkyl-HN—(C=O)—NH—, $[(C_1-C_6)$alkyl-]$_2$N—(C=O)—NH—, $(C_1-C_6)$alkyl-HN—(C=O)—$[((C_1-C_6)$alkyl)—N]—, $[(C_1-C_6)$alkyl]$_2$—N—(C=O)—$[((C_1-C_6)$alkyl)—N]—, hydroxy, $(C_1-C_6)$alkoxy, perhalo$(C_1-C_6)$alkoxy, $(C_1-C_6)$alkyl-(C=O)—O—, H$_2$N—(C=O)—O—, $(C_1-C_6)$alkyl-HN—(C=O)—O— and $[(C_1-C_6)$alkyl]$_2$—N—(C=O)—O—.

Another embodiment of the present invention includes those compounds of formula I wherein $R^1$ is optionally substituted phenyl containing two adjacent substituents which taken together with the carbon atoms to which they are attached form a five to six membered carbocyclic or heterocyclic ring.

Another embodiment of the present invention includes those compounds of formula I wherein $R^1$ is each of the aforesaid embodiments of optionally substituted phenyl in combination with the each of the aforesaid embodiments of X (e.g., X is —O— and $R^1$ is optionally substituted phenyl containing two adjacent substituents which taken together with the carbon atoms to which they are attached form a five to six membered carbocyclic or heterocyclic ring or X is $>C(R^{14})_2$ and $R^1$ is optionally substituted phenyl containing two adjacent substituents which taken together with the carbon atoms to which they are attached form a five to six membered carbocyclic or heterocyclic ring).

Another embodiment of the present invention includes those compounds of formula I wherein $R^1$ is $(R^{17})_2$—N—, wherein each $R^{17}$ is independently selected from hydrogen, $(C_1-C_6)$alkyl, phenyl, $(C_1-C_{10})$heterocyclic and $(C_3-C_{10})$ cycloalkyl; wherein each of the aforesaid $R^{17}$, $(C_1-C_6)$alkyl, phenyl, $(C_1-C_{10})$heteroaryl, $(C_1-C_{10})$heterocyclic and $(C_3$-

$C_{10}$)cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[(($C_1-C_6$)alkyl)—N]—, phenyl-(C=O)—NH—, phenyl-(C=O)—[(($C_1-C_6$)alkyl)—N]—, —C≡N, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N(C=O)—, $(C_1-C_6)$alkyl-NH—(C=O)—, [$(C_1-C_6)$alkyl]$_2$—N—(C=O)—, phenyl-NH—(C=O)—, phenyl-[(($C_1-C_6$)alkyl)—N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^{17}$ $(C_1-C_6)$alkyl groups may be taken together with the nitrogen atom to form a five to six membered heterocyclic or heteroaryl ring;

Another embodiment of the present invention includes those compounds of formula I wherein $R^1$ is $(R^{17})_2$—N— and wherein each $R^{17}$ is independently selected from hydrogen, $(C_1-C_4)$alkyl, phenyl and $(C_1-C_{10})$heterocyclic.

Another embodiment of the present invention includes those compounds of formula I wherein $R^1$ is $(R^{17})_2$—N— and wherein two $R^2$ $(C_1-C_6)$alkyl groups may be taken together with the nitrogen atom to form a five to six membered heterocyclic or heteroaryl ring.

Another embodiment of the present invention includes those compounds of formula I wherein $R^1$ is each of the aforesaid embodiments of $(R^{17})_2$—N— in combination with the each of the aforesaid embodiments of X (e.g., X is —O— and $R^{17}$ is hydrogen, $(C_1-C_4)$alkyl, phenyl and $(C_1-C_{10})$heterocyclic or X is >C(R$^{14}$)$_2$ and $R^{17}$ is hydrogen, $(C_1-C_4)$alkyl, phenyl and $(C_1-C_{10})$heterocyclic). Other embodiments of the present invention include those compounds of formula I wherein $R^1$ is each of the aforesaid embodiments of $(R^{17})_2$—N— in combination with the each of the aforesaid embodiments of $R^3$. Still other embodiments of the present invention include those compounds of formula I wherein $R^1$ is each of the aforesaid embodiments of $(R^{17})_2$—N— in combination with the each of the aforesaid embodiments of $R^3$ and each of the aforesaid embodiments of X.

Another embodiment of the present invention includes those compounds of formula I wherein s is an integer from one to four and each $R^2$ is independently selected from the group consisting of halo, —C≡N, $(C_1-C_6)$alkyl, $(C_2-C_6)$alkenyl, $(C_2-C_6)$alkynyl and perhalo$(C_1-C_6)$alkyl.

Another embodiment of the present invention includes those compounds of formula I wherein s is an integer from one to four and zero, one or two of $R^2$ are independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, amino, $(C_1-C_6)$alkylamino, [$(C_1-C_6)$alkyl]$_2$-amino, —C≡N, and H$_2$N(C=O)—.

Another embodiment of the present invention includes those compounds of formula I wherein s is an integer from one to three and each $R^2$ is independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, —NO$_2$, amino, $(C_1-C_6)$alkylamino, [$(C_1-C_6)$alkyl]$_2$-amino, —C≡N, and H$_2$N(C=O)—.

Another embodiment of the present invention includes those compounds of formula I wherein s is an integer from one to two and each R is independently selected from the group consisting of halo, $(C_1-C_6)$alkyl, perhalo$(C_1-C_6)$alkyl, $(C_1-C_6)$alkoxy, perhalo$(C_1-C_6)$alkoxy and —C≡N.

Another embodiment of the present invention includes those compounds of formula I wherein s is an integer from one to three and each $R^2$ is independently selected from the group consisting of fluoro, chloro and methyl.

Specific preferred compounds of formula I include the following:

1-Ethyl-3-[2-(3-isopropyl-[1,2,4]triazolo[4,3-a]pyridin-6-ylsulfanyl)-benzyl]-urea;

Ethyl-carbamic acid 2-(3-isopropyl-[1,2,4]triazolo[4,3-a]pyridin-6-ylsulfanyl)-benzyl ester;

[2-(3-Isopropyl-[1,2,4]triazolo[4,3-a]pyridin-6-ylsulfanyl)-benzyl]-carbamic acid ethyl ester;

1-(5-tert-Butyl-2-methyl-2H-pyrazol-3-yl)-3-[2-(3-isopropyl-[1,2,4]triazolo[4,3-a]pyridin-6-ylsulfanyl)-benzyl]-urea;

Ethyl-carbamic acid 2-(3-tert-butyl-[1,2,4]triazolo[4,3-a]pyridin-6-ylsulfanyl)-benzyl ester;

1-(5-tert-Butyl-isoxazol-3-yl)-3-[2-(3-isopropyl-[1,2,4]triazolo[4,3-a]pyridin-6-ylsulfanyl)-benzyl]-urea;

Ethyl-carbamic acid 5-fluoro-2-(3-isopropyl-[1,2,4]triazolo[4,3-a]pyridin-6-ylsulfanyl)-benzyl ester;

Ethyl-carbamic acid 2-fluoro-6-(3-isopropyl-[1,2,4]triazolo[4,3-a]pyridin-6-ylsulfanyl)-benzyl ester; and N-Ethyl-3-[2-(3-isopropyl-[1,2,4]triazolo[4,3-a]pyridin-6-ylsulfanyl)-phenyl]-acrylamide.

Another group of preferred compounds include:

2-[5-Fluoro-2-(3-isopropyl-[1,2,4]triazolo[4,3-a]pyridin-6-ylsulfanyl)-phenyl]-cyclopropanecarboxylic acid ethylamide;

2-[2-(3-tert-Butyl-[1,2,4]triazolo[4,3-a]pyridin-6-ylsulfanyl)-phenyl]-cyclopropanecarboxylic acid ethyl ester;

3-[2-(3-tert-Butyl-[1,2,4]triazolo[4,3-a]pyridin-6-ylsulfanyl)-phenyl]-N-methyl-acrylamide;

3-[2-(3-tert-Butyl-[1,2,4]triazolo[4,3-a]pyridin-6-ylsulfanyl)-phenyl]-N-ethyl-acrylamide;

3-[2-(3-tert-Butyl-[1,2,4]triazolo[4,3-a]pyridin-6-ylsulfanyl)-phenyl]-N-cyclopropyl-acrylamide;

3-[2-(3-tert-Butyl-[1,2,4]triazolo[4,3-a]pyridin-6-ylsulfanyl)-phenyl]-N-(2-hydroxy-ethyl)-acrylamide;

3-[2-(3-tert-Butyl-[1,2,4]triazolo[4,3-a]pyridin-6-ylsulfanyl)-phenyl]-N-cyanomethyl-acrylamide;

3-[2-(3-tert-Butyl-[1,2,4]triazolo[4,3-a]pyridin-6-ylsulfanyl)-phenyl]-N-(2,2,2-trifluoro-ethyl)-acrylamide;

3-[2-(3-tert-Butyl-[1,2,4]triazolo[4,3-a]pyridin-6-ylsulfanyl)-phenyl]-acrylamide;

2-[2-(3-tert-Butyl-[1,2,4]triazolo[4,3-a]pyridin-6-ylsulfanyl)-phenyl]-cyclopropanecarboxylic acid ethylamide;

[2-(3-tert-Butyl-[1,2,4]triazolo[4,3-a]pyridin-6-ylsulfanyl)-5-fluoro-phenyl]-methanol;

3-[2-(3-tert-Butyl-[1,2,4]triazolo[4,3-a]pyridin-6-ylsulfanyl)-5-fluoro-phenyl]-acrylic acid ethyl ester;

3-[2-(3-tert-Butyl-[1,2,4]triazolo[4,3-a]pyridin-6-ylsulfanyl)-5-fluoro-phenyl]-N-ethyl-acrylamide;

2-[2-(3-tert-Butyl-[1,2,4]triazolo[4,3-a]pyridin-6-ylsulfanyl)-5-fluoro-phenyl]-cyclopropanecarboxylic acid ethyl ester;

3-[2-(3-tert-Butyl-[1,2,4]triazolo[4,3-a]pyridin-6-ylsulfanyl)-5-fluoro-phenyl]-acrylamide;

3-[2-(3-tert-Butyl-[1,2,4]triazolo[4,3-a]pyridin-6-ylsulfanyl)-5-fluoro-phenyl]-N-methyl-acrylamide;
3-[2-(3-tert-Butyl-[1,2,4]triazolo[4,3-a]pyridin-6-ylsulfanyl)-5-fluoro-phenyl]-N-(2,2,2-trifluoro-ethyl)-acrylamide; and
3-[2-(3-tert-Butyl-[1,2,4]triazolo[4,3-a]pyridin-6-ylsulfanyl)-5-fluoro-phenyl]-N-cyanomethyl-acrylamide.

Specific species of the invention are each of Examples 1-113. One specific group of compounds of the invention of particular interest include the benzyl-[1,2,4]triazolo[4,3-a] pyridines. Specific species within this group of compounds include each of Examples 1-13.

Another group of compounds of particular interest include the phenylsulfanyl-[1,2,4]triazolo[4,3-a]pyridines. Specific species within this group of compounds include each of Examples 14-107.

Another specific group of compounds of the invention include the phenoxy-[1,2,4] triazolo [4,3-a]pyridines. Specific species within this group of compounds include each of Examples 108-112.

Other compounds of the invention include:
Ethyl-carbamic acid 2-(3-acetyl-1,2,4]triazolo[4,3-a]pyridin-6-ylsulfanyl)-benzyl ester;
Ethyl-carbamic acid 2-[3-(1-hydroxy-1-methyl-ethyl)-[1,2,4]triazolo[4,3-a]pyridin-6-ylsulfanyl]-benzyl ester;
Ethyl-carbamic acid 2-[3-(1-hydroxy-ethyl)-[1,2,4]triazolo[4,3-a]pyridin-6-ylsulfanyl]-benzyl ester;
Furan-2-carboxylic acid 2-(3-isopropyl-[1,2,4]triazolo[4,3-a]pyridin-6-ylsulfanyl)-benzylamide;
But-2-enoic acid 2-(3-isopropyl-[1,2,4]triazolo[4,3-a]pyridin-6-ylsulfanyl)-benzylamide;
Cyclopropanecarboxylic acid 2-(3-isopropyl-[1,2,4]triazolo[4,3-a]pyridin-6-ylsulfanyl)-benzylamide;
2-[2-(3-Isopropyl-[1,2,4]triazolo[4,3-a]pyridin-6-ylsulfanyl)-phenyl]-cyclopropane-carboxylic acid ethyl ester;
2-[2-(3-Isopropyl-[1,2,4]triazolo[4,3-a]pyridin-6-ylsulfanyl)-phenyl]-cyclopropane-carboxylic acid ethylamide;
Cyclobutanecarboxylic acid 2-(3-isopropyl-[1,2,4]triazolo[4,3-a]pyridin-6-ylsulfanyl)-benzylamide;
2-Methyl-cyclopropanecarboxylic acid 2-(3-isopropyl-[1,2,4]triazolo[4,3-a]pyridin-6-ylsulfanyl)-benzylamide;
N-[2-(3-tert-Butyl-[1,2,4]triazolo[4,3-a]pyridin-6-ylsulfanyl)-phenyl]-butyramide;
3-[2-(3-tert-Butyl-[1,2,4]triazolo[4,3-a]pyridin-6-ylsulfanyl)-phenylsulfanyl]-N-methyl-propionamide;
3-[2-(3-tert-Butyl-[1,2,4]triazolo[4,3-a]pyridin-6-ylsulfanyl)-benzenesulfinyl]-N-methyl-propionamide;
3-[2-(3-tert-Butyl-[1,2,4]triazolo[4,3-a]pyridin-6-ylsulfanyl)-benzenesulfonyl]-N-methyl-propionamide;
Propane-1-sulfonic acid [2-(3-tert-butyl-[1,2,4]triazolo[4,3-a]pyridin-6-ylsulfanyl)-phenyl]-amide;
2-(3-tert-Butyl-[1,2,4]triazolo[4,3-a]pyridin-6-ylsulfanyl)-N-propyl-benzenesulfonamide;
2-(3-tert-Butyl-[1,2,4]triazolo[4,3-a]pyridin-6-ylsulfanyl)-N-propyl-benzamide;
2-(3-tert-Butyl-[1,2,4]triazolo[4,3-a]pyridin-6-ylsulfanyl)-benzoic acid propyl ester;
3-[2-(3-tert-Butyl-[1,2,4]triazolo[4,3-a]pyridin-6-ylsulfanyl)-phenyl]-prop-2-ynoic acid ethylamide; and
3-[2-(3-tert-Butyl-[1,2,4]triazolo[4,3-a]pyridin-6-ylsulfanyl)-3,5-difluoro-phenyl]-N-ethyl-acrylamide.

The present invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

Compounds of Formula (I) are capable of inhibiting proinflammatory cytokines, such as IL-1, IL-6, IL-8, IL-18 and TNF and are therefore of use in therapy. IL-1, IL-6, IL-8, IL-18 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine mediated disease which comprises administering an effective cytokine-interfering amount of a compound of Formula (I) or a pharmaceutically acceptable salt thereof.

Certain compounds of Formula (I) are capable of inhibiting inducible pro-inflammatory proteins, such as COX-2, also referred to by many other names such as prostaglandin endoperoxide synthase-2 (PGHS-2) and are therefore of use in therapy. These proinflammatory lipid mediators of the cyclooxygenase (COX) pathway are produced by the inducible COX-2 enzyme. Regulation, therefore of COX-2 which is responsible for these products derived from arachidonic acid, such as prostaglandins, affect a wide variety of cells and tissues. Expression of COX-1 is not effected by compounds of Formula (I). This selective inhibition of COX-2 is accepted as alleviating or sparing ulcerogenic liability associated with inhibition of COX-1 thereby inhibiting prostaglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management, therefore, includes treatment of neuromuscular pain, headache, cancer pain, and arthritis pain.

Compounds of Formula (I), or a pharmaceutically acceptable salt thereof, are of use in therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of treatment in a human, or other mammal, by inhibition of the synthesis of the COX-2 enzyme.

In particular, compounds of Formula (I) or a pharmaceutically acceptable salt thereof are of use in the therapy of any disease state in a human, or other mammal, which is exacerbated by or caused by excessive or unregulated IL-1, IL-8, IL-18 or TNF production by such mammal's cells, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

Use of a p38 inhibitor for the treatment of p38 mediated disease states, can include, but is not limited to neurodegenerative diseases, such as Alzheimer's disease, Parkinson's disease and multiple sclerosis, etc. In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic obstructive pulmonary disease, chronic pulmonary inflammatory disease, silicosis, pulmonary sarcoidosis, bone resorption diseases, such as osteoporosis, cardiac, brain and renal reperfusion injury, graft vs. host reaction, allograft rejections, fever and myalgias due to infection, such as influenza, (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment of topical disease states mediated by or exacerbated by excessive cytokine production, such as by IL-1, IL-18 or TNF respectively, such as inflamed joints, eczema, contact dermatitis psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence, the use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering, to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit a cytokine, in particular IL-1, IL-6, IL-8, IL-18 or TNF, production such that it is regulated down to normal levels, or in some case to subnormal levels, so as to ameliorate or prevent the disease state. Abnormal levels of IL-1, IL-6, IL-8, IL-18 or TNF, for instance in the context of the present invention, constitute: (i) levels of free (not cell bound) IL-1, IL-6, IL-8, IL-18 or TNF greater than or equal to 1 picogram per ml; (ii) any cell associated IL-1, IL-6, IL-8, IL-18 or TNF; or (iii) the presence of IL-1, IL-6, IL-8, IL-18 or TNF mRNA above basal levels in cells or tissues in which IL-1, IL-6, IL-8, IL-18 or TNF, respectively, is produced.

The discovery that the compounds of Formula (I) are inhibitors of cytokines, specifically IL-1. IL-6, IL-8, IL-18 and TNF is based upon the effects of the compounds of Formula (I) on the production of the IL-1, IL-8 and TNF in in vitro assays which are described herein or are well known to those skilled in the art.

As used herein, the term "inhibiting the production of IL-1 (IL-6, IL-8, IL-18 or TNF)" refers to:

a) a decrease of excessive in vivo levels of the cytokine (IL-1, IL-6, IL-8, IL-18 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8, IL-18 or TNF) in a human to normal or sub-normal levels;

c) a down regulation, by inhibition of the direct synthesis of the cytokine (IL-1, IL-6, IL-8, IL-18 or TNF) or as a postranslational event to normal or sub-normal levels; or d) a down regulation, at the translational level, of excessive in vivo levels of the cytokine (IL-1, IL-6, IL-8, IL-18 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6, IL-8, or IL-18. A disease state in which, for instance, IL-1 is a major component, and whose production or action, is exacerbated or secreted in response to TNF, would therefore be considered a disease state mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to Interleukin-1 (IL-1), Interleukin-6 (IL-6), Interleukin-8 (IL-8), Interleukin-18 (IL-18), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the treatment of a disease state which is exacerbated by, or caused by, excessive or unregulated cytokine production.

As used herein, the cytokine referred to in the phrase "inhibition of a cytokine for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A relatively new member of the MAP kinase family, alternatively termed MAPK14, CSBP, p38 or RK, has been identified by several laboratories [See Lee et al., *Nature*, Vol. 300, n(72), 739-746 (1994)]. Activation of this protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the, present invention, compounds of Formula (I) have been determined to be potent and selective inhibitors of CSBP/p38/RK kinase activity, These inhibitors are of aid in determining the signaling pathways involvement in inflammatory responses. In particular, a definitive signal transduction pathway can be prescribed to the action of lipopolysaccharide in cytokine production in macrophages. In addition to those diseases already noted herein, treatment of stroke, neurotrauma/CNS head injury, cardiac, brain and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors may be tested in a number of animal models for anti-inflammatory activity. Model systems can be chosen that are relatively insensitive to cyclooxygenase inhibitors in order to reveal the unique activities of cytokine suppressive agents. Additionally, the cytokine inhibitors of the present invention are effective in the collagen-induced arthritis model and inhibition of TNF production in the endotoxic shock model. Also of great importance are the compound's effectiveness in inhibiting bone resorption in a rat fetal long bone organ culture system. Griswold et al., (1988) *Arthritis Rheum.* 31:1406-1412; Badger, et al., (1989) *Circ. Shock* 27, 51-61, Votta et al., (1994) *in vitro. Bone* 15, 533-538; Lee et al., (1993.). *B Ann. N.Y. Acad. Sci.* 696, 149-170.

It is also recognized that both IL-6 and IL-8 are produced during rhinovirus (HRV) infections and contribute to the pathogenesis of common cold and exacerbation of asthma associated with HRV infection (Turner et al., (1998), *Clin. Infec. Dis.*, Vol. 26, p. 840; Teren et al. (1997), *Am. J. Respir. Crit. Care Med.*, Vol. 155, p. 1362; Grunberg et al. (1997), *Am. J. Respir. Crit. Care Med.*, Vol. 156, p. 609 and Zhu et al., *J. Clin. Invest.* (1996), Vol. 97, p 421). It has also been demonstrated in vitro that infection of pulmonary epithelial cells with HRV results in production of IL-6 and IL-8 (Subauste et al., *J. Clin. Invest.* (1995), Vol. 96, p. 549). Epithelial cells represent the primary site of infection of HRV. Therefore, another aspect of the present invention is a method of treatment to reduce inflammation associated with a rhinovirus infection, not necessarily a direct effect of the virus itself.

Another aspect of the present invention involves the novel use of these p38/cytokine inhibitors for the treatment of chronic inflammatory or proliferative or angiogenic diseases, which are caused by excessive, or inappropriate angiogenesis.

Chronic diseases which have an inappropriate angiogenic component are various ocular neovascularizations, such as diabetic retinopathy and macular degeneration. Other chronic diseases which have an excessive or increased proliferation of vasculature are tumor growth and metastasis, atherosclerosis and certain arthritic conditions. Therefore, cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

This invention also encompasses methods of treating or preventing disorders that can be treated or prevented by the inhibition of MAP in a mammal, preferably a human, comprising administering to said mammal an effective amount of a compound of the formula I.

Accordingly, the present invention provides a method of treating a p38 kinase mediated disease in a mammal in need thereof, preferably a human, which comprises administering to said mammal, an effective amount of a compound of Formula (I) or a pharmaceutically acceptable salt thereof.

Preferred p38 mediated diseases for treatment include, but are not limited to psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, ischemic and hemorrhagic stroke, neurotrauma/closed head injury, asthma, adult respiratory distress syndrome, chronic obstructive pulmonary disease, cerebral malaria, meningitis, chronic pulmonary inflammatory disease, silicosis, pulmonary sarcostosis, bone resorption disease, osteoporosis, restenosis, cardiac reperfusion injury, brain and renal reperfusion injury, chronic renal failure, thrombosis, glomerularonephritis, diabetes, diabetic retinopathy, macular degeneration, graft vs. host reaction, allograft rejection, inflammatory bowel disease, Crohn's disease, ulcerative colitis, neurodegenerative disease, multiple sclerosis, muscle degeneration, diabetic retinopathy, macular degeneration, tumor growth and metastasis, angiogenic disease, rhinovirus infection, peroral disease, such as gingivitis and periodontitis, eczema, contact dermatitis, psoriasis, sunburn, and conjunctivitis.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions for the treatment of a condition selected from the group consisting of arthritis, psoriatic arthritis, Reiter's syndrome, gout, traumatic arthritis, rubella arthritis and acute synovitis, rheumatoid arthritis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis shock in a mammal, including a human, comprising an amount of a compound of formula I effective in such treatment and a pharmaceutically acceptable carrier.

In one embodiment, said pharmaceutical composition is for the treatment of cancer such as brain, lung, squamous cell, bladder, gastric, pancreatic, breast, head, neck, renal, kidney, ovarian, prostate, colorectal, esophageal, gynecological or thyroid cancer. Other cancers that can be treated with the compounds of the present invention include bone cancer, skin cancer, cancer of the head and neck, cutaneous or intraocular melanoma, uterine cancer, rectal cancer or cancer of the anal region, stomach cancer, colon cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the small intestine, cancer of the endocrine system (e.g., cancer of the thyroid, parathyroid or adrenal glands), sarcomas of soft tissues, cancer of the urethra, cancer of the penis, chronic or acute leukemia, solid tumors of childhood or lymphocytic lymphomas.

In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

This invention also encompasses pharmaceutical compositions for the treatment of a condition which can be treated by the inhibition of MAP kinase in a mammal, including a human, comprising an amount of a compound of claim 1 effective in such treatment and a pharmaceutically acceptable carrier.

This invention also encompasses pharmaceutical compositions for the treatment of a condition which can be treated by the inhibition of p38 kinase in a mammal, including a human, comprising an amount of a compound of claim 1 effective in such treatment and a pharmaceutically acceptable carrier.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The invention also encompasses sustained release compositions.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), IL-1 inhibitors, receptor antagonists or soluble IL-1ra (e.g. Kineret or ICE inhibitors), COX-2 inhibitors (such as celecoxib, rofecoxib, valdecoxib and etoricoxib), metalloprotease inhibitors (preferably MMP-13 selective inhibitors), p2×7 inhibitors, α2δ inhibitors, low dose methotrexate, leflunomide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VegF inhibitors, and antimetabolites such as methotrexate. The compounds of the present invention may also be used in combination with a taxane derivative, a platinum coordination complex, a nucleoside analog, an anthracycline, a topoisomerase inhibitor, or an aromatase inhibitor.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, ACE inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, α2δ inhibitors, COX-2 inhibitors, gaba pentenoids, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

DETAILED DESCRIPTION OF THE INVENTION

Compounds of the formula I may be prepared according to the following reaction schemes and discussion. Unless otherwise indicated s, m, $R^1$—$R^{17}$ and X, and structural formula I (and Ia-Im) in the reaction schemes and discussion that follow are as defined above.

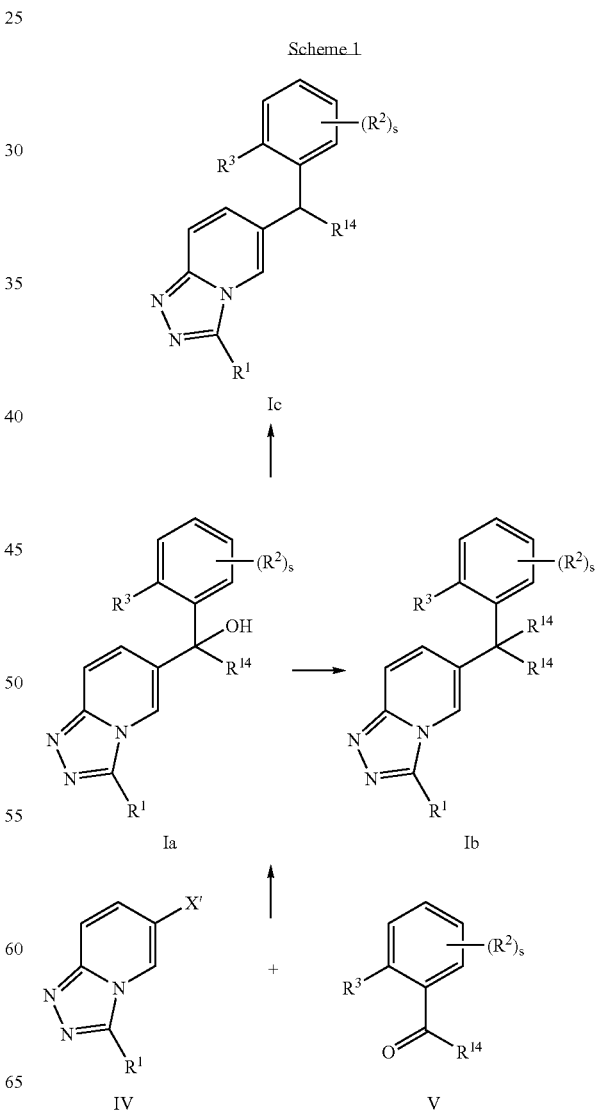

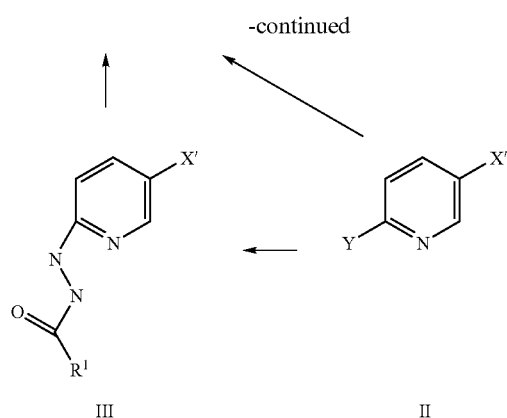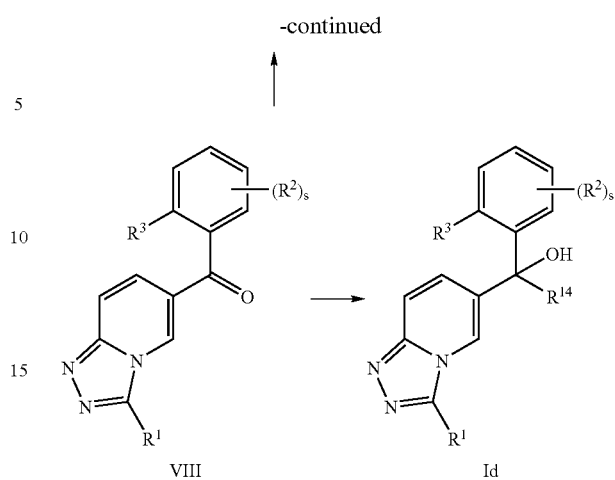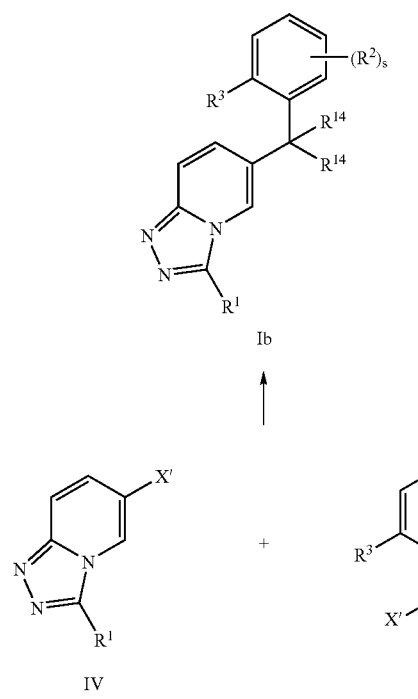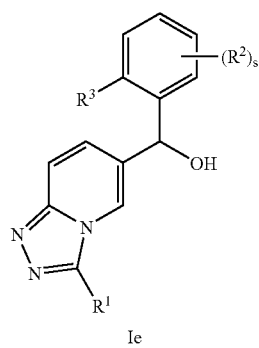

-continued
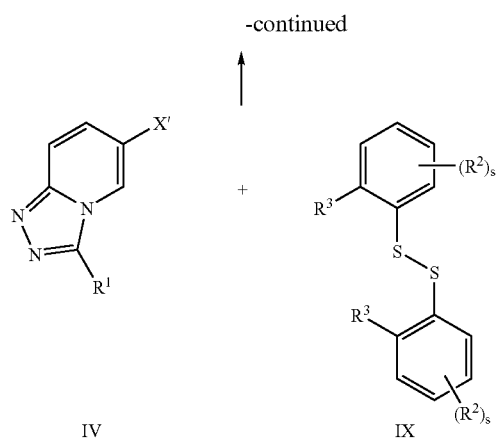
Scheme 5
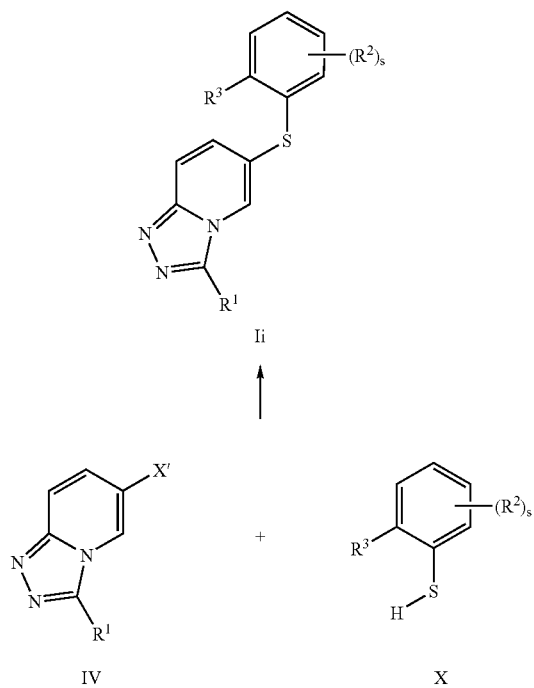
Scheme 6
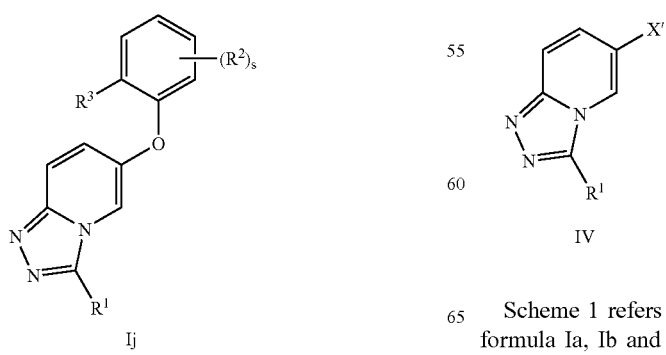
-continued
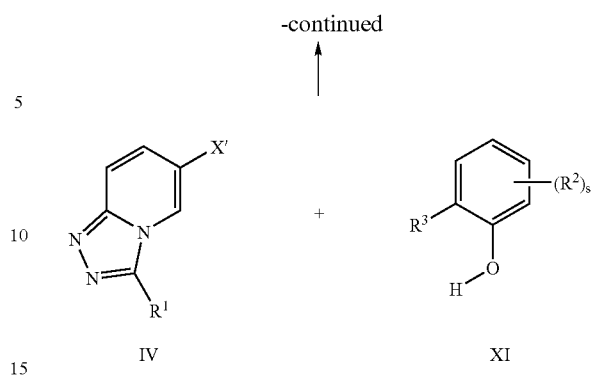
Scheme 7
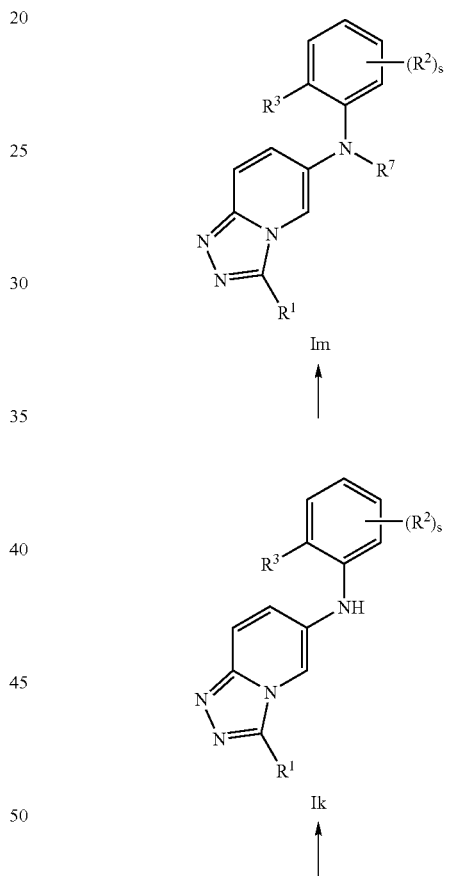
Scheme 1 refers to the preparation of compounds of the formula Ia, Ib and Ic. Compounds of formula Ia are compounds of the formula I, wherein X is >C(R$^{14}$)$_2$, and one of $R^{14}$ is hydrogen. Compounds of formula Ib are compounds of the formula I, wherein X is $>C(R^{14})_2$. Compounds of formula Ic are compounds of formula I, wherein X is $>C(R_{14})_2$ and one of $R^{14}$ is hydrogen. Referring to Scheme 1, compounds of the formula II, wherein Y is a suitable leaving group such as fluoro, bromo, chloro or mesyl (MeSO$_2$), preferably bromo or chloro, are converted to the corresponding compound of formula III by reaction with hydrazine to form a hydrazino-pyridine, followed by reaction with an acylating reagent. The reaction of a compound of formula II with hydrazine is conducted in a polar solvent such as pyridine, ethanol or tert-butanol, or in neat hydrazine, preferably in neat hydrazine. The hydrazine reaction is conducted at a temperature between about 40° C. to about 80° C., preferably about 70° C. for about 10 minutes to about 60 minutes, preferably about 15 minutes. Acylation of the resulting hydrazino-pyridine to give compounds of the formula III is conducted with an acid chloride in the presence of a base such as triethylamine in a solvent such as dichloromethane, tetrahydrofuran, N,N-dimethylformamide, preferably dichloromethane, for a time period between about 10 minutes to about 120 minutes, preferably about 30 minutes, at a temperature of about 0° C. to about 22° C., preferably at about 0° C. Alternatively, the hydrazino-pyridine can be acylated with a carboxylic acid to give compounds of the formula III using amide coupling agents in a manner well known to one skilled in the art.

The compound of formula III can be converted to a compound of formula IV using a suitable dehydrating agent or under conditions that promote cyclo-dehydration. Suitable dehydrating agents for the conversion of compounds of formula III to compounds of formula IV include phosphorous oxychloride and dichlorotriphenylphosphorane, preferably phosphorous oxychloride. Reactions using phosphorous oxychloride are conducted in neat phosphorous oxychloride at a temperature between about 60° C. to about 110° C., for a time period between about 2 hours to about 16 hours. Reactions using dichlorotriphenylphosphorane are conducted in the presence of a base, such as triethylamine, in a polar solvent such as acetonitrile, at temperatures of about 60° C. and reflux for a time period from about 1 hour and about 8 hours.

Alternatively compounds of formula IV can be prepared from compounds of formula II by reaction with a suitable acid halide. The reaction of compound II with an acid halide can be conducted in a solvent or neat, preferably neat with heating. Preferably the reaction is run at 60-120° C. for a period of 2-24 hours.

Compounds of the formula Ia are prepared by reaction of the Grignard product of compounds of the formula IV with compounds of the formula V. The reaction is conducted in a solvent such as tetrahydrofuran or ether at a temperature of −78° C. to 23° C., preferably at around 0° C. Formation of the Grignard reagent from compound IV is performed by reaction of compound IV with an alkyl magnesium chloride or bromide, preferably isopropyl magnesium chloride. Following this reaction a compound of the formula V is added and the reaction is heated to at or near the boiling point of the solvent preferably at about 50° C. for a period of 3 to 6 hours. Compounds of the formula V are generally commercially available or are easily prepared by someone skilled in the art.

Conversion of compound of formula Ia to compounds of formula Ic can be done by reaction with a suitable reducing agent. Appropriate reducing agents include zinc or hydrogen gas, preferably zinc in formic acid. The reactions are generally heated to 50 to 110° C. for about one to about four days.

Compounds of formula Ib can be prepared from compounds of formula Ia by reaction with a suitable coupling reagent. Suitable coupling reagents include acid chlorides, isocyanates, and alkyl halides.

Scheme 2 refers to the preparation of compounds of the formula Ib, which are compounds of the formula I, wherein X is $>C(R^{14})_2$, and each $R^{14}$ is hydrogen. Referring to Scheme 2, compounds of the formula Ib are prepared from compounds of the formula IV by reaction with suitable compounds of the formula VI in the presence of a catalyst. Typically compounds of the formula VI are converted to the benzyl zincate by reaction with zinc dust in a solvent at a temperature from about 50° C. to about 70° C. Following formation of the benzyl zincate, compounds of the formula IV are added along with a palladium catalyst and the reactions are heated to around 50° C. Typical palladium catalysts include palladium tetrakistriphenylphosphine.

Scheme 3 refers to the preparation of compounds of the formula Id and Ie. Compounds of the formula Id are compounds of formula I, wherein X is $>C(R^{14})_2$, and one of $R^{14}$ is hydroxy and the other of $R^{14}$ is other than hydrogen. Compounds of the formula Ie are compounds of the formula I, wherein X is $>C(R^{14})_2$, and one of $R^{14}$ is hydroxy and the other of $R^{14}$ is hydrogen. Referring to Scheme 3, compounds of the formula IV are converted to the Grignard reagent as described previously and subsequently reacted with compounds of the formula VII in a solvent, preferably tetrahydrofuran, to form compounds of the formula VIII. Compounds of the formula VIII can be converted to compounds of the formula Ie by reaction with an appropriate reducing agent. Suitable reducing agents include sodium borohydride. Compounds of the formula VIII can be converted to compounds of the formula Id by reaction with an appropriate Grignard reagent.

Scheme 4 refers to the preparation of compounds of the formula If, Ig and Ih. Compounds of formula If are compounds of formula I, wherein X is sulfur. Compounds of formula Ig are compounds of formula I, wherein X is SO$_2$. Compounds of formula Ih are compounds of formula I wherein X is $>S=O$. Referring to Scheme 4, a compound of formula If is prepared by reaction of compounds of the formula IV with compounds of the formula IX. Compounds of the formula IV are converted to their Grignard reagent as described previously. Compounds of the formula IX are then reacted with the Grignard reagent in a solvent, preferably tetrahydrofuran, at a temperature of between 0° C. and 50° C., preferably between 0° C. and 23° C. for a period of 4 hours to 3 days. Compounds of the formula If in Scheme 4 are converted to compounds of the formula Ig and Ih by reaction with a suitable oxidizing agent. Typical oxidizing agents include m-chloroperbenzoic acid. Compounds of the formula IX are prepared by standard methods.

Scheme 5 refers to the preparation of compounds of the formula Ii from compounds of the formula IV by reaction with compounds of the formula X. Typically the reaction is done in the presence of a catalyst and a base. Typical catalysts include PdCl$_2$(dppf)—CH$_2$Cl$_2$ and typical bases include cesium carbonate. Typical solvents include dimethylformamide.

Scheme 6 refers to the preparation of compounds of the formula Ij from compounds of the formula IV and compounds of the formula XI by methods similar to those reported in Scheme 5.

Scheme 7 refers to the preparation of compounds of the formula Ik and Im. Referring to Scheme 7, compounds of the formula Ik are prepared from compounds of the formula IV and compounds of the formula XII by methods similar to those reported in Scheme 5. Compounds of the formula If are prepared from compounds of the formula Ik by reaction with a suitable alkylating agent or acylating agent.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The activity of the compounds of the invention for the various disorders described above may be determined according to one or more of the following assays. All of the compounds of the invention, that were tested, had an $IC_{50}$ less than 10 µM in the TNFα and MAPKAP in vitro assays and an $ED_{50}$ of less than 50 mg/kg in the in vivo TNFα assay.

The compounds of the present invention also possess differential activity (i.e. are selective for) for one or more p38 kinases (i.e. α, β, γ, and δ) or other MAP kinases. Certain compounds are selective for p38α over p38β, γ, and δ, other compounds are selective for p38β over p38α, γ, and δ, other compounds are selective for p38 α and β over p38 γ and δ. Selectivity is measured in standard assays as an $IC_{50}$ ratio of inhibition in each assay. Certain compounds have a selectivity ratio of greater than one. Other compounds have selectivity ratios of greater than 100 against other kinases.

Inhibition of TNF-Alpha Production by Human LPS-Treated Monocytes

Mononuclear cells are isolated from heparinized blood (1.5 ml of 1000 units/ml heparin for injection, Elkins-Sinn, Inc. added to each 50 ml sample) using Accuspin System-Histopaque-1077 tubes (Sigma A-7054). Thirty-five milliliters of whole blood are added to each tube and the tubes are centrifuged at 2100 rpm for 20 minutes in a Beckman GS-6KR centrifuge with the brake off at room temperature. The mononuclear cells which collect at the interface are removed, diluted with Macrophage serum free medium (Gibco-BRL) (Medium) to achieve a final volume of 50 ml, and collected by centrifugation for 10 minutes. The supernatant is discarded and the cell pellet is washed 2 times with 50 ml of Medium. A sample of the suspended cells is taken before the second wash for counting. Based on this count, the washed cells are diluted with Medium containing 1% FBS to a final concentration of $2.7 \times 10^6$ cells/ml and 75 µl of the cell suspension is added to each well of a 96 well plate.

Compound Preparation

Compounds are routinely tested at final concentrations from 2 µM to 0.016 µM, but may be tested at other concentrations, depending on activity. Test agents are diluted with DMSO to a final concentration of 2 mM. From this stock solution, compounds are first diluted 1:25 (5 µl of 2 mM stock+120 µl Medium containing 400 ng/ml LPS and 1% FBS then 40 µl of this dilution is diluted with 360 µl of Medium with LPS. Serial dilutions (1/5) are performed by transferring 20 $R^1$ of this dilution to 80 µl of Medium containing both LPS and 0.4% DMSO, resulting in solutions containing 8 µM, 1.6 µM, 0.32 µM and 0.064 µM of test agent.

Assay

The assay is initiated by adding 25 µL of the diluted compounds to the mononuclear cell suspension and incubating the cells at 37 C and 5% $CO_2$ for 4 hours.

The 96-well plates are then centrifuged for 10 minutes at 2000 rpm at 4° C. in a Beckman GS-6KR centrifuge to remove cells and cell debris. A 90 µl aliquot of each supernatant is removed and transferred to a 96 well round bottom plate, and this plate is centrifuged a second time to insure that all cell debris is removed. 80 µl of the supernatant is removed and transferred to a new round bottom plate.

Supernatants are analyzed for TNF-α content using R&D ELISA. 25 µl of each sample is added to an ELISA well containing 25 µl of assay diluent RD1F and 75 µl of assay diluent RD5. The assay is run following kit directions except 100 µl of conjugate and substrate solutions are used.

Interpretation

The amount of TNF-α immunoreactivity in the samples is calculated as follows:

% Control=$(X–B)/(TOT–B) \times 100$ where X=$OD_{450}$ nm of the test compound well
B=$OD_{450}$ of Reagent Blank wells on the ELISA
Total =$OD_{450}$ of cells that were treated with 0.1% DMSO only.

Mapkap Kinase-2 Assay

Monocyte Preparation

Mononuclear cells are collected from heparinized human blood as detailed above. The washed cells are seeded into 6-well cluster plates at a density of $1 \times 10^7$ cells/well (in 2 ml of Medium). The plates are incubated at 37° C. in a 5% $CO_2$ environment for 2 hours to allow adherence of the monocytes, after which time media supernatants containing non-adherent cells are removed by aspiration and 2 ml of fresh medium are added to each well. Plates are incubated overnight at 37° C. in a 5% $CO_2$ environment.

Cell Activation

Media are removed by aspiration. The attached cells are rinsed twice with fresh Medium, then 2 ml of D-MEM medium containing 10% heat inactivated FBS are added to each well. Test compounds are prepared as 30 mM stock solutions in DMSO and diluted to 1250, 250, 50, 10, 2, and 0.4 μM in D-MEM containing 1% DMSO and 10% FBS. To individual wells of the monocyte cultures, 20 μl of these test agent dilutions are added resulting in final test agent concentrations of 12.5, 2.5, 0.5, 0.1, 0.02 and 0.004 μM. After a 10 minute preincubation period, 20 μl of a 10 μg/ml LPS solution are added to each well and the plates are incubated at 37° C. for 30 min. Media subsequently are removed by aspiration, the attached monocytes are rinsed twice with phosphate buffered saline, then 1 ml of phosphate buffered saline containing 1% Triton X-100 (Lysis Buffer; also containing 1 Complete™ tablet [Boehringer #1697498] per 10 ml of buffer) is added to each well. The plates are incubated on ice for 10 minutes, after which the lysates are harvested and transferred to centrifugation tubes. After all samples are harvested, they are clarified by centrifugation (45,000 rpm for 20 min) and the supernatants recovered.

MAPKAP Kinase-2 Immunoprecipitation

5 μl of anti-MAPKAP kinase-2 antiserum (Upstate Biotechnology #06-534) is added to a microcentrifuge tube (1 tube for each of the above cell lysates) containing 1 ml of a 5% suspension of Protein G-Sepharose (Sigma #P3296) in PBS. These mixtures are incubated for 1 hour at 4° C. (with rocking) after which the beads, containing bound IgG, are recovered by centrifugation and washed twice with 1 ml of 50 mM Tris, pH 7.5, 1 mM EDTA, 1 mM EGTA, 0.5 mM orthovanadate, 0.1% 2-mercaptoethanol, 1% Triton X-100, 5 mM sodium pyrophosphate, 10 mM sodium β-glycerophosphate, 0.1 mM phenylmethylsulfonyl fluoride, 1 μg/ml leupeptin, 1 μg/ml pepstatin, and 50 mM sodium fluoride (Buffer A) by repeated centrifugation. An individual monocyte cell extract (prepared above) is then transferred to each tube containing a pellet of IgG-coated Protein G-Sepharose, and these mixtures are incubated for 2 hours at 4° C. (with rocking). The beads subsequently are harvested by centrifugation, and the resulting bead pellets are washed once with 0.5 ml of Buffer A containing 0.5 M NaCl, once with 0.5 ml of Buffer A, and once with 0.1 ml of a buffer composed of 20 mM MOPS, pH 7.2, 25 mM sodium β-glycerophosphate 5 mM EGTA, 1 mM orthovanadate, and 1 mM dithiothreitol (Buffer B).

MAPKAP Kinase-2 Activity Assessment

A kinase reaction mixture stock is prepared as follows: 2.2 μl of 10 mCi/ml γ[$^{32}$P]ATP, 88 μl of 1.3 μg/ml solution of MAPKAP Kinase-2 substrate peptide (Upstate Biotechnology #12-240), 11 μl of 10 mM ATP, 8.8 μl of 1 M $MgCl_2$, and 770 μl of Buffer B. To each of the immune complex-Protein G-pellets, 40 μl of the kinase reaction mixture are added and the tubes are incubated for 30 minutes at 30° C. The tubes then are clarified by centrifugation and 25 μl of each supernatant is spotted onto a P81 filter paper disk (Whatman #3698-023). After allowing all fluid to soak into the filter, each disk is placed into an individual well of 6-well cluster plates and the filters are washed sequentially with 2 ml of 0.75% phosphoric acid (3 washes/15 min each) and once with acetone (10 min). The filters then are air dried and transferred to liquid scintillation vials containing 5 ml of scintillation fluid. Radioactivity is determined in a liquid scintillation counter. The amount of radioactivity bound to the filter at each test agent concentration is expressed as a percentage of that observed from cells stimulated with LPS in the absence of a test agent.

In Vivo Inhibition of TNFα

Rats were weighed and dosed with vehicle (0.5% methyl cellulose, Sigma) or drug. One hour later, animals were injected i.p. with LPS (50 ug/rat, Sigma L-4130). Ninety minutes later, animals were sacrificed by asphyxiation with $CO_2$ and bled by cardiac puncture. Blood was collected in Vaccutainer tubes and spun for 20 minutes at 3000 rpm. Serum was assayed for TNFα levels using an ELISA (R&D Systems).

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., inflammation) is 0.1 to 200 mg of the active ingredient per unit dose which could be administered, for example, 1 to 4 times per day.

Aerosol formulations for treatment of the conditions referred to above (e.g., adult respiratory distress syndrome) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of an MAP kinase inhibitor, preferably from about 1 mg to about 200 mg of p38 kinase inhibitor. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonitrile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 amu to 1100 amu. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32-63 mm silica gel and executed under nitrogen pressure (flash chromatography) conditions. Room or ambient temperature refers to 20-25° C. All non-aqueous reactions were run under a nitrogen atmosphere for convenience and to maximize yields. Concentration at reduced pressure means that a rotary evaporator was used.

One of ordinary skill in the art will appreciate that in some cases, protecting groups may be required during preparation. After the target molecule is prepared, the protecting group can be removed by methods well known to those of ordinary skill in the art, such as described in Greene and Wuts, *Protective Groups in Organic Synthesis*, (2nd Ed., John Wiley & Sons, 1991).

EXAMPLE 1

6-Benzyl-3-(2-chloro-phenyl)-[1,2,4]triazolo[4,3-a]pyridine

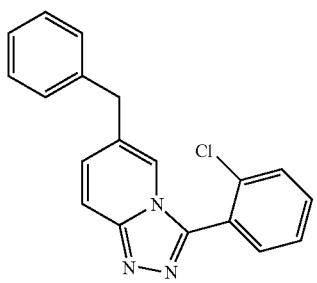

A) (5-Bromo-pyridin-2-yl)-hydrazine

A mixture of 2,5-Dibromo-pyridine (13 g, 55.1 mmol) and hydrazine (13 mL, 414 mmol) in pyridine (13 mL) was heated at 85° C. for 48 hours. The reaction was cooled and concentrated in vacuo. The residue was triturated in 1N NaOH (20 mL) and toluene (20 mL). The solid was filtered, washed with water, and dried to give the above named compound (6.43 g, 62%).

2-Chloro-benzoic acid N'-(5-bromo-pyridin-2-yl)-hydrazide

To (5-bromo-pyridin-2-yl)-hydrazine (2.0 g, 10.6 mmol) and triethylamine (1.5 mL, 11.0 mmol) in 1:1 THF:CH$_2$Cl$_2$ (15 mL) was added 2-chlorobenzoyl chloride (1.34 mL, 10.6 mmol) and the resulting reaction stirred for 16 hours. The reaction was quenched with water (100 mL), the resulting solids filtered, and dried to give the title compound (2.96 g, 85%).

6-Bromo-3-(2-chloro-Phenyl)-[1,2,4]triazolo[4,3-a]pyridine

A mixture of 2-chloro-benzoic acid N'-(5-bromo-pyridin-2-yl)hydrazide (2.96 g, 9.1 mmol) in POCl$_3$ (15 mL) was heated at 85° C. for 48 hours. The solvent was removed in vacuo, and the residue quenched with saturated Na$_2$CO$_3$ and EtOAc. The layers were separated, and the organic layer concentrated in vacuo to minimal volume. The resulting solid was filtered and purified by flash chromatography to give the title compound (0.85 g, 30%).

6-Benzyl-3-(2-chloro-phenyl)-[1,2,4]triazolo[4,3-a]pyridine

To a flame-dried flask under nitrogen was added Rieke zinc (2.3 mL, 1.75 mmol). The total volume of the reaction was brought to 5 mL using dry THF. To the slurry was added dibromoethane (10.0 μL, 0.01 mmol), and the reaction warmed to 65° C. for 3 minutes. The reaction was then cooled to 35° C., and chlorotrimethylsilane (30.0 μL, 0.25 mmol) added, and the resulting reaction stirred for 30 minutes at 35° C. Benzyl bromide (55 uL, 0.46 mmol), was added and the reaction stirred a further 30 minutes at 35° C. To the mixture was then added 6-bromo-3-(2-chloro-phenyl)-[1,2,4]triazolo[4,3-a]pyridine (136 mg, 0.44 mmol) and Pd(PPh$_3$)$_4$ and the temperature increased to 50° C. Flash chromatography purification (elution with 35-85% ethyl acetate/hexane), followed by preparatory HPLC (15-80% water/acetonitrile) of the crude reaction mixture yielded the title compound (10 mg, 7%). MS (M+1)=320.4.

EXAMPLE 2

[3-(2-Chloro-phenyl)-[1,2,4]triazolo[4,3-a]pyridin-6-yl]-p-tolyl-methanol

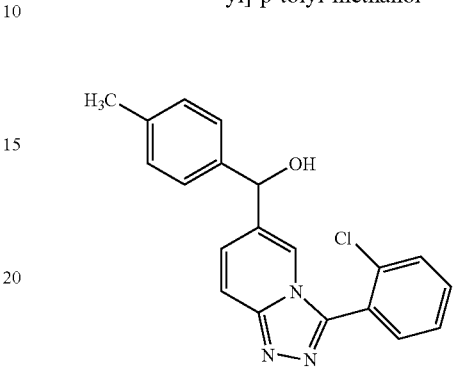

[3-(2-Chloro-phenyl)-[1,2,4]triazolo[4,3-a]pyridin-6-yl]-p-tolyl-methanol

In a flame-dried flash under nitrogen a solution of 6-bromo-3-(2-chloro-phenyl)-[1,2,4]triazolo[4,3-a]pyridine (205 mg, 0.66 mmol) in THF (2.5 mL) was cooled to 0° C. A solution of isopropylmagnesium chloride (1.3 eq) was added dropwise, followed by 4-methylbenzaldehyde (1 equivalent), and the resulting mixture was warmed to 50° C. for 3 hours. The reaction was cooled and quenched with water/ethyl acetate. The organic layer was separated, concentrated in vacuo, and the residue purified by flash chromatography (eluting with 80% ethyl acetate/hexane) to give the title compound (67 mg, 29%). MS (M+1)=350.5.

EXAMPLE 3

6-(4-Fluoro-benzyl)-3-isopropyl-[1,2,4]triazolo[4,3-a]pyridine

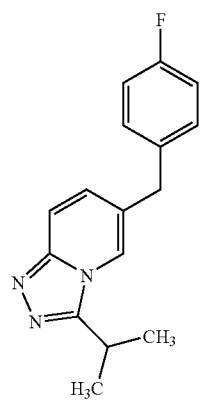

A) (4-Fluoro-phenyl)-(3-isopropyl-[1,2,4]triazolo[4,3-a]pyridin-6-yl)-methanol To a solution of 3-isopropyl-[1,2,4]triazolo[4,3-a]pyridine-6-carbaldehyde (404.6 mg, 2.13 mmol) in THF (8 mL) at ambient temperature was added 4-fluorophenylmagnesium bromide (3 mL, 1.0 M in THF). The resulting reaction was stirred for 20 hours, then quenched with water, followed by saturated NaHCO$_3$. The reaction mixture was extracted with ethyl acetate, the organics dried over sodium sulfate, and concentrated to give the above named compound (591.3 mg, 97%).

B) 6(4-Fluoro-benzyl)-3-isopropyl-[1,2,4]triazolo[4,3-a]pyridine

A mixture of (4-fluoro-phenyl)-(3-isopropyl-[1,2,4]triazolo[4,3-a]pyridin-6-yl)-methanol (591.3 mg, 2.07 mmol), Zn (1 g), and formic acid (3 mL) was heated at 105° C. for 4 days. The reaction was cooled, concentrated in vacuo, and quenched with saturated Na$_2$CO$_3$. The reaction mixture was extracted with ethyl acetate, the extracts dried over sodium sulfate and concentrated in vacuo. The residue was purified by flash chromatography (eluting with 10% methanol/ethyl acetate), followed by ethyl acetate precipitation (following addition of HCl in dioxane). The crude precipitate was recrystallized from MeOH/EtOAc to give the title compound (175.6 mg, 21%).

The compounds of Examples 4-13 can be prepared according to the methods of Examples 1-3.

TABLE 1

| EXAMPLE # | MOLSTRUCTURE | IUPAC NAME | LCMS M/Z |
|---|---|---|---|
| 4 | | 6-Benzyl-3-isopropyl-[1,2,4]triazolo[4,3-a]pyridine | M + 1 = 252.2 |
| 5 | | (3-Isopropyl-[1,2,4]triazolo[4,3-a]pyridin-6-yl)-m-tolyl-methanol | M + 1 = 282.2 |
| 6 | | (4-Fluoro-3-methyl-phenyl)-(3-isopropyl-[1,2,4]triazolo[4,3-a]pyridin-6-yl)-methanol | M + 1 = 300.1 |

TABLE 1-continued

| EXAMPLE # | MOLSTRUCTURE | IUPAC NAME | LCMS M/Z |
|---|---|---|---|
| 7 | | 3-Isopropyl-6-(3-methyl-benzyl)-[1,2,4]triazolo[4,3-a]pyridine | |
| 8 | | [3-(2-Chloro-phenyl)-[1,2,4]triazolo[4,3-a]pyridin-6-yl]-m-tolyl-methanol | M + 1 = 350.3 |
| 9 | | 3-(2-Chloro-phenyl)-6-(3-methyl-benzyl)-[1,2,4]triazolo[4,3-a]pyridine | M + 1 = 334.3 |
| 10 | | (3-Phenyl-[1,2,4]triazolo[4,3-a]pyridin-6-yl)-m-tolyl-methanol | M + 1 = 316.4 |

TABLE 1-continued

| EXAMPLE # | MOLSTRUCTURE | IUPAC NAME | LCMS M/Z |
|---|---|---|---|
| 11 | | 6-(3-Methyl-benzyl)-3-phenyl-[1,2,4]triazolo[4,3-a]pyridine | M + 1 = 300.5 |
| 12 | | 3-(2-Chloro-phenyl)-6-(4-methyl-benzyl)-[1,2,4]triazolo[4,3-a]pyridine | M + 1 = 334.5 |
| 13 | | [3-(2-Chloro-phenyl)-[1,2,4]-triazolo[4,3-a]pyridin-6-yl]-o-tolyl-methanol | M + 1 = 350.5 |

EXAMPLE 14

3-Isopropyl-6-phenylsulfanyl-[1,2,4]triazolo[4,3-a]pyridine

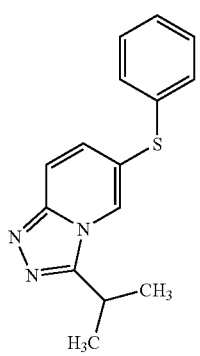

A) (5-Bromo-pyridin-2-yl)-hydrazine

A mixture of 2,5-Dibromo-pyridine (13 g, 55.1 mmol) and hydrazine (13 mL, 414 mmol) in pyridine (13 mL) was heated at 85° C. for 48 hours. The reaction was cooled and concentrated in vacuo. The residue was triturated in 1N NaOH (20 mL) and toluene (20 mL). The solid was filtered, washed with water, and dried to give the above named compound (6.43 g, 62%).

B)
6-Bromo-3-isopropyl-[1,2,4]triazolo[4.3-b]pyridin

To a flask containing (6-bromo-pyridazin-3-yl)-hydrazine (1.84 g, 9.77 mmol) was added isobutyryl chloride (≅10 mL) until a uniform solution was obtained. The reaction was heated at 95° C. for 20 hours. The reaction was concentrated in vacuo to yield a yellow-orange solid. The solids were triturated from ethyl acetate to afford the above named compound (1.8 g, 77%).

C) 3-Isopropyl-6-phenylsulfanyl-[1,2,4]triazolo[4,3-a]pyridine

To 6-bromo-3-isopropyl-[1,2,4]triazolo[4,3-b]pyridine (242.8 mg, 1.01 mmol) at 0° C. was added isopropylmagnesium bromide (1 mmol) and the resulting reaction stirred for 1 hour. Phenyl disulfide (243.3 mg, 1.11 mmol) was then added and the mixture stirred for 2 hours at 0° C., then at ambient temperature for 48 hours. The reaction was quenched with ethyl acetate and NaHCO₃. The reaction mixture was extracted, dried over sodium sulfate, and concentrated in vacuo. The residue was purified by flash chromatography (eluting with 20% ethyl/hexane to ethyl acetate) to give the title compound (117.4 mg, 43%). MS (M+1)= 270.3

The compounds of Examples 15-39 can be prepared according to the methods of Example 14.

TABLE 2

| EXAMPLE # | MOLSTRUCTURE | IUPAC NAME | DATA LCMS M/Z |
|---|---|---|---|
| 15 | | 6-(3-Fluoro-phenyl-sulfanyl)-3-iso-propyl-[1,2,4]tri-azolo[4,3-a]py-ridine | M + 1 = 288.3 |
| 16 | | 6-(4-Chloro-phenyl-sulfanyl)-3-iso-propyl-[1,2,4]tri-azolo[4,3-a]py-ridine | M + 1 = 304.2 |
| 17 | | 3-Isopropyl-6-(3-tri-fluoromethyl-phenyl-sulfanyl)-[1,2,4]tri-azolo[4,3-a]py-ridine | M + 1 = 338.6 |
| 18 | | 6-Phenylsulfanyl-3-pyr-rolidin-1-yl-[1,2,4]tri-azolo[4,3-a]py-ridine | M + 1 = 297.6 |

TABLE 2-continued

| EXAMPLE # | MOLSTRUCTURE | IUPAC NAME | DATA LCMS M/Z |
|---|---|---|---|
| 19 | | 3-Isobutyl-6-phenyl-sulfanyl-[1,2,4]triazolo[4,3-a]pyridine | M + 1 = 284.1 |
| 20 | | 3-(2-Chloro-phenyl)-6-phenyl-sulfanyl-[1,2,4]triazolo[4,3-a]pyridine | M + 1 = 338.7 |
| 21 | | 3-Ethyl-6-phenyl-sulfanyl-[1,2,4]triazolo[4,3-a]pyridine | M + 1 = 256.1 |
| 22 | | 6-(4-Fluoro-phenyl-sulfanyl)-3-iso-propyl-[1,2,4]triazolo[4,3-a]pyridine | M + 1 = 288.2 |
| 23 | | 3-Cyclobutyl-6-phenyl-sulfanyl-[1,2,4]triazolo[4,3-a]pyridine | M + 1 = 282.2 |

TABLE 2-continued

| EXAMPLE # | IUPAC NAME | DATA LCMS M/Z |
|---|---|---|
| 24 | 3-Ethyl-6-(4-fluoro-phenyl-sulfanyl)-[1,2,4]triazolo[4,3-a]pyridine | M + 1 = 274.1 |
| 25 | 6-(3-Chloro-phenyl-sulfanyl)-3-isopropyl-[1,2,4]triazolo[4,3-a]pyridine | M + 1 = 304.1 |
| 26 | 6-(2,3-Dichloro-phenyl-sulfanyl)-3-isopropyl-[1,2,4]triazolo[4,3-a]pyridine | M + 1 = 338.0 |
| 27 | 6-(2-Fluoro-phenyl-sulfanyl)-3-isopropyl-[1,2,4]triazolo[4,3-a]pyridine | M + 1 = 288.1 |
| 28 | 3-(2-Chloro-phenyl)-6-(4-chloro-phenyl-sulfanyl)-[1,2,4]triazolo[4,3-a]pyridine | M + 1 = 372.2 |

TABLE 2-continued

| EXAMPLE # | IUPAC NAME | DATA LCMS M/Z |
|---|---|---|
| 29 | 6-(4-Chloro-phenyl-sulfanyl)-3-cyclo-butyl-[1,2,4]tri-azolo[4,3-a]py-ridine | M + 1 = 316.2 |
| 30 | 6-(4-Chloro-phenyl-sulfanyl)-3-iso-butyl-[1,2,4]tri-azolo[4,3-a]py-ridine | M + 1 = 318.2 |
| 31 | 3-Phenyl-6-phenyl-sulfanyl-[1,2,4]tri-azolo[4,3-a]py-ridine | M + 1 = 304.2 |
| 32 | 6-(4-Chloro-phenyl-sulfanyl)-3-phe-nyl-[1,2,4]tri-azolo[4,3-a]py-ridine | M + 1 = 338.2 |
| 33 | 6-(2-Chloro-phenyl-sulfanyl)-3-iso-propyl-[1,2,4]triazolo[4,3-a]py-ridine | M + 1 = 304.2 |

TABLE 2-continued

| EXAMPLE # | MOLSTRUCTURE | IUPAC NAME | DATA LCMS M/Z |
| --- | --- | --- | --- |
| 34 | | 6-(4-Chloro-phenyl-sulfanyl)-3-cyclopropyl-[1,2,4]triazolo[4,3-a]pyridine | M + 1 = 302.2 |
| 35 | | 6-(4-Chloro-phenyl-sulfanyl)-3-cyclopentyl-[1,2,4]triazolo[4,3-a]pyridine | M + 1 = 330.3 |
| 36 | | 3-(4-Chloro-phenyl)-6-(4-chloro-phenyl-sulfanyl)-[1,2,4]triazolo[4,3-a]pyridine | M + 1 = 372. |
| 37 | | 3-(2-Chloro-phenyl)-6-(2-fluoro-phenyl-sulfanyl)-[1,2,4]triazolo[4,3-a]pyridine | M + 1 = 356.1 |
| 38 | | 3-(2-Chloro-phenyl)-6-(2,4-difluoro-phenyl-sulfanyl)-[1,2,4]triazolo[4,3-a]pyridine | M + 1 = 374.2 |

TABLE 2-continued

| EXAMPLE # | MOLSTRUCTURE | IUPAC NAME | DATA LCMS M/Z |
|---|---|---|---|
| 39 | | 2-(3-Isopropyl-[1,2,4]tri-azolo[4,3-a]py-ridin-6-yl-sulfanyl)-benzoic acid | |

EXAMPLE 40

[2-(3-Isopropyl-[1,2,4]triazolo[4,3-a]pyridin-6-ylsulfanyl)-phenyl]-methanol

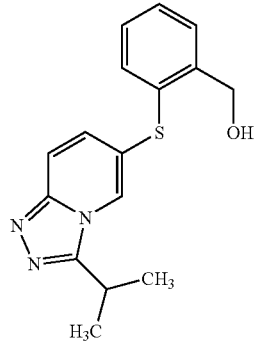

[2-(3-Isopropyl-[1,2,4]triazolo[4,3-a]pyridin-6-ylsulfanyl)-phenyl]-methanol

To a solution of 6-bromo-3-isopropyl-[1,2,4]triazolo[4,3-b]pyridine (6.0 g, 25 mmol), $Cs_2CO_3$ (11.4 g, 35 mmol), and $PdCl_2$(dppf).$CH_2Cl_2$ (2.0 g, 2.5 mmol) in DMF (50 mL) under nitrogen at ambient temperature was added 2-mercaptobenzyl alcohol (4.55 g, 32.5 mmol). The resulting solution was heated to 90° C. for 21 hours. The reaction was cooled, and water and ethyl acetate added. The precipitate was filtered and washed with dichloromethane, followed by water to yield the title compound (5.6 g). The filtrate was extracted with ethyl acetate, the organics combined, dried over sodium sulfate, and concentrated in vacuo. The residue was purified by flash chromatography (eluting with 10% methanol/ethyl acetate) to yield 350 mg of title compound, resulting in 5.95 g (80%).

EXAMPLE 41

1-Ethyl-3-[2-(3-isopropyl-[1,2,4]triazolo[4,3-a]pyridin-6-ylsulfanyl)-benzyl-urea

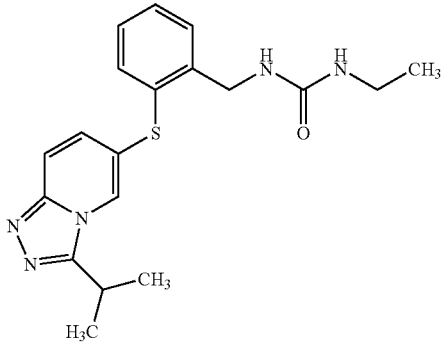

A) 6-(2-Azidomethyl-phenylsulfanyl)-3-isopropyl-[1,2,4]triazolo[4,3-a]pyridine

To a suspension of [2-(3-Isopropyl-[1,2,4]triazolo[4,3-a]pyridin-6-ylsulfanyl)-phenyl]-methanol (254.0 mg, 0.85 mmol) and DPPA (220 μL, 1.02 mmol) in toluene (8.5 mL, 0.10 M) at 0° C. was added DBU (152.0 μL, 1.02 mmol), followed by the addition of THF (1 mL). The reaction was allowed to warm to ambient temperature and stirred for 18 hours. The reaction mixture was quenched with $NaHCO_3$, and extracted with ethyl acetate. The extracts were washed with brine, dried over sodium sulfate and concentrated in vacuo. The residue was purified by flash chromatography (eluting with 2% methanol/ethyl acetate) to give the title compound as an oil (228 mg, 83%). MS (M+1)=370.5.

B) 2-(3-Isopropyl-[1,2,4]triazolo[4,3-a]pyridin-6-ylsulfanyl)-benzylamine

To a solution of 6-(2-Azidomethyl-phenylsulfanyl)-3-isopropyl-[1,2,4]triazolo[4,3-a]pyridine (228.0 mg, 0.70 mmol) in THF (2.3 mL) under $N_2$ was added triphenylphosphine (220.0 mg, 0.84 mmol) and water (15.0 μL, 0.84 mmol). The reaction was stirred at ambient temperature under $N_2$ for 12 hours, then warmed to 50° C. for 6 hours.

To the reaction mixture was diluted with water, and extracted with ethyl acetate. The extracts were washed with brine, dried over sodium sulfate and concentrated in vacuo. The residue was purified by flash chromatography (10-100% methanol/ethyl acetate), followed by trituration with ethyl acetate/hexane to give the title compound (127 mg, 61%).

C) 1-Ethyl-3-[2-(3-isopropyl-[1,2,4]triazolo[4,3-a]pyridin-6-ylsulfanyl)-benzyl]-urea To a solution of 2-(3-Isopropyl-[1,2,4]triazolo[4,3-a]pyridin-6-ylsulfanyl)-benzylamine (200.0 mg, 0.671 mmol) in dichloromethane (6.71 mL) under nitrogen at ambient temperature was added ethyl isocyanate (53.0 µL, 0.67 mmol). The reaction was stirred for 20 minutes, then the solvent was removed in vacuo. The residue was recrystallized from ethyl acetate to give the title compound (231 mg, 94%). MS (M+1)=370.5.

EXAMPLE 42
Ethyl-carbamic acid 2-(3-isopropyl-[1,2,4]triazolo[4,3-a]pyridin-6-ylsulfanyl)-benzyl ester

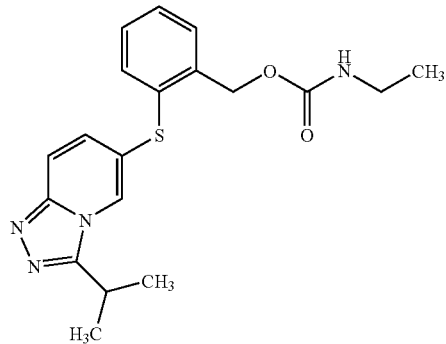

To a solution of [2-(3-Isopropyl-[1,2,4]triazolo[4,3-a]pyridin-6-ylsulfanyl)-phenyl]-methanol (45.0 mg, 0.15 mmol) in dichloromethane (1.5 mL) under nitrogen at ambient temperature was added ethyl isocyanate (12.0 µL, 0.15 mmol). The reaction was heated to 50° C. for 1 hour. The reaction was cooled, ethyl isocyanate added (30 µL, 0.38 mmol), and stirred at ambient temperature for 16 hours. The reaction was concentrated in vacuo to an oil. The residue was triturated from ether to give the title compound (45 mg, 82%). MS (M+1)=371.4.

EXAMPLE 43

1-Ethyl-3-[2-(3-isopropyl-[1,2,4]triazolo[4,3-a]pyridin-6-ylsulfanyl)-benzyl]-1-methyl-urea

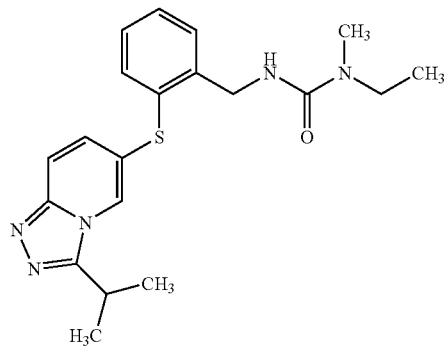

A) [2-(3-Isopropyl-[1,2,4]triazolo[4,3-a]pyridin-6-ylsulfanyl)-benzyl]-carbamic acid phenyl ester To a solution of 2-(3-Isopropyl-[1,2,4]triazolo[4,3-a]pyridin-6-ylsulfanyl)-benzylamine (417 mg, 1.4 mmol) in dichloromethane (14 mL) at ambient temperature under nitrogen was added pyridine (226 µL, 2.8 mmol) and phenyl chloroformate (192 µL, 1.5 mmol). The reaction was stirred for 20 minutes, then quenched with saturated NaHCO$_3$. The reaction mixture was extracted with dichloromethane, the combined organics washed with brine, dried over sodium sulfate, and concentrated in vacuo. Purification by flash chromatography (eluting with ethyl acetate), followed by ether/hexane trituration gave the above named compound as a white solid (526 mg, 90%).

B) 1-Ethyl-3-[2-(3-isopropyl-[1,2,4]triazolo[4,3-a]pyridin-6-ylsulfanyl)-benzyl]-1-methyl-urea To a solution of [2-(3-Isopropyl-[1,2,4]triazolo[4,3-a]pyridin-6-ylsulfanyl)-benzyl]-carbamic acid phenyl ester (42 mg, 0.10 mmol) in DMSO (200 µL) was added ethylmethylamine (6.0 µL, 0.105 mmol). The reaction was stirred at ambient temperature for 30 minutes, then quenched with water. The reaction mixture was extracted with organics, the organics combined, dried over sodium sulfate, and concentrated in vacuo. The residue was triturated with 1:1 hexane:diethyl ether to give the title compound (37 mg, 96%). MS (M+1)=384.4.

EXAMPLE 44

N-[2-(3-Isopropyl-[1,2,4]triazolo[4,3-a]pyridin-6-ylsulfanyl)-benzyl]-acetamide

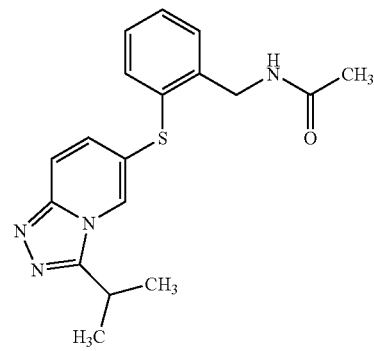

N-[2-(3-Isopropyl-[1,2,4]triazolo[4,3-a]pyridin-6-ylsulfanyl)-benzyl]-acetamide

To a solution of 2-(3-Isopropyl-[1,2,4]triazolo[4,3-a]pyridin-6-ylsulfanyl)-benzylamine (30 mg, 0.1 mmol) in dichloromethane (400 µL) was added pyridine (16 µL, 0.2 mmol) and acetic anhydride (9 µL, 0.1 mmol) and the reaction stirred for 25 minutes at ambient temperature. The reaction was concentrated in vacuo to an oily residue. The residue was purified by flash chromatography (eluting with 10% methanol/ethyl acetate), followed by trituration with diethyl ether to yield the title compound as a white solid (23 mg, 68%). MS (M+1)=341.4.

The compounds of Examples 45-107 can be prepared according to the methods of Examples 41-44.

TABLE 3

| EXAMPLE # | MOLSTRUCTURE | IUPAC NAME | LCMS M/Z |
| --- | --- | --- | --- |
| 45 | | 1-(2,5-Dimethyl-2H-pyrazol-3-yl)-3-[2-(3-isopropyl-[1,2,4]triazolo[4,3-a]pyridin-6-yl-sulfanyl)-benzyl]-urea | M + 1 = 436.5 |
| 46 | | N-[2-(3-Isopropyl-[1,2,4]triazolo[4,3-a]pyridin-6-yl-sulfanyl)-benzyl]-isobutyramide | M + 1 = 369.5 |
| 47 | | [2-(3-Isopropyl-[1,2,4]triazolo[4,3-a]pyridin-6-yl-sulfanyl)-benzyl]-carbamic acid ethyl ester | M + 1 = 371.4 |
| 48 | | 1-Allyl-3-[2-(3-isopropyl-[1,2,4]triazolo[4,3-a]pyridin-6-yl-sulfanyl)-benzyl]-urea | M + 1 = 382.5 |

TABLE 3-continued

| EXAMPLE # | MOLSTRUCTURE | IUPAC NAME | LCMS M/Z |
|---|---|---|---|
| 49 | | 1-Isopropyl-3-[2-(3-isopropyl-[1,2,4]triazolo[4,3-a]pyridin-6-ylsulfanyl)-benzyl]-urea | M + 1 = 384.4 |
| 50 | | 1-[2-(3-Isopropyl-[1,2,4]triazolo[4,3-a]pyridin-6-ylsulfanyl)-benzyl]-3-methyl-urea | M + 1 = 356.4 |
| 51 | | [2-(3-Isopropyl-[1,2,4]triazolo[4,3-a]pyridin-6-ylsulfanyl)-benzyl]-urea | M + 1 = 342.2 |
| 52 | | N-[2-(3-Isopropyl-[1,2,4]triazolo[4,3-a]pyridin-6-ylsulfanyl)-benzyl]-2-methoxy-acetamide | M + 1 = 371.5 |

TABLE 3-continued

| EXAMPLE # | MOLSTRUCTURE | IUPAC NAME | LCMS M/Z |
|---|---|---|---|
| 53 | | 1-(5-tert-Butyl-2-methyl-2H-pyrazol-3-yl)-3-[2-(3-isopropyl-[1,2,4]triazolo[4,3-a]pyridin-6-ylsulfanyl)-benzyl]-urea | M + 1 = 478.6 |
| 54 | | N-[2-(3-Isopropyl-[1,2,4]triazolo[4,3-a]pyridin-6-ylsulfanyl)-benzyl]-butyramide | M + 1 = 369.5 |
| 55 | | 1-sec-Butyl-3-[2-(3-isopropyl-[1,2,4]triazolo[4,3-a]pyridin-6-ylsulfanyl)-benzyl]-urea | 398.4 |
| 56 | | 1-[2-(3-Isopropyl-[1,2,4]triazolo[4,3-a]pyridin-6-ylsulfanyl)-benzyl]-3-phenyl-urea | 418.5 |

TABLE 3-continued

| EXAMPLE # | MOLSTRUCTURE | IUPAC NAME | LCMS M/Z |
|---|---|---|---|
| 57 | | Carbonic acid ethyl ester 2-(3-isopropyl-[1,2,4]triazolo[4,3-a]pyridin-6-yl-sulfanyl)-benzyl ester | 372.4 |
| 58 | | N-[2-(3-Isopropyl-[1,2,4]triazolo[4,3-a]pyridin-6-yl-sulfanyl)-benzyl]-benzamide | 403.4 |
| 59 | | [2-(3-Cyclobutyl-[1,2,4]triazolo[4,3-a]pyridin-6-yl-sulfanyl)-phenyl]-methanol | 312.2 |
| 60 | | [2-(3-tert-Butyl-[1,2,4]triazolo[4,3-a]pyridin-6-yl-sulfanyl)-phenyl]-methanol | 314.2 |

TABLE 3-continued

| EXAMPLE # | MOLSTRUCTURE | IUPAC NAME | LCMS M/Z |
|---|---|---|---|
| 61 | | Ethyl-carbamic acid 2-(3-tert-butyl-[1,2,4]triazolo[4,3-a]pyridin-6-yl-sulfanyl)-benzyl ester | 385.5 |
| 62 | | Ethyl-carbamic acid 2-(3-cyclobutyl-[1,2,4]triazolo[4,3-a]pyridin-6-yl-sulfanyl)-benzyl ester | 383.5 |
| 63 | | 1-Cyanomethyl-3-[2-(3-isopropyl-[1,2,4]triazolo[4,3-a]pyridin-6-yl-sulfanyl)-benzyl]-urea | 381.5 |
| 64 | | 6-(2-Azidomethyl-phenylsulfanyl)-3-tert-butyl-[1,2,4]triazolo[4,3-a]pyridine | |

TABLE 3-continued

| EXAMPLE # | MOLSTRUCTURE | IUPAC NAME | LCMS M/Z |
|---|---|---|---|
| 65 | | [2-([1,2,4]Triazolo[4,3-a]pyridin-6-yl-sulfanyl)-benzyl]carbamic acid ethyl ester | 329.5 |
| 66 | | 3-Isopropyl-6-o-tolyl-sulfanyl-[1,2,4]triazolo[4,3-a]pyridine | 284.5 |
| 67 | | Ethyl-carbamic acid 2-(3-tert-butyl-[1,2,4]triazolo[4,3-a]pyridine-6-sulfinyl)-benzyl ester | |
| 68 | | 1-Furan-2-ylmethyl-3-[2-(3-isopropyl-[1,2,4]triazolo[4,3-a]pyridin-6-yl-sulfanyl)-benzyl]-urea | 422.4 |

TABLE 3-continued

| EXAMPLE # | MOLSTRUCTURE | IUPAC NAME | LCMS M/Z |
|---|---|---|---|
| 69 | | 1-(5-tert-Butyl-2-methyl-2H-pyrazol-3-yl)-3-[2-([1,2,4]triazolo[4,3-a]pyridin-6-yl-sulfanyl)-benzyl]-urea | 436.6 |
| 70 | | [5-Fluoro-2-(3-isopropyl-[1,2,4]triazolo[4,3-a]pyridin-6-yl-sulfanyl)-phenyl]-methanol | 318.5 |
| 71 | | 1-(1H-Benzoimidazol-2-yl)-3-[2-(3-isopropyl-[1,2,4]triazolo[4,3-a]pyridin-6-yl-sulfanyl)-benzyl]-urea | 458.5 |
| 72 | | 1-Benzyl-3-[2-(3-isopropyl-[1,2,4]triazolo[4,3-a]pyridin-6-yl-sulfanyl)-benzyl]-urea | 432.5 |

TABLE 3-continued

| EXAMPLE # | MOLSTRUCTURE | IUPAC NAME | LCMS M/Z |
|---|---|---|---|
| 73 | | 1-[2-(3-Isopropyl-[1,2,4]tri-azolo[4,3-a]py-ridin-6-yl-sulfanyl)-ben-zyl]-3-(3-meth-oxy-propyl)-urea | 414.4 |
| 74 | | 1-(5-tert-Butyl-iso-xazol-3-yl)-3-[2-(3-iso-propyl-[1,2,4]tri-azolo[4,3-a]py-ridin-6-yl-sulfanyl)-benzyl]-urea | 465.5 |
| 75 | | 1-(4-Cyano-cyclo-hexylmethyl)-3-[2-(3-iso-propyl-[1,2,4]tri-azolo[4,3-a]py-ridin-6-yl-sulfanyl)-benzyl]-urea | 463.5 |
| 76 | | 1-[2-(3-Isopropyl-[1,2,4]tri-azolo[4,3-a]py-ridin-6-yl-sulfanyl)-benzyl]-3-(2-py-ridin-2-yl-ethyl)-urea | 447.5 |

TABLE 3-continued

| EXAMPLE # | MOLSTRUCTURE | IUPAC NAME | LCMS M/Z |
|---|---|---|---|
| 77 | | 1-[2-(3-Isopropyl-[1,2,4]triazolo[4,3-a]pyridin-6-ylsulfanyl)-benzyl]-3-(2H-pyrazol-3-yl)-urea | 408.5 |
| 78 | | 2-(3-Isopropyl-[1,2,4]triazolo[4,3-a]pyridin-6-ylsulfanyl)-benzaldehyde | 298.4 |
| 79 | | 1-[2-(3H-Imidazol-4-yl)-ethyl]-3-[2-(3-isopropyl-[1,2,4]triazolo[4,3-a]pyridin-6-ylsulfanyl)-benzyl]-urea | 436.5 |
| 80 | | 1-[2-(3-Isopropyl-[1,2,4]triazolo[4,3-a]pyridin-6-ylsulfanyl)-benzyl]-3-(1-phenyl-ethyl)-urea | 446.6 |

TABLE 3-continued

| EXAMPLE # | IUPAC NAME | LCMS M/Z |
|---|---|---|
| 81 | 1-[2-(3-Isopropyl-[1,2,4]triazolo[4,3-a]pyridin-6-yl-sulfanyl)-phenyl]-ethanol | 314.5 |
| 82 | 1-(2-Hydroxy-propyl)-3-[2-(3-isopropyl-[1,2,4]triazolo[4,3-a]pyridin-6-yl-sulfanyl)-benzyl]-urea | 400.4 |
| 83 | 3-[2-(3-Isopropyl-[1,2,4]triazolo[4,3-a]pyridin-6-yl-sulfanyl)-phenyl]-acrylic acid ethyl ester | 368.3 |
| 84 | Ethyl-carbamic acid 5-fluoro-2-(3-isopropyl-[1,2,4]triazolo[4,3-a]pyridin-6-ylsulfanyl)-benzyl ester | 389.5 |

TABLE 3-continued

| EXAMPLE # | MOLSTRUCTURE | IUPAC NAME | LCMS M/Z |
| --- | --- | --- | --- |
| 85 | | [2-(3-tert-Butyl-[1,2,4]tri-azolo[4,3-a]py-ridin-6-yl-sulfanyl)-benzyl]-(1H-py-razol-3-yl)-amine | 423.5 |
| 86 | | [2-(3-tert-Butyl-[1,2,4]tri-azolo[4,3-a]py-ridin-6-yl-sulfanyl)-benzyl]-isoxa-zol-3-yl-amine | 380.5 |
| 87 | | [2-Fluoro-6-(3-iso-propyl-[1,2,4]tri-azolo[4,3-a]py-ridin-6-yl-sulfanyl)-phenyl]-methanol | 318.5 |
| 88 | | Ethyl-carbamic acid 2-fluoro-6-(3-iso-propyl-[1,2,4]tri-azolo[4,3-a]py-ridin-6-yl-sulfanyl)-benzyl ester | 389.5 |

TABLE 3-continued

| EXAMPLE # | MOLSTRUCTURE | IUPAC NAME | LCMS M/Z |
|---|---|---|---|
| 89 | | [2-(3-tert-Butyl-[1,2,4]triazolo[4,3-a]pyridin-6-yl-sulfanyl)-benzyl]-(5-methyl-2H-pyrazol-3-yl)-amine | 393.3 |
| 90 | | 3-[2-(3-Isopropyl-[1,2,4]triazolo[4,3-a]pyridin-6-yl-sulfanyl)-phenyl]-acrylic acid | 340.3 |
| 91 | | 5-[2-(3-tert-Butyl-[1,2,4]triazolo[4,3-a]pyridin-6-yl-sulfanyl)-benzyl-amino]-1-methyl-1H-pyrazole-4-carboxylic acid ethyl ester | 465.6 |
| 92 | | [2-(3-tert-Butyl-[1,2,4]triazolo[4,3-a]pyridin-6-yl-sulfanyl)-benzyl]-(5-methyl-isoxazol-3-yl)-amine | 394.5 |

TABLE 3-continued

| EXAMPLE # | MOLSTRUCTURE | IUPAC NAME | LCMS M/Z |
|---|---|---|---|
| 93 | | N-Ethyl-3-[2-(3-isopropyl-[1,2,4]triazolo[4,3-a]pyridin-6-yl-sulfanyl)-phenyl]-acrylamide | 367.5 |
| 94 | | 1-[2-(3-Isopropyl-[1,2,4]triazolo[4,3-a]pyridin-6-yl-sulfanyl)-phenyl]-hex-2-yn-1-ol | 366.5 |
| 95 | | [2-(3-tert-Butyl-[1,2,4]triazolo[4,3-a]pyridin-6-yl-sulfanyl)-phenyl]-acetonitrile | 323.4 |
| 96 | | 1-[2-(3-Isopropyl-[1,2,4]triazolo[4,3-a]pyridin-6-yl-sulfanyl)-phenyl]-hex-2-yn-1-one | 364.5 |

TABLE 3-continued

| EXAMPLE # | MOLSTRUCTURE | IUPAC NAME | LCMS M/Z |
|---|---|---|---|
| 97 | | 3-Isopropyl-6-[2-(5-propyl-2H-pyrazol-3-yl)-phenylsulfanyl]-[1,2,4]triazolo[4,3-a]pyridine | 378.5 |
| 98 | | [2-(3-tert-Butyl-[1,2,4]triazolo[4,3-a]pyridin-6-ylsulfanyl)-benzyl]-(5-ethyl-[1,3,4]thiadiazol-2-yl)-amine | 425.3 |
| 99 | | 3-Isopropyl-6-[2-(3-propyl-isoxazol-5-yl)-phenylsulfanyl]-[1,2,4]triazolo[4,3-a]pyridine | 379.5 |
| 100 | | 3-tert-Butyl-6-[2-(1H-tetrazol-5-ylmethyl)-phenylsulfanyl]-[1,2,4]triazolo[4,3-a]pyridine | 366.4 |

TABLE 3-continued

| EXAMPLE # | MOLSTRUCTURE | IUPAC NAME | LCMS M/Z |
|---|---|---|---|
| 101 | | 1-[2-(3-Isopropyl-[1,2,4]tri-azolo[4,3-a]py-ridin-6-yl-sulfanyl)-phenyl]-but-2-yn-1-ol | 338.4 |
| 102 | | 1-[2-(3-Isopropyl-[1,2,4]tri-azolo[4,3-a]py-ridin-6-yl-sulfanyl)-phenyl]-but-3-en-1-ol | 340.5 |
| 103 | | N-[2-(3-Isopropyl-[1,2,4]tri-azolo[4,3-a]py-ridin-6-yl-sulfanyl)-benzyl]-pro-pionamide | 355.3 |
| 104 | | 3-[2-(3-Isopropyl-[1,2,4]tri-azolo[4,3-a]py-ridin-6-yl-sulfanyl)-phenyl]-allylamine | 325.4 |

TABLE 3-continued

| EXAMPLE # | MOLSTRUCTURE | IUPAC NAME | LCMS M/Z |
|---|---|---|---|
| 105 | | N-{3-[2-(3-Isopropyl-[1,2,4]tri-azolo[4,3-a]pyridin-6-yl-sulfanyl)-phenyl]-allyl}-acetamide | 367.4 |
| 106 | | 4-[2-(3-Isopropyl-[1,2,4]tri-azolo[4,3-a]pyridin-6-yl-sulfanyl)-phenyl]-but-3-en-2-ol | 340.4 |
| 107 | | 1-[2-(3-Isopropyl-[1,2,4]tri-azolo[4,3-a]pyridin-6-yl-sulfanyl)-phenyl]-pent-1-en-3-ol | 354.4 |

EXAMPLE 108

3-Isopropyl-6-phenoxy-[1,2,4]triazolo[4,3-a]pyridine

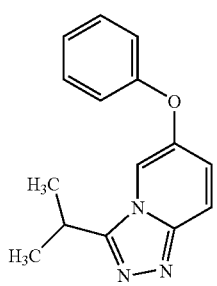

A (5-Bromo-pyridin-2-yl)-hydrazine

A mixture of 2,5-Dibromo-pyridine (13 g, 55.1 mmol) and hydrazine (13 mL, 414 mmol) in pyridine (13 mL) was heated at 85° C. for 48 hours. The reaction was cooled and concentrated in vacuo. The residue was triturated in 1N NaOH (20 mL) and toluene (20 mL). The solid was filtered, washed with water, and dried to give the above named compound (6.43 g, 62%).

B) 6-Bromo-3-isopropyl-[1,2,4]triazolo[4,3-b]pyridine

To a flask containing (5-bromo-pyridin-2-yl)-hydrazine (1.84 g, 9.77 mmol) was added isobutyryl chloride (≅10 mL) until a uniform solution was obtained. The reaction was heated at 95° C. for 20 hours. The reaction was concentrated in vacuo to yield a yellow-orange solid. The solids were triturated from ethyl acetate to afford the above named compound (1.8 g, 77%).

C) 3-Isopropyl-6-phenoxy-[1,2,4]triazolo[4,3-a]pyridine

A flask containing phenol (188 mg, 2 mmol) and potassium hydroxide (112 mg, 2 mmol) in dimethylacetal (0.25 mL) was heated at 150° C. under $N_2$ for 1 hour. To the reaction was added 6-bromo-3-isopropyl-[1,2,4]triazolo[4,3-b]pyridine (480 mg, 2 mmol) and copper powder (~30 mg, catalytic) and the resulting reaction heated at 200° C. for 3 hours. The reaction was then cooled, quenched with saturated $NH_4Cl$ and ethyl acetate, and the resulting mixture filtered. The layers were separated and the aqueous extracted with ethyl acetate. The organic layers were combined, dried over sodium sulfate, and concentrated in vacuo. The crude was purified by flash chromatography (eluting with 5% acetone/hexane), followed by recrystallization to give the title compound (160 mg, 32%). LCMS (m/z) 354.3 (M+1).

The compounds of Examples 109-111 can be prepared according to the methods of Example 108.

TABLE 1

| EXAMPLE # | MOLSTRUCTURE | IUPAC NAME | DATA LCMS M/Z |
|---|---|---|---|
| 109 | | 6-(4-Fluoro-phenoxy)-3-isopropyl-[1,2,4]triazolo[4,3-a]pyridine | 272.2 |
| 110 | | 6-(3-Chloro-phenoxy)-3-isopropyl-[1,2,4]triazolo[4,3-a]pyridine | 288.2 |
| 111 | | 3-(2-Chloro-phenyl)-6-phenoxy-[1,2,4]triazolo]4,3-a]pyridine | 322.7 |

EXAMPLE 112

Ethyl-carbamic acid 2-(3-isopropyl-[1,2,4]triazolo[4,3-a]pyridin-6-yloxy)-benzyl ester

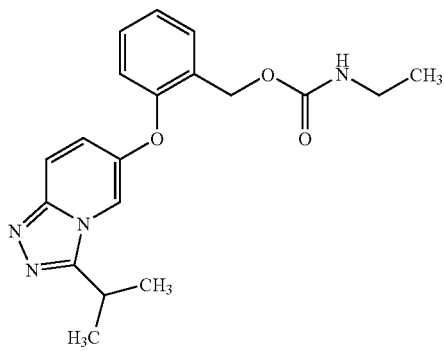

A Acetic acid 6-chloro-pyridin-3-yl ester

To a solution of 6-Chloro-pyridin-3-ylamine (3.2 g, 25 mmol) in ethylene glycol dimethyl ether (10.9 mL) and methylene chloride (3.6 mL) at −10° C. was added boron trifluoride diethyl etherate (6.8 mL, 53.2 mmol), followed by tert-butyl nitrite (3.56 mL, 30 mmol) in ethylene glycol dimethyl ether (3.6 mL). The resulting viscous suspension was stirred at −5° C. for 10 minutes, then 0° C. for 30 minutes, at which point cold pentane was added to the suspension. The resulting solid was filtered and washed with cold pentane. The crude solid was dissolved in acetic anhydride (28 mL, 300 mmol) and heated at 75° C. for 3.5 hours. The reaction was concentrated to an oil. The residue was purified by flash chromatography (eluting with 20% ethyl acetate/hexane) to afford the above named compound as a light brown liquid (1.71 g, 40%).

B 6-Chloro-pyridin-3-ol

To a solution of acetic acid 6-chloro-pyridin-3-yl ester (1.67 g, 9.8 mmol) in methanol (10 mL) was added potassium carbonate (676 mg, 4.9 mmol), and the resulting reaction stirred at ambient temperature for 2 hours. The reaction was concentrated to an oily solid which was partitioned between water and diethyl ether. The water layer was neutralized with 3N HCl (3.7 mL), and extracted with diethyl ether (1×). The organics were combined, washed with brine, dried over sodium sulfate, and concentrated in vacuo to give the above named compound as a tan solid (1.04 g, 82%).

C 2-(6-Chloro-pyridin-3-yloxy)-benzaldehyde

A mixture of 6-chloro-pyridin-3-ol (418 mg, 3.2 mmol), 2-fluorobenzaldehyde (522 mg, 4.21 mmol), potassium carbonate (442 mg, 3.2 mmol) and copper powder (201 mg, 3.2 mmol) was heated in DMF (6.4 mL) at 120° C. for 6 hours. The reaction was then cooled, and concentrated to an oil. The residue was purified by flash chromatography (eluting with 20% ethyl acetate/hexane) to give the title compound as a brown solid (700 mg, 93%).

D [2-(6-Chloro-pyridin-3-yloxy)-phenyl]-methanol

To a solution of 2-(6-chloro-pyridin-3-yloxy)-benzaldehyde (250 mg, 1.07 mmol) in methanol at ambient temperature was added sodium borohydride (49 mg, 1.3 mmol). The resulting reaction was stirred for 30 minutes, then quenched with saturated NaHCO₃. The methanol was removed in vacuo, and the residue was diluted with water and extracted with ethyl acetate. The combined organics were washed with brine, dried over sodium sulfate, and concentrated in vacuo to an oil. The crude was purified by flash chromatography (eluting with 25% ethyl acetate/hexane) to give the above named compound as an oil (250 mg, 100%).

E [2-(6-Hydrazino-pyridin-3-yloxy)-phenyl]-methanol

A mixture of [2-(6-chloro-pyridin-3-yloxy)-phenyl]-methanol (235 mg, 1 mmol) and hydrazine monohydrate (5 mL) was heated at 120° C. for 4 hours. The reaction was then cooled and concentrated in vacuo to an oil. The residue was then diluted with saturated NaHCO₃, and the aqueous extracted with methylene chloride. The organics were washed with brine, dried over sodium sulfate, and concentrated in vacuo to afford the above named compound.

F Isobutyric acid 2-(3-isopropyl-[1,2,4]triazolo[4,3-a]pyridin-6-yloxy)-benzyl ester A mixture of {2-(6-hydrazino-pyridin-3-yloxy)-phenyl]-methanol (231 mg, 1 mmol) and isobutyryl chloride (938 µL, 9 mmol) was heated at 105° C. for 3 hours. The reaction was cooled to ambient temperature and quenched with saturated NaHCO₃. The aqueous was extracted with ethyl acetate and the organics combined, dried over sodium sulfate, and concentrated in vacuo to an oil. The residue was purified by flash chromatography (eluting with 2% methanol/ethyl acetate) to give the title compound (136 mg, 39% for two steps).

G [2-(3-Isopropyl-[1,2,4]triazolo[4.3-a]pyridin-6-yloxy)-phenyl]-methanol

A mixture of isobutyric acid 2-(3-isopropyl-[1,2,4]triazolo[4,3-a]pyridin-6-yloxy)-benzyl ester (130 mg, 0.37 mmol) and potassium hydroxide (103 mg, 1.84 mmol) in tetrahydrofuran (6 mL) and water (1 mL) was heated at 60° C. for 7 hours. The reaction was concentrated in vacuo to a solid. The residue was suspended in water, the solid filtered, then the material suspended in methylene chloride and filtered to give the above named compound as a tan solid (84 mg, 80%).

H Ethyl-carbamic acid 2-(3-isopropyl-[1,2,4]triazolo[4,3-a]pyridin-6-yloxy)-benzyl ester A suspension of [2-(3-isopropyl-[1,2,4]triazolo[4,3-a]pyridin-6-yloxy)-phenyl]-methanol (28 mg, 0.1 mmol) and ethyl isocyanate (14 µL, 0.2 mmol) was heated at 60° C. for 18 hours. The reaction was then cooled and concentrated in vacuo to an oil. The crude was purified by flash chromatography (eluting with 2% methanol/ethyl acetate), followed by suspension in 7:3 hexane:ethyl acetate. The solid was filtered to give the title compound as a white solid (17 mg, 48%) LCMS (m/z) 355.4 (M+1).

EXAMPLE 113

N-Ethyl-3-[2-(3-isopropyl-[1,2,4]triazolo[4,3-a]pyridin-6-ylsulfanyl)-phenyl]-acrylamide Tablet Formulation:

| Ingredient | Amount (mg) |
|---|---|
| N-Ethyl-3-[2-(3-isopropyl-[1,2,4]triazolo[4,3-a]pyridin-6-ylsulfanyl)-phenyl]-acrylamide | 50 |
| Lactose | 50 |
| Cornstarch (for mix) | 10 |
| Cornstarch (paste) | 10 |
| Magnesium stearate (1%) | 5 |
| Total | 125 |

The invention claimed is:

1. A compound of the formula

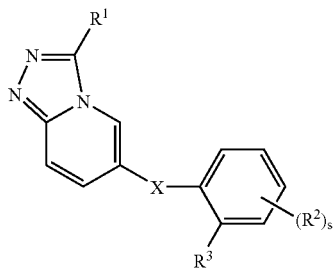

I wherein the molecular weight of the compound of formula I is less than 1000 AMU;

X is >$CH_2$ >NH, sulfur, >S=O, >$SO_2$ or oxygen;

$R^1$ is selected from the group consisting of hydrogen, ($C_1$-$C_6$)alkyl;

$R^2$ is selected from the group consisting of hydrogen, ($C_1$-$C_6$)alkyl;

s is an integer from 0-4;

$R^3$ is $R^4$, $R^5$—(N$R^6$)—, $R^5$—S—, $R^5$—(S=O)—, $R^5$—($SO_2$)—, $R^5$—$SO_2$—N$R^6$—, $R^5$—(N$R^6$)—$SO_2$—, $R^5$—O—, $R^5$—(C=O)—, $R^5$—(N$R^6$)—(C=O)—, $R^5$—(C=O)—N$R^6$—, $R^5$—O—(C=O)—, $R^5$—(C=O)—O—, $R^5$—C$R^7$=C$R^8$— or $R^5$—C≡C—;

such that the molecular weight of $R^3$ is less than 500 AMU;

$R^4$, $R^5$ and $R^6$ are each selected from the group consisting of hydrogen, ($C_1$-$C_6$)alkyl;

wherein the molecular weight of the compound of formula I is less than 1000 AMU;

or a pharmaceutically acceptable salt thereof.

2. A compound of the formula

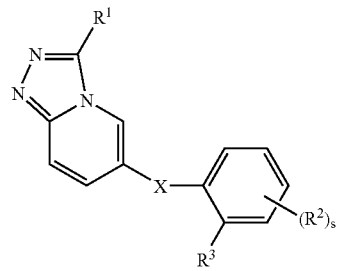

I wherein $R^1$ is selected from the group of substituents consisting of hydrogen, —C≡N, ($C_1$-$C_6$)alkyl, ($C_2$-$C_6$)alkenyl, ($C_2$-$C_6$)alkynyl-I, ($C_3$-$C_{10}$)cycloalkyl, phenyl, ($C_1$-$C_{10}$)heteroaryl, ($C_1$-$C_{10}$)heterocyclic and ($R^{17}$)$_2$—N—; wherein each of the aforesaid ($C_1$-$C_6$) alkyl, ($C_3$-$C_{10}$)cycloalkyl, phenyl, ($C_1$-$C_{10}$)heteroaryl and ($C_1$-$C_{10}$)heterocyclic substituents may optionally be independently substituted by one to four moieties independently selected from the group consisting of halo, ($C_1$-$C_6$)alkyl, ($C_2$-$C_6$)alkenyl, ($C_2$-$C_6$)alkynyl-I, perhalo($C_1$-$C_6$)alkyl, phenyl, ($C_3$-$C_{10}$)cycloalkyl, ($C_1$-$C_{10}$)heteroaryl, ($C_1$-$C_{10}$)heterocyclic, formyl, —C≡N, ($C_1$-$C_6$)alkyl-(C=O)—, phenyl-(C=O)—, HO—(C=O)—, ($C_1$-$C_6$)alkyl —O—(C=O)—, ($C_1$-$C_6$) alkyl-NH—(C=O)—, [($C_1$-$C_6$)alkyl]$_2$—N—(C=O)—, phenyl-NH—(C=O)—, phenyl-[(($C_1$-$C_6$) alkyl)—N]—(C=O)—, —$NO_2$, amino, ($C_1$-$C_6$) alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$) alkyl)—N]—, phenyl-(C=O)—NH—, phenyl-(C=O)—[(($C_1$-$C_6$)alkyl)—N]—, $H_2$N—(C=O)—NH—, ($C_1$-$C_6$)alkyl-HN—(C=O)—NH—, [($C_2$-$C_6$) alkyl]$_2$—N—(C=O)—NH—, ($C_1$-$C_6$)alkyl-HN—(C=O)—[(($C_1$-$C_6$)alkyl)—N]—, [($C_1$-$C_6$)alkyl]$_2$—N—(C=O)—[(($C_1$-$C_6$)alkyl)—N]—, phenyl-HN—(C=O)—NH—, (phenyl)$_2$—N—(C=O)—NH—, phenyl-HN—(C=O)—[(($C_1$-$C_6$)alkyl)—N]—, (phenyl)$_2$—N—(C=O)—[(($C_1$-$C_6$)alkyl)N]—, ($C_1$-$C_6$) alkyl —O—(C=O)—NH—, ($C_1$-$C_6$)alkyl-O—(C=O)—[($C_1$-$C_6$)alkyl)—N]—, phenyl-O—(C=O)—NH—, phenyl-O—(C=O)—[($C_1$-$C_6$) alkyl)—N]—, ($C_1$-$C_6$)alkyl-$SO_2$NH—, phenyl-$SO_2$NH—, ($C_1$-$C_6$)alkyl-$SO_2$—, phenyl-$SO_2$—, hydroxy, ($C_1$-$C_6$)alkoxy, perhalo($C_1$-$C_6$)alkoxy, phenoxy, ($C_1$-$C_6$)alkyl-(C=O)—O—, phenyl-(C=O)—O—, $H_2$N—(C=O)—O—, ($C_1$-$C_6$)alkyl-HN—(C=O)—O—, [($C_1$-$C_6$)alkyl]$_2$—N—(C=O)—O—, phenyl-HN—(C=O)—O— and (phenyl)$_2$—N—(C=O)—O—; wherein when said $R^1$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of ($C_1$-$C_6$)alkyl, halo, ($C_1$-$C_6$)alkoxy, perhalo($C_1$-$C_6$)alkyl and perhalo ($C_1$-$C_6$)alkoxy;

s is an integer from zero to four;

each $R^2$ is independently selected from the group consisting of hydrogen, halo, ($C_1$-$C_4$)alkyl, and —$CF_3$;

$R^3$ is $R^4$, $R^5$—(NR$^6$)—, $R^5$—S—, $R^5$—(S=O)—, $R^5$—(SO$_2$)—, $R^5$—SO$_2$—NR$^6$—, $R^5$—(NR$^6$)—SO$_2$—, $R^5$—O—, $R^5$—(C=O)R$^5$—(NR$^6$)—(C=O)—, $R^5$(C=O)—NR$^6$—, $R^5$—O—(C=O)—, $R^5$ (C=O)—O—, $R^5$—CR$^7$=CR$^8$— or $R^5$—C≡C—;

$R^4$ is hydrogen, halo, —C≡N, $(R^9)_m$—$(C_1$-$C_6)$alkyl, $(R^9)_m$—$(C_2$-$C_6)$alkenyl, perhalo$(C_1$-$C_6)$alkyl, $(R^9)_m$-phenyl, $(R^9)_m$—$(C_1$-$C_{10})$heteroaryl, $(R^9)_m$—$(C_1$-$C_{10})$heterocyclic, or $(R^9)_m$—$(C_3$-$C_{10})$cycloalkyl, $R^5$ is hydrogen, —C≡N, $(R^9)_m$—$(C_1$-$C_6)$alkyl-, $(R^9)_m$—$(C_2$-$C_6)$alkenyl, $(R^9)_m$—$(C_2$-$C_6)$alkynyl, perhalo$(C_1$-$C_6)$alkyl, $(R^9)_m$-phenyl, $(R^9)_m$—$(C_1$-$C_{10})$heteroaryl, $(R^9)_m$—$(C_1$-$C_{10})$heterocyclic, or $(R^9)_m$—$(C_3$-$C_{10})$cycloalkyl;

m is an integer from one to three; $R^6$ is selected from the group consisting of hydrogen, $(C_1$-$C_6)$alkyl, $(C_2$-$C_6)$alkenyl, $(C_2$-$C_6)$alkynyl, $(C_3$-$C_{10})$cycloalkyl, phenyl, $(C_1$-$C_{10})$heteroaryl, $(C_1$-$C_{10})$heterocyclic, $R^{13}$—(C=O)—, and $R^{13}$—(SO$_2$)—;

wherein each of the aforesaid $(C_1$-$C_6)$alkyl, $(C_3$-$C_{10})$cycloalkyl, phenyl, $(C_1$-$C_{10})$heteroaryl and $(C_1$-$C_{10})$heterocyclic substituents may optionally be independently substituted on any carbon atom by one to four moieties per substituent independently selected from the group consisting of halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_3$-$C_{10})$cycloalkyl, $(C_1$-$C_{10})$heteroaryl, $(C_1$-$C_{10})$heterocyclic, formyl, —C≡N, $(C_1$-$C_6)$alkyl —(C=O)—, phenyl-(C=O)—, HO—(C=O)—, $(C_1$-$C_6)$alkyl —O—(C=O)—, $(C_1$-$C_6)$alkyl-NH—(C=O)—, $(C_1$-$C_6)$alkyl]$_2$—N—(C=O)—, phenyl-NH—(C=O)—, phenyl-[((C$_1$-$C_6$)alkyl)—N]—(C=O)—, —NO$_2$, amino, $(C_1$-$C_6)$alkylamino, [(C$_1$-$C_6$)alkyl]$_2$-amino, $(C_1$-$C_6)$alkyl-(C=O)—NH—, $(C_1$-$C_6)$alkyl-(C=O)—[((C$_1$-$C_6$)alkyl)—N]—, phenyl-(C=O)—NH—, phenyl-(C=O)—[((C$_1$-$C_6$)alkyl)—N]—, H$_2$N—(C=O)—NH—, $(C_1$-$C_6)$alkyl-HN—(C=O)—NH—, [(C$_1$-$C_6$)alkyl]$_2$—N—(C=O)—NH—, $(C_1$-$C_6)$alkyl-HN—(C=O)—[((C$_1$-$C_6$)alkyl)—N]—, [(C$_1$-$C_6$)alkyl]$_2$—N—(C=O)—[((C$_1$-$C_6$)alkyl)—N]—, phenyl-HN—(C=O)—NH—, (phenyl)$_2$—N—(C=O)—NH—, phenyl-HN—(C=O)—[((C$_1$-$C_6$)alkyl)—N]—, (phenyl-)$_2$—N—(C=O)—[((C$_1$-$C_6$)alkyl)—N]—, $(C_1$-$C_6)$alkyl-O—(C=O)—NH—, $(C_1$-$C_6)$alkyl-O—(C=O)—[((C$_1$-$C_6$)alkyl)—N]—, phenyl-O—(C=O)—NH—, phenyl-O—(C=O)—[((C$_1$-$C_6$)alkyl)—N]—, $(C_1$-$C_6)$alkyl-SO$_2$NH—, phenyl-SO$_2$NH—, $(C_1$-$C_6)$alkyl —SO$_2$—, phenyl-SO$_2$—, hydroxy, $(C_1$-$C_6)$alkoxy, perhalo$(C_1$-$C_6)$alkoxy, phenoxy, $(C_1$-$C_6)$alkyl —(C=O)—O—, phenyl-(C=O)—O—, H$_2$N—(C=O)—O—, $(C_1$-$C_6)$alkyl-HN—(C=O)—O—, [(C$_1$-$C_6$)alkyl]$_2$—N—(C=O)—O—, phenyl-HN—(C=O)—O—, and (phenyl-)$_2$—N—(C=O)—O—;

wherein when said $R^6$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of $(C_1$-$C_6)$alkyl, halo, $(C_1$-$C_6)$alkoxy, perhalo$(C_1$-$C_6)$alkyl and perhalo$(C_1$-$C_6)$alkoxy; $R^7$ is selected from the group consisting of hydrogen, $(C_1$-$C_6)$alky, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, and $(C_3$-$C_{10})$cycloalkyl; $R^8$ is hydrogen, or $(C_1$-$C_6)$alkyl; wherein when $R^9$ is a substituent on a carbon atom each $R^9$ is independently selected from the group consisting of hydrogen, halo, $R^{11}$—$(C_1$-$C_6)$alkyl, $R^{11}$—$(C_2$-$C_6)$alkenyl, $R^{11}$—$(C_2$-$C_6)$alkynyl, azido, perhalo$(C_1$-$C_6)$alkyl, $(C_1$-$C_6)$alkyl-S—, $(C_1$-$C_6)$alkyl-SO$_2$—, $R^{11}$—[N(R$^{10}$)]—SO$_2$—, —NO$_2$, $(R^{11})_2$—N—, $R^{11}$—SO$_2$—[N(R$^{10}$)]—, $R^{11}$—(C=O)—[N(R$^{10}$)]—, $(R^{11})$—[N(R$^{10}$)]—(C=O)—[N(R$^{10}$)]—, $R^{11}$—O—(C=O)—[N(R$^{10}$)]—, —C≡N, $R^{11}$—(C=O)—, $R^{11}$—O—(C=O)—, $(R^{11})$—[N(R$^{10}$)]—(C=O)—, $R^{11}$—O—, perhalo$(C_1$-$C_6)$alkoxy, $R^{11}$—(C=O)—O—, $R^{11}$—O—(C=O)—O— and $(R^{11})$—[N(R$^{10}$)]—(C=O)—O—;

wherein when $R^9$ is a substituent on a nitrogen atom each $R^9$ is independently selected from the group consisting of hydrogen, $R^{11}$—$(C_1$-$C_6)$alkyl, $R^{11}$—$(C_2$-$C_6)$alkenyl, $R^{11}$—$(C_2$-$C_6)$alkynyl, perhalo$(C_1$-$C_6)$alkyl, $(C_1$-$C_6)$alkyl-SO$_2$—, $R^{11}$—[N(R$^{10}$)]—SO$_2$—, $R^{11}$—(C=O)—, $R^{11}$—O—(C=O)— and $(R^{11})$—[N(R$^{10}$)]—(C=O)—; $R^{10}$ is hydrogen or $(C_1$-$C_4)$alkyl; $R^{11}$ is selected from the group consisting of hydrogen, $R^{12}$—$(C_1$-$C_6)$alkyl, $(C_3$-$C_6)$alkenyl, $(C_3$-$C_6)$alkynyl, $(C_1$-$C_{10})$heterocyclic, $(C_1$-$C_{10})$heteroaryl, $(C_3$-$C_{10})$cycloalkyl, and phenyl; wherein each of the aforesaid $R^{12}$—$(C_1$-$C_6)$alkyl, $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, —C≡N, $(C_1$-$C_6)$alkyl, $(C_1$-$C_6)$alkyl-O—(C=O)—, and $(C_1$-$C_6)$alkoxy;

$R^{12}$ is selected from the group consisting of hydrogen, hydroxy, $(C_1$-$C_{10})$heterocyclic, $(C_1$-$C_{10})$heteroaryl, $(C_3$-$C_{10})$cycloalkyl, and phenyl; wherein each of the aforesaid $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, —C≡N, $(C_1$-$C_6)$alkyl, and $(C_1$-$C_6)$alkoxy;

$R^{13}$ is selected from the group consisting of hydrogen, $(C_1$-$C_6)$alkyl, $(C_2$-$C_6)$alkenyl, $(C_2$-$C_6)$alkynyl, perhalo $(C_1$-$C_6)$alkyl, phenyl, $(C_1$-$C_{10})$heteroaryl, $(C_1$-$C_{10})$heterocyclic, $(C_3$-$C_{10})$cycloalkyl, hydroxy, $(C_1$-$C_6)$alkoxy, perhalo$(C_1$-$C_6)$alkoxy, phenoxy, $(C_1$-$C_{10})$heteroaryl-O—, $(C_1$-$C_{10})$heterocyclic-O—, $(C_3$-$C_{10})$cycloalkyl-O—, $(C_1$-$C_6)$alkyl-S—, amino, $(C_1$-$C_6)$alkylamino, [(C$_1$-$C_6$)alkyl]$_2$-amino, $(C_1$-$C_6)$alkyl-SO$_2$—NH—, $(C_1$-$C_6)$alkyl-(C=O)—NH—, $(C_1$-$C_6)$alkyl-(C=O)—[((C$_1$-$C_6$)alkyl)—N]—, phenyl-(C=O)—NH—, and phenyl-(C=O)—[((C$_1$-$C_6$)alkyl)—N—]—;

X is >C(R$^{14}$)$_2$, >NR$^{15}$, sulfur, >S=O, >SO$_2$ or oxygen; each $R^{14}$ is independently selected from the group consisting of hydrogen, halo, $(C_1$-$C_6)$alkyl, $(C_2$-$C_6)$alkenyl, $(C_2$-$C_6)$alkynyl, perhalo$(C_1$-$C_6)$alkyl, phenyl, $(C_1$-$C_{10})$heteroaryl, $(C_1$-$C_{10})$heterocyclic, $(C_1$-$C_{10})$cycloalkyl, hydroxy, $(C_1$-$C_6)$alkoxy, perhalo$(C_1$-$C_6)$alkoxy, phenoxy, $(C_1$-$C_{10})$heteroaryl-O—, $(C_1$-$C_{10})$heterocyclic-O—, $(C_3$-$C_{10})$cycloalkyl-O—, $(C_1$-$C_6)$alkyl-S—, $(C_1$-$C_6)$alkyl-SO$_2$—, $(C_1$-$C_6)$alkyl-NH—SO$_2$—, —NO$_2$, amino, $(C_1$-$C_6)$alkylamino, [(C$_1$-$C_6$)alkyl]$_2$-amino, $(C_1$-$C_6)$alkyl-SO$_2$—NH—, $(C_1$-$C_6)$alkyl —(C=O)—NH—, $(C_1$-$C_6)$alkyl-(C=O)—[((C$_1$-$C_6$)alkyl)—N]—, phenyl-(C=O)—NH—, phenyl-(C=O)—[((C$_1$-$C_6$)alkyl)—N]—, —C—N, $(C_1$-$C_6)$alkyl-(C=O)—, phenyl-(C=O)—, $(C_1$-$C_{10})$heteroaryl-(C=O)—, $(C_1$-$C_{10})$heterocyclic-(C=O)—, $(C_3$-$C_{10})$cycloalkyl-(C=O)—, HO—(C=O)—, $(C_1$-$C_6)$alkyl-O—(C=O)—, H$_2$N(C=O)—, $(C_1$-$C_6)$alkyl- NH—(C=O)—, [(C$_1$-C$_6$)alkyl]$_2$—N—(C=O)—, phenyl-NH—(C=O)—, phenyl-[(C$_1$-C$_6$)alkyl)—N]—(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)— and (C$_1$-C$_6$)alkyl-(C=O)—O—; wherein two R$^{14}$ substituents may be optionally taken together with the carbon atoms to which they are attached to form a five to six membered carbocyclic or heterocyclic ring;

R$^{15}$ is selected from the group consisting of hydrogen, (C$_1$-C$_6$)alkyl, (C$_2$-C$_6$)alkenyl, (C$_2$-C$_6$)alkynyl, (C$_3$-C$_{10}$)cycloalkyl, phenyl, (C$_1$-C$_{10}$)heteroaryl, (C$_1$-C$_{10}$)heterocyclic, R$^{16}$—(C=O)—, and R$^{16}$—(SO$_2$)—; wherein each of the aforesaid (C$_1$-C$_6$)alkyl, (C$_1$-C$_{10}$)cycloalkyl, phenyl, (C$_1$-C$_{10}$)heteroaryl and (C$_1$-C$_{10}$)heterocyclic substituents may optionally be independently substituted on any carbon atom by one to four moieties per substituent independently selected from the group consisting of halo, (C$_1$-C$_6$)alkyl, (C$_2$-C$_6$)alkenyl, (C$_2$-C$_6$)alkynyl, perhalo(C$_1$-C$_6$)alkyl, phenyl, (C$_3$-C$_{10}$)cycloalkyl, (C$_1$-C$_{10}$)heteroaryl, (C$_1$-C$_{10}$)heterocyclic, formyl, —C≡N, (C$_1$-C$_6$)alkyl-(C=O)—, phenyl-(C=O)—, HO—(C=O)—, (C$_1$-C$_6$)alkyl-O—(C=O)—, (C$_1$-C$_6$)alkyl-NH—(C=O)—, [(C$_1$-C$_6$)alkyl]$_2$—N—(C=O)—, phenyl-NH—(C=O)—, phenyl-[((C$_1$-C$_6$)alkyl)—N]—(C=O)—, —NO$_2$, amino, (C$_1$-C$_6$)alkylamino, [(C$_1$-C$_6$)alkyl]$_2$-amino, (C$_1$-C$_6$)alkyl-(C=O)—NH—, (C$_1$-C$_6$)alkyl-(C=O)—[((C$_1$-C$_6$)alkyl)—N]—, phenyl-(C=O)—NH—, phenyl-(C=O)—[((C$_1$-C$_6$)alkyl)—N]—, H$_2$N—(C=O)—NH—, (C$_1$-C$_6$)alkyl-HN—(C=O)—NH—, [(C$_1$-C$_6$)alkyl]$_2$—N—(C=O)—NH—, (C$_1$-C$_6$)alkyl-HN—(C=O)—[((C$_1$-C$_6$)alkyl)—N]—, [(C$_1$-C$_6$)alkyl]$_2$—N—(C=O)—[((C$_1$-C$_6$)alkyl)—N]—, phenyl-HN—(C=O)—NH—, (phenyl)$_2$—N—(C=O)—NH—, phenyl-HN—(C=O)—[((C$_1$-C$_6$)alkyl)—N]—, (phenyl-)$_2$N—(C=O)—[((C$_1$-C$_6$)alkyl)—N]—, (C$_1$-C$_6$)alkyl-O—(C=O)—NH—, (C$_1$-C$_6$)alkyl-O—(C=O)—[((C$_1$-C$_6$)alkyl)—N]—, phenyl-O—(C=O)—NH—, phenyl-O—(C=O)—[((C$_1$-C$_6$)alkyl)—N]—, (C$_1$-C$_6$)alkyl-SO$_2$NH—, phenyl-SO$_2$NH—, (C$_1$-C$_6$)alkyl-SO$_2$—, phenyl-SO$_2$—, hydroxy, (C$_1$-C$_6$)alkoxy, perhalo(C$_1$-C$_6$)alkoxy, phenoxy, (C$_1$-C$_6$)alkyl-(C=O)—O—, phenyl-(C=O)—O—, H$_2$N—(C=O)—O—, (C$_1$-C$_6$)alkyl-HN—(C=O)—O—, [(C$_1$-C$_6$)alkyl]$_2$—N—(C=O)—O—, phenyl-HN—(C=O)—O—, and (phenyl-)$_2$N—(C=O)—O—; wherein each of the aforesaid (C$_1$-C$_{10}$)heteroaryl and (C$_1$-C$_{10}$)heterocyclic substituents may optionally be independently substituted on any nitrogen atom by a substituent selected from the group consisting of (C$_1$-C$_6$)alkyl, (C$_2$-C$_6$)alkenyl, (C$_2$-C$_6$)alkynyl, perhalo(C$_1$-C$_6$)alkyl, phenyl, (C$_3$-C$_{10}$)cycloalkyl, (C$_1$-C$_{10}$)heteroaryl, (C$_1$-C$_{10}$)heterocyclic, formyl, (C$_1$-C$_6$)alkyl-(C=O)—, phenyl-(C=O)—, HO—(C=O)—, (C$_1$-C$_6$)alkyl-O—(C=O)—, (C$_1$-C$_6$)alkyl-NH—(C=O)—, [(C$_1$-C$_6$)alkyl]$_2$—N—(C=O)—, phenyl-NH—(C=O)—, phenyl-[((C$_1$-C$_6$)alkyl)—N]—(C=O)—, (C$_1$-C$_6$)alkyl-SO$_2$— and phenyl-SO$_2$—; wherein when said R$^{15}$ phenyl substituent contains two adjacent moieties, such moieties may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of (C$_1$-C$_6$)alkyl, halo, (C$_1$-C$_6$)alkoxy, perhalo(C$_1$-C$_6$)alkyl and perhalo(C$_1$-C$_6$)alkoxy;

R$^{16}$ is selected from the group consisting of hydrogen, (C$_1$-C$_6$)alkyl, (C$_2$-C$_6$)alkenyl, (C$_2$-C$_6$)alkynyl, perhalo(C$_1$-C$_6$)alkyl, phenyl, (C$_1$-C$_{10}$)heteroaryl, (C$_1$-C$_{10}$)heterocyclic, (C$_3$-C$_{10}$)cycloalkyl, (C$_1$-C$_6$)alkoxy and perhalo(C$_1$-C$_6$)alkoxy;

each R$^{17}$ is independently selected from hydrogen, (C$_1$-C$_6$)alkyl, phenyl, (C$_1$-C$_{10}$)heteroaryl, (C$_1$-C$_{10}$)heterocyclic and (C$_3$-C$_{10}$)cycloalkyl; wherein each of the aforesaid R$^{17}$ substituents (C$_1$-C$_6$)alkyl, phenyl, (C$_1$-C$_{10}$)heteroaryl-, (C$_1$-C$_{10}$)heterocyclic and (C$_3$-C$_{10}$)cycloalkyl may optionally be substituted on any carbon atom by one to four moieties per substituent independently selected from the group consisting of halo, (C$_1$-C$_6$)alkyl, (C$_2$-C$_6$)alkenyl, (C$_2$-C$_6$)alkynyl-I, perhalo(C$_1$-C$_6$)alkyl, phenyl, (C$_1$-C$_{10}$)heteroaryl, (C$_1$-C$_{10}$)heterocyclic, (C$_3$-C$_{10}$)cycloalkyl, hydroxy, (C$_1$-C$_6$)alkoxy, perhalo(C$_1$-C$_6$)alkoxy, phenoxy, (C$_1$-C$_{10}$)heteroaryl-O—, (C$_1$-C$_{10}$)heterocyclic-O—, (C$_3$-C$_{10}$)cycloalkyl-O—, (C$_1$-C$_6$)alkyl-S—, (C$_1$-C$_6$)alkyl-SO$_2$—, (C$_1$-C$_6$)alkyl-NH—SO$_2$—, —NO$_2$, amino, (C$_1$-C$_6$)alkylamino, [(C$_1$-C$_6$)alkyl]$_2$-amino, (C$_1$-C$_6$)alkyl-SO$_2$—NH—, (C$_1$-C$_6$)alkyl-(C=O)—NH—, (C$_1$-C$_6$)alkyl-(C=O)—[((C$_1$-C$_6$)alkyl)—N]—, phenyl-(C=O)—NH—, phenyl-(C=O)—[(C$_1$-C$_6$)alkyl)—N]—, —C≡N, (C$_1$-C$_6$)alkyl-(C=O)—, phenyl-(C=O)—, (C$_1$-C$_{10}$)heteroaryl-(C=O)—, (C$_1$-C$_{10}$)heterocyclic-(C=O)—, (C$_3$-C$_{10}$)cycloalkyl-(C=O)—, HO—(C=O)—, (C$_1$-C$_6$)alkyl-O—(C=O)—, H$_2$N(C=O)—(C$_1$-C$_6$)alkyl-NH—(C=O)—[(C$_1$-C$_6$)alkyl]$_2$—N—(C=O)—, phenyl-NH—(C=O)—, phenyl ((C$_1$-C$_6$)alkyl)—N]—(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)—, (C$_1$-C$_6$)alkyl-(C=O)—O— and phenyl-(C=O)—O—; wherein each of the aforesaid R$^{17}$ substituents (C$_1$-C$_{10}$)heteroaryl and (C$_1$-C$_{10}$)heterocyclic may optionally be substituted on any nitrogen atom by a moiety selected from the group consisting of (C$_1$-C$_6$)alkyl, (C$_2$-C$_6$)alkenyl, (C$_2$-C$_6$)alkynyl, perhalo(C$_1$-C$_6$)alkyl, phenyl, (C$_1$-C$_{10}$)heteroaryl, (C$_1$-C$_{10}$)heterocyclic, (C$_3$-C$_{10}$)cycloalkyl, (C$_1$-C$_6$)alkyl-SO$_2$—, (C$_1$-C$_6$)alkyl-NH—SO$_2$—, (C$_1$-C$_6$)alkyl-(C=O)—, phenyl-(C=O)—, (C$_1$-C$_{10}$)heteroaryl-(C=O)—, (C$_1$-C$_{10}$)heterocyclic-(C=O)—, (C$_3$-C$_{10}$)cycloalkyl-(C=O)—, HO—(C=O)—, (C$_1$-C$_6$)alkyl-O—(C=O)—, H$_2$N(C=O)—(C$_1$-C$_6$)alkyl-NH—(C=O)—, [(C$_1$-C$_6$)alkyl]$_2$—N—(C=O)—, phenyl-NH—(C=O)—, phenyl-[((C$_1$-C$_6$)alkyl)—N]—(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)—, (C$_1$-C$_6$)alkyl-(C=O)—O— and phenyl-(C=O)—O—; wherein two R$^{17}$ (C$_1$-C$_6$)alkyl groups may be taken together with the nitrogen atom to which they are attached to form a five to six membered heterocyclic or heteroaryl ring;

or a pharmaceutically acceptable salt thereof.

3. A compound according to claim 2, wherein R$^3$ is R$^4$.

4. A compound according to claim 3, wherein R$^4$ is hydrogen, halo, —C≡N or perhalo(C$_1$-C$_6$)alkyl.

5. A compound according to claim 3, wherein R$^4$ is (R$^9$)$_m$—(C$_1$-C$_6$)alkyl.

6. A compound according to claim 3, wherein R$^4$ is (R$^9$)$_m$-phenyl, (R$^9$)$_m$—(C$_1$-C$_{10}$)heteroaryl, (R$^9$)$_m$—(C$_1$-C$_{10}$)heterocyclic or (R$^9$)$_m$—(C$_3$-C$_{10}$)cycloalkyl.

7. A compound according to claim 3, wherein $R^4$ is $(R^9)_m$—$(C_1$-$C_6)$alkyl; m is 1; $R^9$ is selected from the group consisting of hydrogen, halo, $R^{11}$—$(C_1$-$C_6)$alkyl, $R^{11}$—$(C_2$-$C_6)$alkenyl, $R^{11}$—$(C_2$-$C_6)$alkynyl, perhalo$(C_1$-$C_6)$alkyl, $(C_1$-$C_6)$alkyl-S—, $(C_1$-$C_6)$alkyl-SO$_2$—, $R^{11}$—$[N(R^{10})]$—SO$_2$—, —NO$_2$, $R^{11}$—SO$_2$—$[N(R^{10})]$—, —C≡N, and perhalo$(C_1$-$C_6)$alkoxy.

8. A compound according to claim 3, wherein $R^4$ is $(R^9)_m$—$(C_1$-$C_6)$alkenyl; m is 1; $R^9$ is selected from the group consisting of hydrogen, halo, $R^{11}$—$(C_1$-$C_6)$alkyl, $R^{11}$—$(C_2$-$C_6)$alkenyl, $R^{11}$—$(C_2$-$C_6)$alkynyl-, perhalo$(C_1$-$C_6)$alkyl, $(C_1$-$C_6)$alkyl-S—, $(C_1$-$C_6)$alkyl-SO$_2$—, $R^{11}$—$[N(R^{10})]$—SO$_2$—, —NO$_2$, $R^{11}$—SO$_2$—$[N(R^{10})]$—, —C≡N, and perhalo$(C_1$-$C_6)$alkoxy.

9. A compound according to claim 3, wherein $R^4$ is $(R^9)_m$—$(C_1$-$C_6)$alkyl; m is 1; $R^9$ is selected from the group consisting of $(R^{11})_2$N—, $R^{11}$—(C=O)—$[N(R^{10})]$—, $(R^{11})$—$[N(R^{10})]$—(C=O)—$[N(R^{10})]$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $R^{11}$—O—(C=O)—O— and $(R^{11})$—$[N(R^{10})]$—(C=O)—O—.

10. A compound according to claim 3, wherein $R^4$ is $(R^9)_m$—$(C_1$-$C_6)$alkyl; m is 1; $R^9$ is selected from the group consisting of $(R^{11})_2$N—, $R^{11}$—(C=O)—$[N(R^{10})]$—, $(R^{11})$—$[N(R^{10})]$—(C=O)—$[N(R^{10})]$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $R^{11}$—O—(C=O)—O— and $(R^{11})$—$[N(R^{10})]$—(C=O)—O—; and $R^{11}$ is selected from the group selected from hydrogen, $R^{12}$—$(C_1$-$C_6)$alkyl, $(C_3$-$C_6)$alkenyl, and $(C_3$-$C_6)$alkynyl.

11. A compound according to claim 3, wherein $R^4$ is $(R^9)_m$—$(C_1$-$C_6)$alkyl; m is 1; $R^9$ is selected from the group consisting of $R^{11}$—(C=O)—$[N(R^{10})]$—, $(R^{11})$—$[N(R^{10})]$—(C=O)—$[N(R^{10})]$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $R^{11}$—O—(C=O)—O— and $(R^{11})$—$[N(R^{10})]$—(C=O)—O—; and $R^{11}$ is selected from the group selected from $(C_1$-$C_{10})$heterocyclic, $(C_1$-$C_{10})$heteroaryl, $(C_3$-$C_{10})$cycloalkyl, and phenyl; wherein each of the aforesaid $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, $(C_1$-$C_6)$alkyl, and $(C_1$-$C_6)$alkoxy.

12. A compound according to claim 3, wherein $R^4$ is $(R^9)_m$—$(C_1)$alkyl; m is 1; $R^9$ is selected from the group consisting of hydrogen, halo, $R^{11}$—$(C_1$-$C_6)$alkyl, $R^{11}$—$(C_2$-$C_6)$alkenyl, $R^{11}$—$(C_2$-$C_6)$alkynyl, perhalo$(C_1$-$C_6)$alkyl, $(C_1$-$C_6)$alkyl-S—, $(C_1$-$C_6)$alkyl-SO$_2$—, $R^{11}$—$[N(R^{10})]$—SO$_2$—, —NO$_2$, $R^{11}$—SO$_2$—$[N(R^{10})]$—, —C≡N, and perhalo$(C_1$-$C_6)$alkoxy; and $R^{11}$ is selected from the group consisting of $(C_1$-$C_{10})$heterocyclic, $(C_1$-$C_{10})$heteroaryl, $(C_3$-$C_{10})$cycloalkyl, and phenyl; wherein each of the aforesaid $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, $(C_1$-$C_6)$alkyl, and $(C_1$-$C_6)$alkoxy.

13. A compound according to claim 3, wherein $R^4$ is $(R^9)_m$—$(C_1)$alkyl; m is 1; $R^9$ is selected from the group consisting of $(R^{11})_2$N—, $R^{11}$—(C=O)—$[N(R^{10})]$—, $(R^{11})$—$[N(R^{10})]$—(C=O)—$[N(R^{10})]$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $(R^{11}$—O—(C=O)—O— and $(R^{11})$—$[N(R^{10})]$—(C=O)—O—; and $R^{11}$ is hydrogen, $R^{12}$—$(C_1$-$C_6)$alkyl, $(C_3$-$C_6)$alkenyl, and $(C_3$-$C_6)$alkynyl.

14. A compound according to claim 3, wherein $R^4$ is $(R^9)_m$—$(C_1)$alkyl; m is 1; $R^9$ is selected from the group consisting of $(R^{11})_2$N—, $R^{11}$—(C=O)—$[N(R^{10})]$—, $(R^{11})$—$[N(R^{10})]$—(C=O)—$[N(R^{10})]$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $R^{11}$—O—(C=O)—O— and $(R^{11})$—$[N(R^{10})]$—(C=O)—O—; and $R^{11}$ is selected from the group selected from $(C_1$-$C_{10})$heterocyclic, $(C_1$-$C_{10})$heteroaryl, $(C_3$-$C_{10})$cycloalkyl, and phenyl; wherein each of the aforesaid $(C_1$-$C_{10})$heterocyclic, $(C_1$-$C_{10})$heteroaryl, $(C_3$-$C_{10})$cycloalkyl, and phenyl substituents may optionally be substituted with one to three moieties independently selected from halo, $(C_1$-$C_6)$alkyl, and $(C_1$-$C_6)$alkoxy.

15. A compound according to claim 3, wherein $R^4$ is $(R^9)_m$—$(C_1)$alkyl; m is 1; $R^9$ is selected from the group consisting of $R^{11}$—(C=O)—$[N(R^{10})]$—, $(R^{11})$—$[N(R^{10})]$—(C=O)—$(N(R^{10}))$—, $R^{11}$—O—(C=O)—$[N(R^{10})]$—, $R^{11}$—(C=O)—, $R^{11}$—O—(C=O)—, $(R^{11})$—$[N(R^{10})]$—(C=O)—, $R^{11}$—O—, $R^{11}$—(C=O)—O—, $R^{11}$—O—(C=O)—O— and $(R^{11})$—$[N(R^{10})]$—(C=O)—O—; and $R^{11}$ is selected from the group consisting of hydrogen, $R^{12}$—$(C_1$-$C_6)$alkyl and $(C_1$-$C_{10})$heteroaryl; wherein each of the aforesaid $(C_1$-$C_6)$alkyl and $(C_1$-$C_{10})$heteroaryl substituents may optionally be substituted with one to three moieties independently selected from halo, $(C_1$-$C_6)$alkyl, and $(C_1$-$C_6)$alkoxy.

16. A compound according to claim 2 wherein X is >C$(R^{14})_2$.

17. A compound according to claim 2 wherein X is >NR$^{15}$.

18. A compound according to claim 2 wherein X is —S—.

19. A compound according to claim 2 wherein X is >S=O.

20. A compound according to claim 2 wherein X is >SO$_2$.

21. A compound according to claim 2 wherein X is —O—.

22. A compound according to claim 2 wherein $R^1$ is optionally substituted $(C_1$-$C_6)$alkyl, phenyl, $(C_3$-$C_{10})$cycloalkyl, $(C_1$-$C_{10})$heteroaryl or $(C_1$-$C_{10})$heterocyclic.

23. A compound according to claim 2 wherein $R^1$ is $(C_1$-$C_6)$alkyl, optionally substituted with one to four groups independently selected from halo, hydroxy, $(C_1$-$C_6)$alkyl, $(C_2$-$C_6)$alkenyl, $(C_2$-$C_6)$alkynyl, $(C_1$-$C_6)$alkoxy, perhalo$(C_1$-$C_6)$alkyl, perhalo$(C_1$-$C_6)$alkoxy, —C≡N, —NO$_2$, amino, $(C_1$-$C_6)$alkylamino, $[(C_1$-$C_6)$alkyl]$_2$-amino, HO—(C=O)—, $(C_1$-$C_6)$alkyl-(C=O)—, $(C_1$-$C_6)$alkyl-O—(C=O)—, $(C_1$-$C_6)$alkyl-CO$_2$—, $(C_1$-$C_6)$alkyl-(C=O)—NH—, $(C_1$-$C_6)$alkyl-NH—(C=O)—, $(C_1$-$C_6)$alkyl-(C=O)—$[((C_1$-$C_6)$alkyl)—N]$—, $(C_1$-$C_6)$alkyl-$[((C_1$-$C_6)$alkyl)—N]$—(C=O)—, $(C_1$-$C_6)$alkyl-SO$_2$NH—, $(C_1$-$C_6)$alkyl-SO$_2$—, optionally substituted phenyl-(C=O)—, optionally substituted phenyl-(C=O)—O—, optionally substituted phenoxy, optionally substituted phenyl-NH—(C=O)—, optionally substituted phenyl-$[((C_1$-$C_6)$alkyl)—N]$—(C=O)—, optionally substituted phenyl-(C=O)—NH— and optionally substituted phenyl-(C=O)—$[((C_1$-$C_6)$alkyl)—N]$—.

24. A compound according to claim 23 wherein $R^1$ is $(C_1$-$C_4)$alkyl.

25. A compound according to claim 23 wherein $R^1$ is optionally substituted $(C_3$-$C_6)$cycloalkyl.

26. A compound according to claims 23 wherein $R^1$ is optionally substituted phenyl.

27. A compound according to claim 26 wherein $R^1$ is optionally substituted phenyl wherein said substituents are independently selected from the group consisting of halo, $(C_1-C_6)$alkyl, $(C_2-C_6)$alkenyl, perhalo$(C_1-C_6)$alkyl, —C≡N, $(C_1-C_6)$alkyl-(C=O)—, HO—(C=O)—, $(C_1-C_6)$alkyl-O—(C=O)—, $(C_1-C_6)$alkyl-NH—(C=O)—, [$(C_1-C_6)$alkyl]$_2$—N—(C=O)—, amino, $(C_1-C_6)$alkylamino, [$(C_1-C_6)$alkyl]$_2$-amino, $(C_1-C_6)$alkyl-(C=O)—NH—, $(C_1-C_6)$alkyl-(C=O)—[(($C_1-C_6)$alkyl)—N]—, $H_2N$—(C=O)—NH—, $(C_1-C_6)$alkyl-HN—(C=O)—NH—, [$(C_1-C_6)$alkyl-]$_2$N—(C=O)—NH—, $(C_1-C_6)$alkyl-HN—(C=O)—[(($C_1-C_6)$alkyl)—N]—, [$(C_1-C_6)$alkyl]$_2$—N—(C=O)—[(($C_1-C_6)$alkyl)—N]—, hydroxy, $(C_1-C_6)$alkoxy, perhalo$(C_1-C_6)$alkoxy, $(C_1-C_6)$alkyl-(C=O)—O—, $H_2N$—(C=O)—O—, $(C_1-C_6)$alkyl-HN—(C=O)—O— and [$(C_1-C_6)$alkyl]$_2$—N—(C=O)—O—.

28. A compound according to claim 26 wherein $R^1$ is optionally substituted phenyl containing two adjacent substituents which taken together with the carbon atoms to which they are attached form a five to six membered carbocyclic or heterocyclic ring.

29. A compound according to claim 2 wherein $R^1$ is $(R^{17})_2$—N—, wherein each $R^{17}$ is independently selected from hydrogen, $(C_1-C_6)$alkyl, phenyl, $(C_1-C_{10})$heterocyclic and $(C_3-C_{10})$cycloalkyl; wherein each of the aforesaid $R^{17}$, $(C_1-C_6)$alkyl, phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[(($C_1-C_6)$alkyl)—N]—, phenyl-(C=O)—NH—, phenyl-(C=O)—[(($C_1-C_6)$alkyl)—N]—, —C≡N, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)—(C1-$C_6$)alkyl-NH—(C=O)—, [$(C_1-C_6)$alkyl]$_2$—N—(C=O)—, phenyl-NH—(C=O)—, phenyl-[(($C_1-C_6)$alkyl)—N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^2$ $(C_1-C_6)$alkyl groups may be taken together with the nitrogen atom to form a five to six membered heterocyclic or heteroaryl ring.

30. A compound according to claim 29 wherein $R^1$ is $(R^{17})_2$—N— and wherein each $R^{17}$ is independently selected from hydrogen, $(C_1-C_4)$alkyl, phenyl and $(C_1-C_{10})$heterocyclic.

31. A compound according to claim 29 wherein $R^1$ is $(R^{17})_2$—N— and wherein two $R^2$ $(C_1-C_6)$alkyl groups may be taken together with the nitrogen atom to form a five to six membered heterocyclic or heteroaryl ring.

32. A compound according to claim 2, wherein s is an integer from one to four and each $R^2$ is independently selected from the group consisting of halo, —C≡N, $(C_1-C_6)$alkyl, $(C_2-C_6)$alkenyl, $(C_2-C_6)$alkynyl and perhalo$(C_1-C_6)$alkyl.

33. A compound according to claim 2, wherein s is an integer from one to four and zero, one or two of $R^2$ are independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, amino, $(C_1-C_6)$alkylamino, [$(C_1-C_6)$alkyl]$_2$-amino, —C≡N, and $H_2N(C=O)$—.

34. A compound according to claim 2, wherein s is an integer from one to three and each $R^2$ is independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, —NO$_2$, amino, $(C_1-C_6)$alkylamino, [$(C_1-C_6)$alkyl]$_2$-amino, —C≡N, and $H_2N(C=O)$—.

35. A compound according to claim 2, wherein s is an integer from one to two and each $R^2$ is independently selected from the group consisting of halo, $(C_1-C_6)$alkyl, perhalo$(C_1-C_6)$alkyl, $(C_1-C_6)$alkoxy, perhalo$(C_1-C_6)$alkoxy and —C≡N.

36. A compound according to claim 35, wherein s is an integer from one to three and each $R^2$ is independently selected from the group consisting of fluoro, chloro and methyl.

37. A compound according to claim 2, wherein said compound is selected from the group consisting of:

1-Ethyl-3-[2-(3-isopropyl-[1,2,4]triazolo[4,3-a]pyridin-6-ylsulfanyl)-benzyl]-urea;

Ethyl-carbamic acid 2-(3-isopropyl-[1,2,4]triazolo[4,3-a]pyridin-6-ylsulfanyl)-benzyl ester;

[2-(3-Isopropyl-[1,2,4]triazolo[4,3-a]pyridin-6-ylsulfanyl)-benzyl]-carbamic acid ethyl ester;

1-(5-tert-Butyl-2-methyl-2H-pyrazol-3-yl)-3-[2-(3-isopropyl-[1,2,4]triazolo[4,3-a]pyridin-6-ylsulfanyl)-benzyl]-urea;

Ethyl-carbamic acid 2-(3-tert-butyl-[1,2,4]triazolo[4,3-a]pyridin-6-ylsulfanyl)-benzyl ester;

1-(5-tert-Butyl-isoxazol-3-yl)-3-[2-(3-isopropyl-[1,2,4]triazolo[4,3-a]pyridin-6-ylsulfanyl)-benzyl]-urea;

Ethyl-carbamic acid 5-fluoro-2-(3-isopropyl-[1,2,4]triazolo[4,3-a]pyridin-6-ylsulfanyl)-benzyl ester;

Ethyl-carbamic acid 2-fluoro-6-(3-isopropyl-[1,2,4]triazolo[4,3-a]pyridin-6-ylsulfanyl)-benzyl ester; and N-Ethyl-3-[2-(3-isopropyl-[1,2,4]triazolo[4,3-a]pyridin-6-ylsulfanyl)-phenyl]-acrylamide.

* * * * *